United States Patent
Sundaram et al.

(10) Patent No.: US 11,826,165 B2
(45) Date of Patent: *Nov. 28, 2023

(54) DEVICES, SYSTEMS, AND METHODS FOR ADAPTIVE HEALTH MONITORING USING BEHAVIORAL, PSYCHOLOGICAL, AND PHYSIOLOGICAL CHANGES OF A BODY PORTION

(71) Applicant: Plethy, Inc., San Jose, CA (US)

(72) Inventors: Raja Sundaram, Los Gatos, CA (US); Ravi Jagannathan, San Jose, CA (US); Hari Harikrishnan, Fremont, CA (US)

(73) Assignee: PLETHY, INC., San Jose, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/182,597

(22) Filed: Mar. 13, 2023

(65) Prior Publication Data
US 2023/0255555 A1   Aug. 17, 2023

Related U.S. Application Data

(63) Continuation of application No. 16/755,399, filed as application No. PCT/US2018/055384 on Oct. 11, 2018, now Pat. No. 11,672,477.
(Continued)

(51) Int. Cl.
*A61B 5/00* (2006.01)
*G16H 20/30* (2018.01)
(Continued)

(52) U.S. Cl.
CPC ............ *A61B 5/486* (2013.01); *A61B 5/0002* (2013.01); *A61B 5/01* (2013.01); *A61B 5/1032* (2013.01);
(Continued)

(58) Field of Classification Search
None
See application file for complete search history.

(56) References Cited

U.S. PATENT DOCUMENTS

| 5,497,787 A | 3/1996 | Nemesdy et al. |
| 5,991,654 A | 11/1999 | Tumey et al. |
| (Continued) | | |

FOREIGN PATENT DOCUMENTS

| EP | 1151719 A2 | 11/2001 |
| WO | 9300042 A1 | 1/1993 |
| (Continued) | | |

OTHER PUBLICATIONS

International Search Report dated Mar. 24, 2017 from International Application PCT/US2016/63419, 3 pgs.
(Continued)

*Primary Examiner* — Benjamin S Melhus
(74) *Attorney, Agent, or Firm* — Aurora Consulting LLC; Kristen J. Hansen; Ashley Sloat

(57) ABSTRACT

Devices, systems, and methods for monitoring musculoskeletal (MSK) health conditions of an individual, including joint flexibility, strength, and endurance as part of their overall care plan are described here. The overall system includes: a sensor that can be worn anywhere on the human body, an engaging app on a mobile-computing device, and software-based analytics and care management engine running on a cloud-computing infrastructure. The sensor is tuned to measure any human joint movement in any direction or axis as well as elevation and temperature. Methods performed by the various devices and systems and how it improves MSK health are provided.

14 Claims, 28 Drawing Sheets

Fail Risk

Adherence Risk

Readmission Risk

Related U.S. Application Data

(60) Provisional application No. 62/699,286, filed on Jul. 17, 2018, provisional application No. 62/570,819, filed on Oct. 11, 2017.

(51) Int. Cl.

| | | |
|---|---|---|
| *G16H 40/67* | (2018.01) | |
| *A61B 5/01* | (2006.01) | |
| *A61B 5/103* | (2006.01) | |
| *A61B 5/11* | (2006.01) | |
| *A61B 5/16* | (2006.01) | |
| *A61B 5/22* | (2006.01) | |

(52) U.S. Cl.
CPC .......... *A61B 5/1114* (2013.01); *A61B 5/1118* (2013.01); *A61B 5/1121* (2013.01); *A61B 5/165* (2013.01); *A61B 5/224* (2013.01); *A61B 5/4519* (2013.01); *A61B 5/4528* (2013.01); *A61B 5/4806* (2013.01); *A61B 5/4824* (2013.01); *A61B 5/4833* (2013.01); *A61B 5/4884* (2013.01); *A61B 5/6801* (2013.01); *A61B 5/7275* (2013.01); *A61B 5/742* (2013.01); *A61B 5/746* (2013.01); *G16H 20/30* (2018.01); *G16H 40/67* (2018.01); *A61B 2562/0219* (2013.01)

(56) References Cited

U.S. PATENT DOCUMENTS

| | | | |
|---|---|---|---|
| 6,047,203 | A | 4/2000 | Sackner et al. |
| 6,381,482 | B1 | 4/2002 | Jayaraman et al. |
| 6,941,775 | B2 | 9/2005 | Sharma |
| 6,980,853 | B2 | 12/2005 | Miyoshi et al. |
| 7,191,803 | B2 | 3/2007 | Orr et al. |
| 7,319,895 | B2 | 1/2008 | Klefstad-Sillonville et al. |
| 7,474,910 | B2 | 1/2009 | Hassonjee et al. |
| 7,559,902 | B2 | 7/2009 | Ting et al. |
| 7,849,888 | B2 | 12/2010 | Karayianni et al. |
| 8,146,171 | B2 | 4/2012 | Chung et al. |
| 8,403,881 | B2 | 3/2013 | Ferren et al. |
| 8,409,132 | B2 | 4/2013 | Ferren et al. |
| 8,551,008 | B2 | 10/2013 | Naghavi et al. |
| 8,585,602 | B2 | 11/2013 | Crabtree et al. |
| 8,597,194 | B2 | 12/2013 | Barak |
| 8,636,670 | B2 | 1/2014 | Ferren et al. |
| 8,870,813 | B2 | 10/2014 | Ferren et al. |
| 8,925,392 | B2 | 1/2015 | Esposito et al. |
| 9,186,092 | B2 | 11/2015 | Mestrovic et al. |
| 9,459,089 | B2 | 10/2016 | Ganton et al. |
| 10,722,145 | B2 * | 7/2020 | Sundaram ............ A61B 5/1032 |
| 2005/0059903 | A1 | 3/2005 | Izumi |
| 2007/0225614 | A1 | 9/2007 | Naghavi et al. |
| 2008/0157980 | A1 | 7/2008 | Sachanandani et al. |
| 2009/0079559 | A1 | 3/2009 | Dishongh et al. |
| 2009/0234262 | A1 | 9/2009 | Reid, Jr. et al. |
| 2009/0309579 | A1 | 12/2009 | Cochran |
| 2010/0137701 | A1 | 6/2010 | Papastefanou |
| 2010/0240967 | A1 | 9/2010 | Kim et al. |
| 2010/0292549 | A1 | 11/2010 | Shuler |
| 2011/0060252 | A1 | 3/2011 | Simonsen et al. |
| 2012/0065561 | A1 | 3/2012 | Ballas et al. |
| 2012/0123802 | A1 | 5/2012 | Feldman et al. |
| 2012/0173319 | A1 | 7/2012 | Ferrara |
| 2012/0179020 | A1 | 7/2012 | Wekell |
| 2013/0116514 | A1 | 5/2013 | Kroner et al. |
| 2013/0222565 | A1 * | 8/2013 | Guerin ............... A63F 13/211 348/77 |
| 2014/0088461 | A1 | 3/2014 | Mack et al. |
| 2014/0257836 | A1 | 9/2014 | Walker et al. |
| 2014/0296651 | A1 | 10/2014 | Stone |
| 2015/0019135 | A1 | 1/2015 | Kacyvenski et al. |
| 2015/0351698 | A1 | 12/2015 | Cronin |
| 2016/0015297 | A1 | 1/2016 | Strauss et al. |
| 2016/0081594 | A1 | 3/2016 | Gaddipati et al. |
| 2016/0107309 | A1 * | 4/2016 | Walsh ............... A63B 21/0054 248/550 |
| 2016/0220175 | A1 * | 8/2016 | Tam .................... A61B 5/4528 |
| 2016/0232322 | A1 | 8/2016 | Mensinger et al. |
| 2016/0242646 | A1 | 8/2016 | Obma |
| 2016/0278642 | A1 | 9/2016 | Vogel et al. |
| 2016/0302721 | A1 | 10/2016 | Wiedenhoefer et al. |
| 2016/0367406 | A1 | 12/2016 | Barnett |
| 2017/0000386 | A1 * | 1/2017 | Salamatian ............ G16H 10/60 |
| 2017/0049394 | A1 | 2/2017 | Zhang et al. |
| 2017/0069223 | A1 * | 3/2017 | Cramer ............... A63F 13/218 |
| 2017/0136296 | A1 * | 5/2017 | Barrera ............... G16H 20/30 |
| 2017/0140121 | A1 | 5/2017 | Schulhauser et al. |
| 2017/0202724 | A1 * | 7/2017 | De Rossi ............. A61H 3/00 |
| 2017/0238849 | A1 * | 8/2017 | Chapman ........... A61B 5/6832 |
| 2017/0265800 | A1 * | 9/2017 | Auchinleck ......... A61B 5/01 |
| 2017/0367644 | A1 * | 12/2017 | Sharman ............. A61B 5/1121 |
| 2018/0263560 | A1 * | 9/2018 | Bakker ............... A61B 5/4884 |
| 2019/0038225 | A1 * | 2/2019 | Leavitt ............... G16H 10/60 |

FOREIGN PATENT DOCUMENTS

| | | |
|---|---|---|
| WO | 2005067796 A1 | 7/2005 |
| WO | 2009125327 A1 | 10/2009 |
| WO | 2013030709 A2 | 3/2013 |
| WO | 2014207653 A1 | 12/2014 |

OTHER PUBLICATIONS

Written Opinion dated Mar. 24, 2017 from International Application PCT/US2016/63419, 10 pgs.

\* cited by examiner

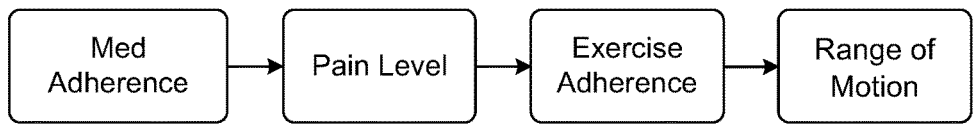
FIG. 14A
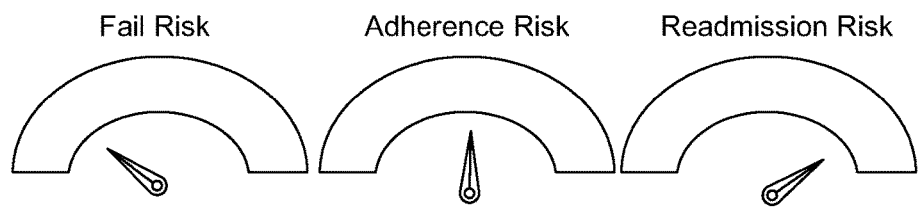
FIG. 14B
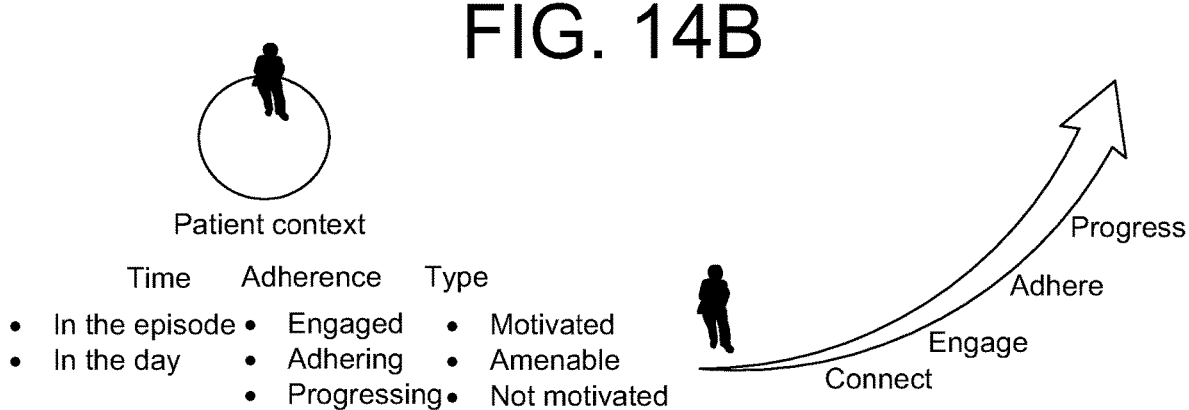
FIG. 14C
FIG. 14D
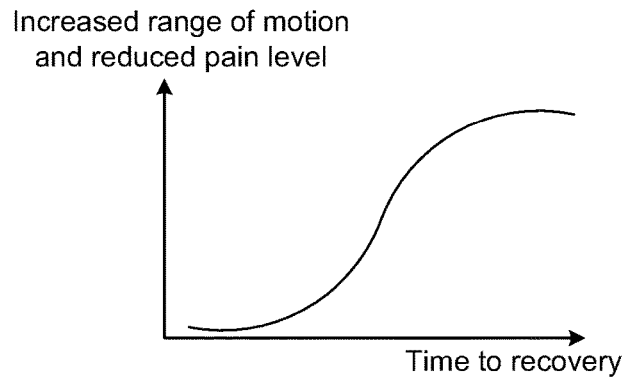
FIG. 14E

DEVICES, SYSTEMS, AND METHODS FOR ADAPTIVE HEALTH MONITORING USING BEHAVIORAL, PSYCHOLOGICAL, AND PHYSIOLOGICAL CHANGES OF A BODY PORTION

CROSS-REFERENCE TO RELATED APPLICATIONS

This application is a continuation of U.S. Nonprovisional patent application Ser. No. 16/755,399 filed Apr. 10, 2020, which is the U.S. National Stage filing of PCT Application Ser. No. PCT/US2018/055384 filed Oct. 11, 2018, which claims the priority benefit of U.S. Provisional Patent Application Ser. No. 62/570,819, filed Oct. 11, 2017 and U.S. Provisional Patent Application Ser. No. 62/699,286, filed Jul. 17, 2018, the contents of each of which are herein incorporated by reference in their entireties.

TECHNICAL FIELD

This disclosure relates to the fields of health and wellness, and more specifically, to devices, systems, and methods for digitally monitoring one or more health indicators of an individual, including positional, orientational, and circumferential changes to one or more body portions.

BACKGROUND

As people live longer, muscular skeletal health is a leading indicator for acute and chronic health conditions. Precise tracking and analysis of joint movement, gait and other aspects including, for example, increased circumference of a patient's limb, torso, waistline, or other body portion can enable the assessment and maintenance of overall wellness and assist in recovery from injuries, as well as assessment of health before and after a surgical or injury episode and overall health. Additionally, monitoring other changes including a rapid increase in the circumference of a patient's limb, torso, waistline, or other body portion can provide insight into other conditions that may or may not effect general health or mobility, for example monitoring a rapid increase in the circumference of a patient's leg may provide insight into a swelling of the leg due to edema. Edema may be indicative of deep vein thrombosis, congestive heart failure, liver disease, kidney disease, an allergic reaction, inflammation caused by injury or infection, or other serious medical condition. Gradual increases in the circumference of a waistline or other body portion may be due to weight gain, which itself may be indicative of inactivity, overeating, depression, a hormonal imbalance, or other medically-relevant condition. On the other hand, for some individuals, such as those being treated for cancer, pregnant women, undernourished individuals, and athletes, a gradual increase in the circumference of a body portion may be desirable, and may be indicative of healthy weight gain, a growing fetus, or an increase in muscle mass. In each of the above scenarios, monitoring any combination of movement, gait, and the circumference of a body portion may provide valuable insights into the health or wellness of an individual.

Methods for monitoring can comprise adaptively providing a digital care plan and performing real-time monitoring and customized patient-specific feedback on patient progression, performance, and adherence to the care protocol. A care protocol can comprise methods for monitoring movements of a patient's joints to assess and improve the muscular skeletal (MSK) health of a patient or user managing symptoms of a chronic condition, recovering from or preparing for a surgical procedure or as a means of early detection of health problems.

Current medical systems are incapable of collecting data about the psychological and behavioral aspects of patients, which directly impact the quality and speed of patient recovery. Furthermore, the disjointed roles of multiple healthcare providers result in a lack of integration of information in a way that is useful and supportive of the patient in their ongoing recovery outside of direct supervision. Finally, the lack of mechanisms that adapt to the needs and schedule of patients in their daily lives outside of supervised medical contexts limits the ability to provide adequate recovery support and meaningfully enlist the support of critical influences like support of friends and family during critical periods of a patient's recovery. Disclosed herein a unified care system comprising adaptable content provided to the user, a care cloud comprising systems and devices for on-going collection of data, and communication tools that facilitate and broker timely communication between healthcare providers, the patient's support network (e.g., family, friends, home care providers, etc.) and the patient.

SUMMARY

There is a need for improved means for monitoring musculoskeletal health conditions of individuals (e.g., joint flexibility, strength, and endurance) as part of the health care regime or provider prescribed care plan. In particular, there is a need for devices, systems, and methods that can encourage individuals to engage in activities and habits that both improve overall health as well as assist in preparation for and recovery from medical procedures or chronic conditions. There is a need for devices, systems, and methods that can monitor and precisely track and analyze joint movements and gait allowing overall assessment of wellness and assist in health preparation before and after a surgical or injury episode. There is also a need, more generally, for devices, systems, and methods that can: detect joint movements and gait and adaptively adjust a care protocol to the daily needs of the patient by providing relevant health or fitness recommendations to an individual, and determine whether an individual has complied with the recommendations. The present disclosure is directed to devices, systems, algorithms, and methods that fill one or more of these needs.

One aspect of the disclosure is directed to a method for monitoring health parameters of an individual, including joint movements, gait, positional, orientational, and/or circumferential changes to a portion of a body. The method includes obtaining a plurality of measurements (e.g., circumferential, relative positon, position over time, etc.) of the body portion over a period of time via a sensor system, transmitting the measurements from the sensor system to a mobile computing device, processing the measurements to track and analyze any change in the circumference, orientation, relative position, etc. of the body portion, and generating an alert output based, at least in part, on the analyzed change in circumference, orientation, relative position, etc. In some embodiments, processing the measurements (e.g., circumferential, relative positon, position over time, etc.) to track and analyze any change in movement, activity, circumference, etc. is performed fully or partially by the mobile computing device. In some embodiments, processing the measurements (e.g., circumferential, relative positon, position over time, etc.) to track and analyze any change is performed fully or partially by a network computing device that may receive the measurements (e.g., circumferential, relative positon, position over time, etc.) from the mobile computing device. In some embodiments, the method further includes querying the individual for user inputs. In such embodiments, the alert output may also be based, in part, on these user inputs. Additionally or alternatively, in some embodiments, the method also includes transmitting the measurements, user inputs, and/or other data acquired by the mobile computing device to a healthcare provider, coach, or other authorized user.

Another aspect of the disclosure is directed to a monitoring system configured to detect changes (e.g., circumferential, orientation, relative positon, position over time, etc.) to a portion of a body. The monitoring system includes a sensor system wearable on or around a portion of an individual's body, which is configured to obtain and transmit a plurality of measurements (e.g., circumferential, relative positon, orientation, position over time, etc.) of the body portion over a period of time. The monitoring system also includes a mobile computing device, which includes a processor and a non-transitory computer-readable medium with instructions stored thereon. The instructions, when executed by the processor, cause the processor to: receive the transmitted measurements (e.g., circumferential, orientation, relative positon, position over time, etc.), process the measurements to track and analyze any change in the body portion, and generate an alert output based, at least in part, on the analyzed change. In some embodiments, the instructions stored on the computer-readable medium further cause the processor to query the individual for user inputs. In such embodiments, the alert output may also be based, in part, on these user inputs.

In some embodiments, the monitoring system is configured to monitor for abnormal swelling of a limb, for example, swelling caused by interstitial edema, deep vein thrombosis, pulmonary embolism, lymphedema, or other medical condition. In such embodiments, the monitored body portion may be, for example, one or both legs. The body portion of some embodiments includes the right and left legs or arms of an individual, and the sensor system includes a first component configured to obtain a first plurality of measurements (e.g., circumferential, position, orientation, etc.) over time from a fixed location on the right leg or arm, and a second component configured to obtain a second plurality of measurements over time from an equivalent fixed location on the left leg or arm. In some such embodiments, processing the measurements to track and analyze any change (e.g., circumferential, relative positon, position over time, orientation, etc.) includes: comparing the first plurality of measurements (e.g., circumferential, relative positon, orientation, position over time, etc.) to each other to detect a change in right leg or arm over time, comparing the second plurality of measurements (e.g., circumferential, relative positon, orientation, position over time, etc.) to each other to detect a change in the left leg or arm over time, and calculating a difference between the change of the right leg or arm and the change of the left leg or arm. The difference between the change of the right leg or arm (e.g., circumferential, relative positon, position over time, orientation, etc.) and the change of the left leg or arm (e.g., circumferential, relative positon, position over time, orientation, etc.) may contribute to a determination of a timing or content of the alert output. For example, the alert output may be generated when the difference between the change in the right leg or arm and the change in the left leg or arm exceeds a threshold value.

In some embodiments of the monitoring system, the user inputs prompted and received by the mobile computing device include symptoms and/or risk factor data. Additionally or alternatively, the user inputs may include an indication of whether the individual has complied with a prescribed instruction. The prescribed instruction may be prescribed by a healthcare provider or the monitoring system. In some embodiments, the prescribed instructions are customizable by a healthcare provider via a remote computing device communicatively coupled to the mobile computing device.

The mobile computing device may be further configured to compute a compliance score indicative of the degree to which the individual complied with the prescribed instructions. The compliance score may be calculated based on one or more of: the change in a body portion (e.g., circumferential, relative positon, position over time, orientation, etc.), the user inputs, detected motion of the body portion indicative of an exercise, and a detected orientation of the body portion. For example, if the prescribed instructions include an instruction to upwardly tilt or elevate the legs, the compliance score may be determined, at least in part, by monitoring leg orientation. Such a sensor system may include a gyroscope. If the prescribed instructions include an instruction to perform leg exercises, the compliance score may be determined, at least in part, by monitoring leg movement. Such a sensor system may include an accelerometer. If the prescribed instructions include an instruction to administer a medication, the compliance score may be determined, at least in part, from a user-entered input indicating medication administration. The compliance score may be transmitted by the mobile computing device to a network computing device in order to be accessible to a healthcare provider or other authorized user.

In some embodiments of the monitoring system, the alert output includes an instruction to the individual to consult a healthcare provider for evaluation. In some embodiments, the alert output is generated when an overall score exceeds a predefined threshold. The overall score may correspond to a likelihood of onset of a disease that causes abnormal swelling of a limb. For example, the overall score may correspond to the likelihood that the individual has developed interstitial edema, deep vein thrombosis, pulmonary embolism, or lymphedema. Various parameters may contribute to the overall score, including one or more of: the change in a body portion (e.g., circumferential, relative positon, position over time, orientation, etc.), a skin temperature at the body portion, a skin color at the body portion, one or more user inputs related to symptoms or risk factors, and the compliance score.

In some embodiments, the monitoring system can comprise mechanisms for brokering or supporting communication between multiple parties, including multiple healthcare providers, family, friends, home care providers, etc.

In some embodiments, the monitoring system is configured to monitor for changes in the circumference of a body portion resulting from weight gain, weight loss, the development of a fetus within a woman's uterus, or changes in muscle mass. In such embodiments, the body portion may include one or more of a limb (or limbs), an upper torso (i.e., chest), and a lower torso (i.e., waist). The user inputs prompted and received by the mobile computing device may include data inputs related to one or more of: an exercise performed, a food consumed, a supplement consumed, a medication administered, duration of sleep, and a user-perceived wellness rating. The alert output may include an evaluation of weight loss progress, fetal development, or strength training effectiveness or progress. The mobile computing device of the monitoring system may be further configured to output guidance, such as recommended exercises, meal plans, and/or other wellness tips and reminders tailored to the individual based on one or more of: the change in the body portion (e.g., circumferential, relative positon, orientation, position over time, etc.), detected movement of the body portion, and the user inputs.

In various embodiments of the monitoring system, the sensor system includes a stretchable component and a sensor module coupled thereto. The stretchable component is configured to fit securely around the body portion. The stretchable component may be formed of a stretchable band, sleeve, belt, brace, or garment such as a sock, legging, or shirt. In some embodiments, the sensor module includes: an electrical component configured to undergo a change when the stretchable component is stretched, and a sensor configured to detect the change. The change may include a change in a parameter such as inductance, resistance, or capacitance. In such embodiments, the changed parameter correlates to, and is indicative of, a change in circumference. In some embodiments, the sensor module includes a strain gauge configured to detect a tensile force exerted on the stretchable component, the force being correlated to, and indicative of, a circumference measurement.

In some embodiments, the sensor system is further configured to detect one or more of: a surface skin temperature, an orientation of the body portion, an acceleration of the body portion, and a color of a surface of the body portion. Such a sensor system may include one or more of: a temperature sensor, a gyroscope, an accelerometer, and an image sensor.

In some embodiments, the monitoring system also includes a network computing device communicatively coupled to the mobile computing device and configured to receive and store the measurements (e.g., circumferential, relative positon, position over time, orientation, etc.) and other data received from the mobile computing device, generate and transmit alerts to a healthcare provider or other authorized user, and store and transmit instructions and information to the mobile computing device. In some embodiments, the monitoring system also includes a supervisor computing device communicatively coupled to the network computing device. In some such embodiments, at least some of the instructions and information transmitted from the network computing device to the mobile computing device are customizable by a healthcare provider, coach, or other health or wellness professional via the supervisor computing device.

Another aspect of the present disclosure is directed to a monitoring system for detecting changes to a portion of a body (e.g., circumferential, relative positon, position over time, orientation, etc.). In some embodiments, the monitoring system includes: a sensor system wearable around a portion of an individual's body and configured to obtain measurements for a plurality of parameters of the body portion over a period of time, the plurality of parameters including a circumference of the body portion and one or more of a surface skin temperature, an orientation of the body portion, a position of the body portion, an acceleration of the body portion, and a color of a surface of the body portion; a processor communicatively coupled to the sensor system; and a non-transitory computer-readable medium with instructions stored thereon. The instructions, when executed by the processor, cause the processor to perform a method including: receiving the measurements for the plurality of parameters, applying relative weights to the plurality of parameters to generate weighted measurements, receiving inputs specifying which weighted measurements and one or more additional factors to include in an overall score, the one or more additional factors including one or more of: a compliance score and a user input entered by the individual, calculating the overall score based on the weighted measurements and the one or more additional factors, and generating an alert output when the overall score exceeds a predefined threshold.

In some embodiments, the one or more additional factors further include a range of motion of the body portion. In some embodiments, calculating the range of motion of the body portion includes comparing a first orientation of the body portion to a second orientation of the body portion. In other embodiments, calculating the range of motion of the body portion includes comparing an orientation of the body portion to a first orientation of a first body portion. In some embodiments, the range of motion of the body portion is benchmarked to a previous range of motion reading. In some embodiments, the range of motion of the body portion is compared to a future range of motion goal or a time-based goal. In some embodiments, the future range of motion goal is based on one or more of: an exercise, one or more user-initiated range of motion measurements, and time.

In some embodiments, the method further includes generating a progress indication for the range of motion of the body portion relative to the future range of motion goal.

In some embodiments, the compliance score includes, at least in part, a calculation of a number of repetitions performed of an exercise compared to a prescribed or target number of repetitions. In some embodiments, the calculation of the number of repetitions is based on one or more of: a detected body portion orientation and a detected body portion movement.

In some embodiments, the compliance score includes, at least in part, a calculation of a quality of performance of an exercise. In some embodiments, the calculation of the quality of performance of the exercise is based on one or more of: a detected body portion orientation, a detected body portion movement, a detected body portion circumferential change, and one or more parameters derived from one or more of: the detected body portion orientation, the detected body portion movement, and the detected body portion circumferential change.

In some embodiments, the calculation of the quality of performance is compared to one or more ideal, maximum, or threshold values for the one or more of: the detected body portion orientation, the detected body portion movement, the detected body portion circumferential change, and the one or more parameters.

In some embodiments, the method further includes comparing the measurements for the plurality of parameters to a set of previous measurements for the plurality of parameters.

In some embodiments, the method further includes determining, using the comparison, a range of motion of the body portion. In some embodiments, the method performed further includes determining, using the comparison, a progress of the individual towards a time-based goal, future goal, or target goal for a range of motion of the body portion.

In some embodiments, the method further includes automatically determining a sensor system orientation following placement of the sensor system on the body portion. In some such embodiments, the method includes: positioning the sensor system around the body portion; recommending that the individual perform at least one of: a recommended movement of the body portion and a recommended orientation of the body portion; receiving the measurements of the plurality of parameters during the at least one of the recommended movement and the recommended orientation; and calculating a sensor system orientation based on the measurements of the plurality of parameters.

Another aspect of the present disclosure is directed to a monitoring system for detecting circumferential changes of a portion of a body. In some embodiments, the monitoring system includes: a sensor system wearable on or around a portion of an individual's body and configured to obtain measurements for a plurality of parameters of the body portion over a period of time, the plurality of parameters including one or more of: a circumference of the body portion, a surface skin temperature, an orientation of the body portion, an acceleration of the body portion, a position of the body portion, and a color of a surface of the body portion; a processor communicatively coupled to the sensor system; and a non-transitory computer-readable medium with instructions stored thereon. The instructions, when executed by the processor, cause the processor to perform a method including: receiving the measurements for the plurality of parameters, applying relative weights to the plurality of parameters to generate weighted measurements, calculating an overall score based on the weighted measurements and one or more additional factors, generating an alert output when the overall score exceeds a pre-defined threshold, and transmitting a notification to the individual, such that the notification provides instructions or feedback for improving the overall score.

In some embodiments, the one or more additional factors include one or more of: a compliance score and a user input entered by the individual.

In some embodiments, notifications or feedback are personalized for the individual, such that personalization of the tone is based on one or more of: a demographic, a medical history, an emotional state, a progress, a location, a profile, and the overall score of the individual. In some embodiments, notifications or feedback are customized to a user or patient profile.

In some embodiments, the monitoring system further includes a mobile computing device comprising the processor.

In some embodiments, the feedback includes displaying on a display of the mobile computing device a compliance rating of the individual relative to one or more peers, such that the compliance rating is based on a comparison of the overall score to an expected overall score for the individual. In some embodiments, the feedback includes positive or encouraging messages from one or more of: a caregiver, a healthcare provider, a family member, a friend, or a peer. In some embodiments, the feedback includes a promised monetary or simulated award for improving the overall score. In some embodiments, the feedback includes educational information about one or more long-term effects of the overall score.

In some embodiments, the method further includes transmitting a second notification to one or more of: a caregiver, a healthcare provider, a family member, a friend, or a peer, such that the second notification includes a compliance rating of the individual.

An additional aspect of the disclosure is directed to a leg or arm monitoring device. The leg or arm monitoring device of various embodiments includes: a stretchable component configured to be attached to or fit securely around a circumference of a patient's calf or arm, and a sensor module coupled to the stretchable component. The sensor module includes various electrical components, for example, a battery, a first sensor configured to sense a first parameter indicative of the circumference, rotation, physical performance of the patient's calf or arm during an exercise, a processing unit configured to process the first parameter and detect a measurement from the first parameter, a memory storage configured to store the measurement, and an antenna configured to wirelessly transmit the measurement to a paired mobile computing device.

In some embodiments, the first parameter is selected from a group consisting of: inductance, resistance, capacitance, and strain. In some embodiments, the stretchable component includes a stretchable band, sleeve, belt, brace, or garment. In some embodiments, at least a portion of the sensor module is reversibly coupled to the stretchable component. In some embodiments, the stretchable component is similar to an adhesive as on an adhesive strip or band-aide. In some embodiments, the leg or arm monitoring device is configured to detect swelling of the patient's calf or arm consistent with the performance of a strengthening exercise, onset of interstitial edema, deep vein thrombosis, pulmonary embolism, or lymphedema. In some embodiments, the sensor module additionally or alternatively includes a sensor configured to sense a second parameter indicative of motion of the patient's calf or arm. The sensor may be an accelerometer. Additionally or alternatively, the sensor module may include an additional sensor configured to sense an additional parameter indicative of an orientation of the patient's calf or arm. The additional sensor may be a gyroscope. In some embodiments, the sensor module additionally or alternatively includes one or more of a temperature sensor and an image sensor. In some embodiments, the sensor module is configured to provide a measurement of tightness of the stretchable component. In some embodiments, the leg or arm monitoring device or a mobile computing device communicatively coupled thereto is configured to generate an alert when the sensor module detects that the stretchable component is too tight. In some embodiments, the leg or arm monitoring device generates a haptic alert. In some embodiments, a mobile computing device communicatively coupled to the leg or arm monitoring device is configured to generate outputs that include health-related feedback and/or recommendations based on one or more of the sensor readings.

Another aspect of the present disclosure is directed to a monitoring system for detecting improvement to strength and range of motion for a portion of a body. In some embodiments, the monitoring system includes: a sensor system wearable on or around a portion of an individual's body and configured to obtain measurements for a plurality of parameters of the body portion over a period of time, the plurality of parameters including a performance of body portion in one or more exercises provided as part of an adaptive care plan and one or more of a surface skin temperature, an orientation of the body portion, an acceleration of the body portion, and a color of a surface of the body portion; a processor communicatively coupled to the sensor system; and a non-transitory computer-readable medium with instructions stored thereon. In some embodiments, the instructions, when executed by the processor, cause the processor to perform a method comprising: receiving the measurements for the plurality of parameters, extracting a pattern from the measurements, wherein the pattern comprises a range of motion of the body portion, comparing the pattern to a template or baseline pattern, determining a change in the range of motion of the body portion based on the comparison of the pattern with the baseline pattern, receiving one or more user inputs specifying patient reported inputs, comparing the one or more user inputs to one or more baseline user inputs, determining a change in the one or more user inputs relative to the one or more baseline user inputs, calculating an overall score based on the change in the range of motion and the change in the one or more user inputs, and generating an alert output when the overall score exceeds a predefined threshold.

In some embodiments, the method performed by the processor further comprises measuring one or more planar movements of the body portion to determine the baseline pattern. In some embodiments, the method performed by the processor further comprises determining the baseline pattern using pre-operative planar movements of the body portion. In some embodiments, the method performed by the processor further comprises determining the baseline pattern using pre-operative planar movements of a plurality of body portions of a plurality of individuals. The pre-operative planar movements may be normalized or averaged across the plurality of individuals.

In some embodiments, the method performed by the processor further comprises determining a number of repetitions completed by the body portion. In some embodiments, the method performed by the processor further comprises comparing the number of repetitions to a prescribed number of repetitions to determine whether the prescribed number of repetitions was achieved. In some embodiments, the method performed by the processor further comprises calculating the overall score based on the change in the range of motion, the change in the one or more user inputs, and the number of repetitions.

In some embodiments, the patient reported inputs comprise one or more of: symptoms, pain level, subjective statements on mobility, medication adherence, emotional state, attitude towards recovery, a duration of sleep attained, a food consumed, a daily wellness rating, a supplement consumed, risk factor data, and any combination thereof. In some embodiments, the patient reported inputs comprise patient self-reports including one or more of: pain level, daily activities, symptoms, and subjective statements on mobility.

In some embodiments, the plurality of parameters comprise patient generated health data, and the monitoring system is configured to dynamically adjust a prediction and generate a simulation that is used to improve patient adherence to an adaptive care plan.

In some embodiments, the overall score comprises an overall adherence and recovery score based on patient generated heath data or the patient reported inputs, and wherein the patient generated health data comprises one or more of: the range of motion, reduction in pain, improvement in gait, strength improvement, stability improvement, and a combination thereof.

In some embodiments, the plurality of parameters further comprises a measure of quality of performance of the one or more exercises, and wherein feedback regarding the quality of performance is assessed dynamically and provided to the patient in real-time. In some embodiments, the quality of performance of the one or more exercises comprises one or more of: a measure of flexibility, a measure of strength, a measure of endurance, a measure of timing, a measure of smoothness of movement, a measure of shakiness of movement, positional information, relative fatigue levels, a measure of speed of movement, and a combination thereof.

In some embodiments, the alert output is generated depending on one or more inputs provided by the user, wherein the processor assesses the probability of the user adhering to a care protocol and simulates multiple alert outputs, such that a generated alert output is provided to the user based on the one or more simulated outputs.

In some embodiments, the instructions stored on the computer-readable medium further cause the processor to query the individual for the one or more user inputs. In some embodiments, the one or more user inputs comprise an indication of whether the individual has complied with a prescribed instruction.

In some embodiments, the sensor system comprises an adhesive component and a sensor module coupled thereto, wherein the adhesive component is configured for use for a predefined fixed interval before replacement.

In some embodiments, the body portion comprises a limb, upper torso, or lower torso. In some embodiments, the body portion comprises a right leg and a left leg of the individual, and wherein the sensor system comprises: a first component configured to obtain a plurality of positional and orientational measurements over time from a fixed location on the right leg, and a second component configured to provide auditory feedback to the patient in real-time, based on performance of the user as measured by the sensory system.

In some embodiments, processing the positional and orientational measurements to identify and analyze a change comprises one or more of: comparing the plurality of positional and orientational measurements to detect a change in the adherence of a user to an adaptive care plan or the probability of complete recovery by a particular time.

In some embodiments, an overall score is calculated by the processor based at least in part on measurement of the body portion and one or more user-entered inputs related to symptoms or risk factors. In some embodiments, the overall score is further based on a measure of compliance with prescribed instructions, the measure of compliance determined from one or more of: a detected body portion orientation, a detected body portion movement, and a user-entered input related to compliance.

In some embodiments, the one or more exercises comprise flexion, extension, abduction, adduction, or a combination thereof.

In some embodiments, the method performed by the processor further comprises transmitting a notification to the individual, wherein the notification provides instructions or feedback for improving the overall score. In some embodiments, a tone of the notification or feedback is personalized for the individual, wherein personalization of the tone is based on one or more of: a demographic, number of sessions completed, number of sessions missed, goals achieved, previous response to motivation messages and notifications, pain level, a medical history, an emotional state, calculated probability of attending session next day, simulated scenario of actions taken by the patient, a progress, a location, a profile, and the overall score of the individual. In some embodiments, the feedback comprises displaying on a display of the mobile computing device a compliance rating of the individual relative to one or more peers, wherein the compliance rating is based on a comparison of the overall score to an expected overall score for the individual. In some embodiments, the feedback comprises positive or encouraging messages from one or more of: a caregiver, a healthcare provider, a family member, a friend, or a peer.

In some embodiments, the method performed by the processor further comprises transmitting a second notification to one or more of: a caregiver, a healthcare provider, a family member, a friend, or a peer, wherein the second notification includes a compliance rating of the individual. In some embodiments, the feedback comprises a promised monetary or simulated award for improving the overall score. In some embodiments, the feedback comprises educational information about one or more long-term effects of the overall score.

Another aspect of the present disclosure is directed to a leg monitoring device. In some embodiments, the device comprises a component configured to attach securely to a patient's leg or arm; and a sensor module coupled to the component, wherein the sensor module comprises: a battery, a first sensor configured to sense a first parameter indicative of the position and orientation of the patient's leg or arm, and wherein the sensor module comprises: a first component configured to obtain a plurality of positional and orientational measurements over time from the position and orientation of the patient's leg or arm, and a voice-enabled component configured to provide auditory feedback to the patient in real-time, based on performance of the user as measured by the sensory module, a processing unit configured to process the first parameter and detect a position and orientation measurement from the first parameter, a memory storage configured to store the position and orientation measurements, and an antenna configured to wirelessly transmit the position and orientation measurements to a paired mobile computing device.

In some embodiments, the first parameter is selected from a group consisting of: inductance, resistance, magnetism, and capacitance. In some embodiments, the component comprises a stretchable band, sleeve, belt, brace, or garment. In some embodiments, at least a portion of the sensor module is reversibly coupled to the component.

In some embodiments, the leg monitoring device is configured to assesses the probability of the user adhering to a care protocol and simulates multiple alert outputs, such that a generated alert output is provided to the user based on the one or more simulated outputs.

In some embodiments, the sensor module further comprises a second sensor configured to sense a second parameter indicative of motion of the patient's leg or arm.

In some embodiments, the second sensor is an accelerometer or magnetometer. In some embodiments, the sensor module further comprises a third sensor configured to sense a third parameter indicative of a circumference of the patient's leg or arm. In some embodiments, the third sensor is a gyroscope or magnetometer. In some embodiments, the sensor module further comprises one or more of a temperature sensor and an image sensor. In some embodiments, the sensor module is configured to provide a measurement of tightness of the component.

BRIEF DESCRIPTION OF THE DRAWINGS

The foregoing is a summary, and thus, necessarily limited in detail. The above-mentioned aspects, as well as other aspects, features, and advantages of the present technology will now be described in connection with various embodiments, with reference made to the following accompanying drawings:

FIG. 14A-14E illustrates exemplary computational aspects of the system including features of the system and methods for model analysis.

Figure 1A:
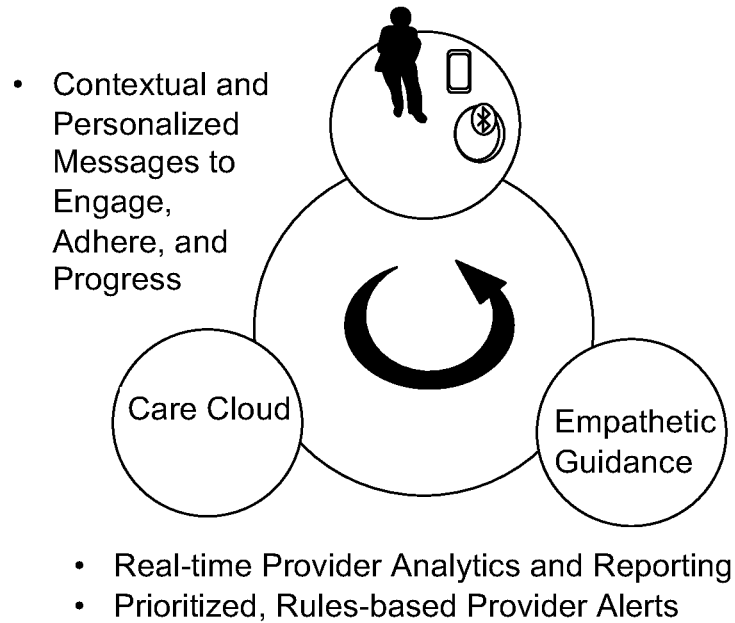
FIG. 1A illustrates an exemplary overview of interactive components of the monitoring system.

The illustrated embodiments are merely examples and are not intended to limit the invention.

DETAILED DESCRIPTION

The following description is not intended to limit the invention to these described embodiments, but rather to enable any person skilled in the art to make and use this invention. Other embodiments may be utilized and modifications may be made without departing from the spirit or the scope of the subject matter presented herein. Aspects of the disclosure, as described and illustrated herein, can be arranged, combined, and designed in a variety of different configurations, all of which are explicitly contemplated and form part of this disclosure.

Throughout and within this specification, one or more publications may be referenced to more fully describe the state of the art. The disclosures of each of these references are incorporated herein by reference in their entireties as though they also form part of this disclosure.

Unless otherwise defined, each technical or scientific term used herein has the same meaning as commonly understood by one of ordinary skill in the art to which this disclosure belongs.

As used in the description and claims, the singular form "a", "an" and "the" include both singular and plural references unless the context clearly dictates otherwise. For example, the term "a limb" may include, and is contemplated to include, a plurality of limbs. At times, the claims and disclosure may include terms such as "a plurality," "one or more," or "at least one;" however, the absence of such terms is not intended to mean, and should not be interpreted to mean, that a plurality is not conceived.

The term "about" or "approximately," when used before a numerical designation or range (e.g., a change in force or circumference), indicates approximations which may vary, for example, by (+) or (−) 5%. All numerical ranges provided herein are inclusive of the stated start and end numbers. The term "substantially" indicates mostly (i.e., greater than 50%) or essentially all of an element, process, component, device, or system.

As used herein, the term "comprising" or "comprises" is intended to mean that the devices, systems, and methods include the recited elements, and may additionally include any other elements. "Consisting essentially of" shall mean that the devices, systems, and methods include the recited elements and exclude other elements of essential significance to the combination for the stated purpose. Thus, a system or method consisting essentially of the elements as defined herein would not exclude other materials, features, or steps that do not materially affect the basic and novel characteristic(s) of the claimed invention. "Consisting of" shall mean that the devices, systems, and methods include the recited elements and exclude anything more than a trivial or inconsequential element or step. Embodiments defined by each of these transitional terms are within the scope of this disclosure.

Overview

Disclosed herein are devices, systems, and methods for a providing a unified care system for adaptively improving the musculoskeletal performance of a user (e.g., patient, athlete, etc.). A unified monitoring system as disclosed herein comprises: adaptable content provided to the user, sensors for use by the user outside of a supervised medical facility, a care cloud comprising systems and devices for collecting meaningful recovery data from sensors used by the user and from information provided by the user, and communication tools that facilitate and broker timely communication between healthcare providers, the user's support network (e.g., family, friends, home care providers, etc.) and the user. Disclosed herein are also devices, systems, and methods for monitoring one or more health parameters of an individual, including gait, movement (e.g., movement of body portion relative to gravitational direction and position), orientation, and circumferential changes to one or more body portions. The devices, systems, and methods of various embodiments are additionally intended to track and increase compliance with health and wellness recommendations and improve health and wellness outcomes.

FIG. 1A illustrates various data-based feedback loops that are involved in gathering data. Data-based feedback include patient reported outcome (PRO), patient-generated health data (PGHD), and real-time feedback to the patient and care providers and caregivers as needed to guide patients through recovery. PRO data comprises patient self-reports about their recovery including symptoms, pain level, subjective statements on mobility, etc. PGHD data comprises automatically generated data about the patient from the sensors. As shown in FIG. 1A, the monitoring system manages three components: the sensor/device that are used by the patient, the care cloud that collects/stores/analyzes data collected from the sensor and from patient feedback, and the healthcare/caregiver/support teams that provide empathetic guidance and support to the user/patient. The monitoring system does this by providing contextual and personalized messages to engage, adhere, and progress the patient through their care plan. The monitoring system also provides real-time provider analytics and reports such that the care team and healthcare providers may efficiently and effectively respond to the needs of the patient. Finally, the monitoring system provides priorities and rules-based provider alerts that may help providers efficiently manage their time and user/patient care.

Figure 1B:
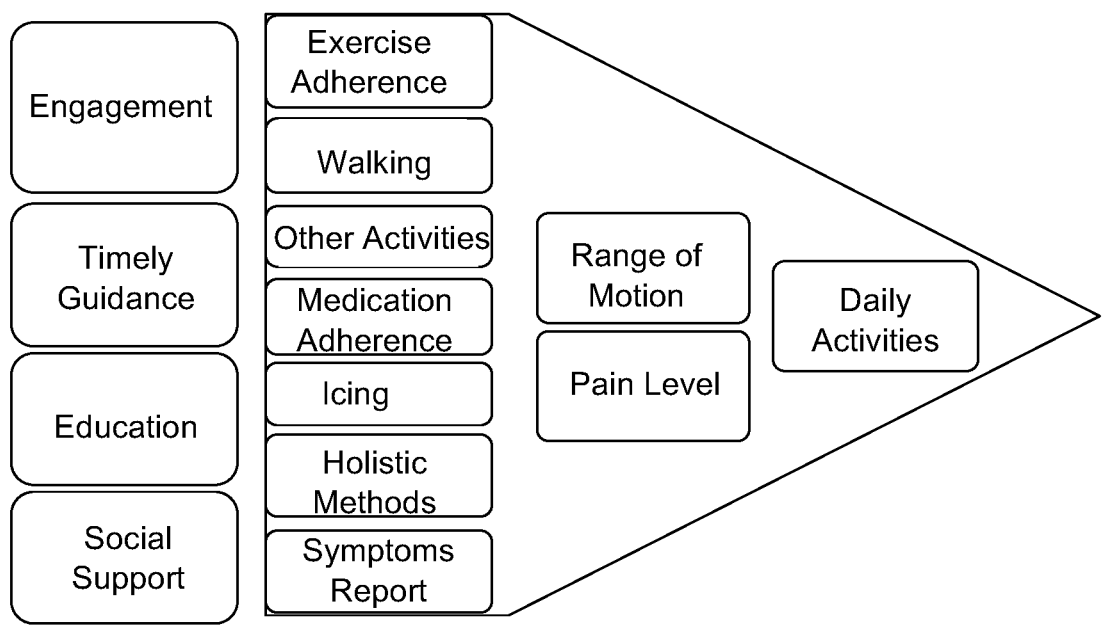
FIG. 1B illustrates the elements and/or adaptive aspects of the patient notification system.

FIG. 1B illustrates various clinical and social aspects of healthcare that are integrated into the monitoring system using the sensor, application, and care cloud model to improve patient outcomes and get patients back to their daily routines. The system provides the key features of engagement, timely guidance, education, and social support. Engagement with the user/patient helps to facilitate exercise adherence and walking, while the timely guidance supports other activities and medical adherence. The education component provides users with insight into methods for helping the user heal faster including methods for icing and holistic methods. Finally, the application provides social support, which allows the user's symptoms to be reported to the system and for the system to broker interactions between the user/patient and their care team. Collectively, these aspects help to improve the metrics that are monitored by the system, which include the range of motion of the user/patient, their pain levels and their daily activities, such that the user/patient may easily and quickly recover efficiently and produce good clinical outcomes.

Figure 1C:
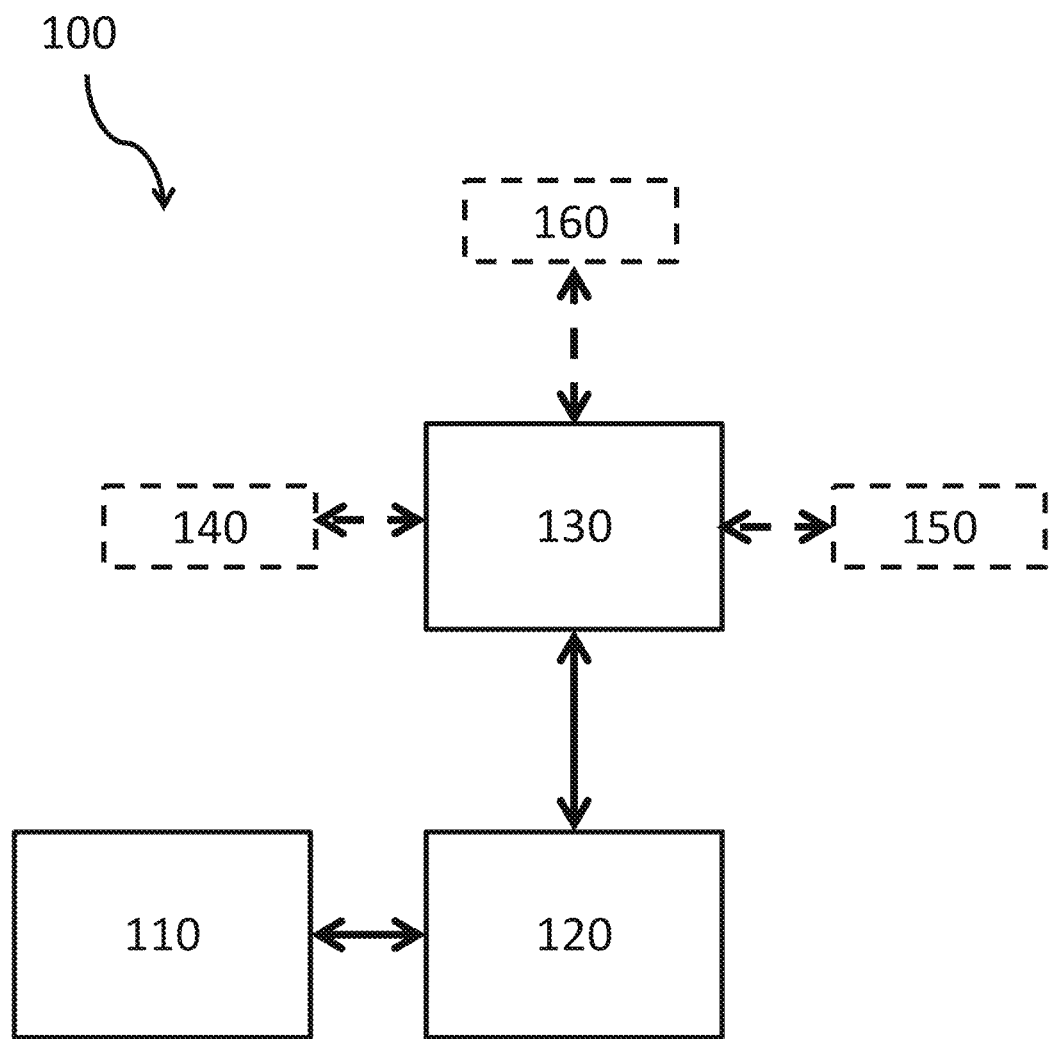
FIG. 1C illustrates a schematic block diagram of one embodiment of a system for monitoring health parameters of an individual, including circumferential changes to a portion of a body.

FIG. 1C illustrates one example of a health monitoring system (e.g., system comprising care cloud, patient profile generators, adaptive patient user interfaces, sensors, healthcare interfaces, support team communications, etc.) configured to obtain, analyze, and respond to positional, orientational, and circumferential measurements of a body portion of an individual. As illustrated, the monitoring system 100 includes a sensor system 110, a mobile computing device 120, and a network computing device 130. The system 100 may additionally be configured to form a connected network in which physicians, coaches, and/or other authorized users can track the progress of the monitored individual and/or individualize instructions and feedback provided to the monitored individual. In such embodiments, the health monitoring system 100 includes one or more additional computing devices, including one or more supervisor computing devices 140, one or more reviewer computing devices 150, and/or one or more administrator computing devices 160.

In various embodiments, the sensor system 110 is configured to be worn by a subject. A subject who wears the sensor systems described herein may be interchangeably referred to as a user, patient, individual, person, or athlete. It will be appreciated by those skilled in the art that the subject monitored by the various devices and systems described herein may be any mammal or other animal.

The sensor system 110 may be formed of: a stretchable component configured to fit securely on or around a body portion of the individual, and a sensor module coupled thereto. The stretchable component may be a strap, brace, belt, garment, adhesive bandage, or other wearable material designed to be attached to or fitted around the body portion. As used herein, the body portion may refer to one or both legs, one or both arms, a torso, a chest, a belly, a waist, a head, and/or other body part. The sensor module may be configured to sense the amount of stretch experienced by the stretchable component, the quality, frequency, duration, or other characteristic of movement and/or detect a circumference measurement from a sensed stretch.

In various embodiments, the sensor system 110 may comprise one or more magnetic components that are adhered to the body portions. In some embodiments, sensors may use a magnetic mounting system so that localized body motion, orientation, circumferential width increase, and localized temperature variations may be detected. In some embodiments, the magnet is inside the sensor and attached to a magnetized adhesive strip which may be placed anywhere on the body.

The sensor module may be configured to measure one or more aspects of a body portion relative to gravity. The sensor module may comprise a single sensor, dual sensors, or greater than two sensors. The sensor module may be configured to monitor the speed, time, and/or smoothness of the movement of the body portion. In various configurations, the sensor module may be configured such that it may rely on magnetic readings. In further embodiments, a sensor may be configured to perform magnetic readings relative to gravity, and may detect twisting motion, vibrating motion, and changes in orientation relative to the X, Y, and/or Z planes. As used herein, the sensor module includes all sensors, power supply, signal processing electronics, controlling logic, and digital transmission devices needed to sense movement, orientation, or stretch, obtain measurements of the body portion or body portions, and transmit the measurements to the mobile computing device 120. The sensor module may additionally include other sensors such as sensors configured to detect orientation, acceleration, temperature, and/or color.

As used herein, the mobile computing device 120 refers to both the hardware and the application software of the computing device that communicates with the sensor system 110. The mobile computing device 120 is configured to receive, process, and analyze sensor data from the sensor system 110. It may be further configured to adaptively query an individual for user inputs, generate reminders and other alerts to the individual, provide access to relevant health-related information, and generate and transmit messages intended for physicians, coaches, caregivers, or other authorized users of the system. Queries to a user may be customized to a user profile and/or one or more distinct characteristics of the patient or user including but not limited to: the number of sessions completed by a patient, the number of sessions missed by a patient, goals achieved by a patient, response to previous messages provided by monitoring system, and/or pain level.

In some embodiments, the mobile computing device 120 is a smartphone, wearable computing device, notebook computer, laptop computer, tablet, or other portable computing device configured to pair with the sensor system 110. In other embodiments, the mobile computing device 120 may be any other personal computing device configured for wired or wireless connection to the sensor system 110.

As shown in FIG. 1C, the mobile computing device 120 is connected, at least at times, to the sensor system 110 via a communication link. In some embodiments, the mobile computing device 120 is wirelessly coupled to the sensor system 110 via a nearfield communications (NFC) protocol, a low energy Bluetooth® protocol, or other radiofrequency (RF) communication protocol. In some embodiments, the sensor system 110 is additionally or alternatively configured to communicate with the mobile computing device 120 via a databus and a wired (e.g., removable cable) connection. In some embodiments, communication between the sensor system 110 and the mobile computing device 120 is bidirectional; in other embodiments, communication is unidirectional with data pushed from the sensor system 110 to the mobile computing device 120.

In various embodiments, the mobile computing device 120 is coupled to the network computing device 130 via a bidirectional communication link. In particular, the mobile computing device 120 may be connected to the network computing device 130 via a CDMA, GSM, LTE, or other cellular network, via Wi-Fi®, or via any other suitable wireless or wired communication protocol. If one or more supervisor computing devices 140, reviewer computing devices 150, and/or administrator computing devices 160 are present in the system, such devices are also connected to the network computing device 130 via a bidirectional communication link, such as a cellular network, Wi-Fi, other wireless communication protocol, or via a cable internet, dial-up internet, Ethernet, or other wired means of connection.

The network computing device 130 of some embodiments is a cloud-based server (e.g., care cloud). It may be formed of one or multiple computing devices, including an application server, an internet server, a database server, or a combination thereof. In some embodiments, the network computing device 130 is operated, managed, controlled, maintained, or owned by a system administrator. The network computing device 130 refers to the hardware and software that contains and implements an analytics system. The analytics system refers to the backend system that stores all user data. It also stores all instructions that are transmitted to and downloadable by the mobile computing device 120. These include application instructions (i.e., software) and prescribed health-related instructions intended for the monitored individual. The analytics system of some embodiments is also configured to perform analytics of a monitored individual's data and population-wide data. The analytics system may also be configured for integration with electronic medical records.

In various embodiments, a cloud-based server or care cloud may comprise a cloud based content management and storage system, configured as a central intelligence for the monitoring system. A care cloud may be configured with comprehensive knowledge about a user's (e.g., patient's) current state and historic state. A care cloud may collect information and intelligence about patients across providers and, using the collected information, may generate deductions, modification, refinements, etc. to care plans. A care cloud may correlate data elements to track and improve care delivery and adherence for a single patient and for groups of patients.

In some embodiments, one or more supervisor computing devices 140 are provided within the monitoring system. As used herein, a supervisor computing device 140 is any computing device used by a health or wellness professional to interact with the analytics system of the network computing device 130. As used herein, a health or wellness professional and/or healthcare provider is also referred to as a supervisor and is intended to include any individual who oversees an aspect of the care, health, or wellness of the monitored individual. The supervisor may be, for example, an athletic coach, personal trainer, or healthcare provider. A healthcare provider, as used herein, refers to a professional responsible for the healthcare of the monitored individual. The healthcare provider may be a physician, physician assistant, medical technologist, other medical assistant, nurse, nurse practitioner, podiatrist, chiropractor, dietician, midwife, obstetrician, or any other healthcare professional. In some embodiments, a supervisor is able to access an application-based or web-based internet portal using the supervisor computing device 140, which enables the supervisor to interact with the analytics system of the network computing device 130. Through the supervisor portal, the supervisor can: review data acquired from the sensor system 110; configure and modify alert algorithms, which the monitoring system uses to determine when to generate alerts (e.g., for the monitored individual, healthcare providers, care providers or others) and what alerts to generate; create, customize, and/or modify prescribed instructions for the monitored individual; select specific parameters for the sensor system 110 to monitor; select specific parameters and/or measurements for inclusion in an overall score for the monitored individual; and select or compose messages for transmission to the mobile computing device 120 of the monitored individual and/or other approved users or reviewers.

Additionally or alternatively, in some embodiments, one or more reviewer computing devices 150 are provided within the monitoring system. As used herein, a reviewer computing device 150 is any computing device used by a reviewer to interact with the analytics system of the network computing device 130. As used herein, a reviewer is any trusted individual who has been granted access, by a monitored individual or a supervisor, to review the data of a particular monitored individual. The reviewer may be a caregiver, friend, family member, guardian, or other individual concerned with the welfare of the monitored individual. In some embodiments, a reviewer is able to access an application-based or web-based internet portal using the reviewer computing device 150, which enables the reviewer to interact with the analytics system of the network computing device 130. In some embodiments, a supervisor or reviewer may use a healthcare provider interface to access, review, or interact with the analytics system of the network computing device 130. Through the reviewer portal, the reviewer may be able to: review all or a limited portion of the data acquired from the sensor system 110; select or compose messages of encouragement or other feedback for transmission to the mobile computing device 120 of the monitored individual; and/or generate and send questions to a healthcare provider or other supervisor.

The network computing device 130 may include one or more input devices, output devices, and/or communicatively coupled administrator computing devices 160 through which a system administrator can create and maintain the analytics system.

Each of the supervisor computing devices 140, reviewer computing devices 150, and administrator computing devices 160 may be any suitable computing device, including, for example, a smartphone, wearable computing device, notebook computer, laptop computer, tablet, or desktop computer.

Together, the components of the monitoring system 100 function to execute various algorithms and perform various methods, including obtaining, analyzing, and responding to measurements (e.g., circumferential, positional, relational, orientational, smoothness, etc.) of a body portion.

Figure 2:
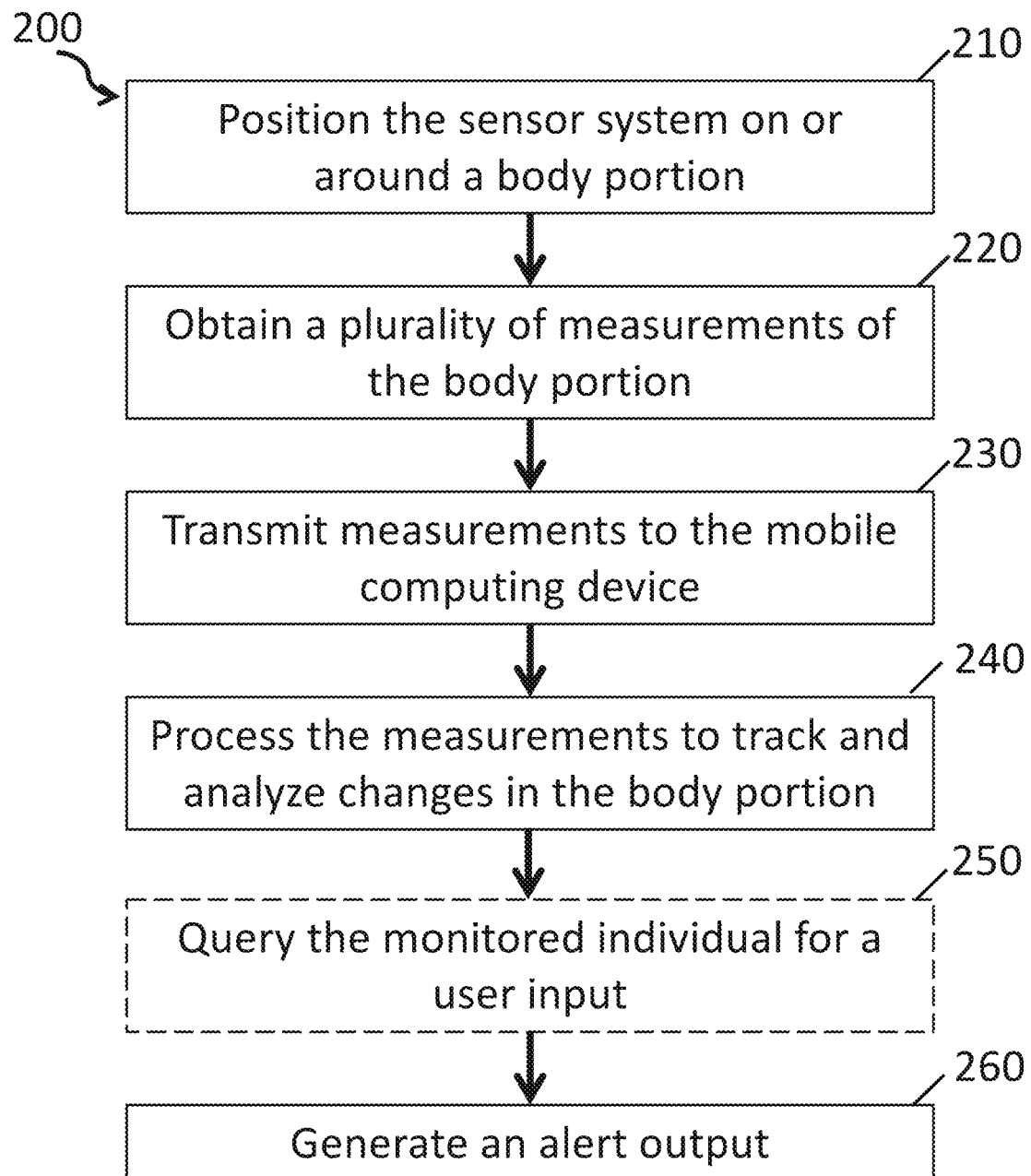
FIG. 2 illustrates a flow chart of one embodiment of a method of using the monitoring system of FIG. 1C.

FIG. 2 depicts one example of a method 200 of using the monitoring system 100 described above. As shown at block 210, the method includes positioning the sensor system 110 on or around a body portion. The sensor system 110 may be secured on or around the body portion by the monitored individual or with the help of a physician, athletic trainer, other supervisor, friend, family, caregiver, or other reviewer. The sensor system 110 of some embodiments may be reusable and configured to permit repeated attachment to and detachment from the body portion. In some embodiments, the sensor system 110 is shaped to conform to one or more contours of the individual's body or is otherwise configured so as to facilitate accurate positioning of the sensor system 110 at the same location each time it is worn. In some embodiments, the sensor system may be disposable. A sensor system may be adhered to the body portion by an adhesive. A sensor system may be configured to stretch or adapt to the movement or contours of the body portion during performance of an activity.

As shown at block 220, the method 200 further includes obtaining a plurality of measurements of the body portion via the sensor system 110, including, for example, a plurality of positional, orientational, and/or circumferential measurements. As described in more detail in the next section, in some embodiments, obtaining the plurality of measurements includes: obtaining a baseline, sensing a change in a parameter indicative of and correlated to a change in the measurement (e.g., circumferential, positional, relational, orientational, smoothness, etc.), and calculating a measurement from the sensed change in the parameter. The calculated measurement (e.g., circumferential, positional, relational, orientational, smoothness, etc.) may be a relative measurement (i.e., a measure of change from the baseline or from a previous measurement) or an absolute measurement. In some embodiments, obtaining a plurality of measurements (e.g., circumferential, positional, relational, orientational, smoothness, etc.) of the body portion further includes obtaining measurements (e.g., absolute or relative measurements) of one or more additional health-related parameters. For example, in some embodiments, the sensor system 110 is configured to obtain measurements indicative of one or more of a change in: orientation, movement (i.e., acceleration), color, and temperature of the body portion. Additionally or alternatively, in some embodiments, the sensor system 110 is configured to obtain measurements indicative of pulse, heart rate, blood oxygenation (i.e., pulse oximetry), blood volume (i.e., plethysmography), range of motion as described elsewhere herein, and/or other health parameters.

The method 200 also involves transmitting the measurements from the sensor system 110 to a communicatively coupled mobile computing device 120 or other computing device, as shown at block 230. The transmitted measurements may include any obtained by the sensor system 110, including, for example, circumference, orientation, acceleration, color, and/or temperature.

At block 240, the measurements are processed to track and analyze changes in the body portion. In some embodiments, measurements (e.g., circumferential, positional, relational, orientational, smoothness, etc.) are tracked over time and changes are analyzed, for example, to determine when the change (e.g., circumferential, positional, relational, orientational, smoothness, etc.) has exceeded a predefined threshold value. Similarly, any other parameters being measured may be tracked over time and analyzed, for example orientation or acceleration is tracked over time to determine a range of motion of the body portion. In some embodiments, each measured parameter contributes to an overall risk score or wellness score, and analyzing the measurements involves weighting the changes in each parameter, calculating an overall score, and determining if the score has exceeded a predefined threshold value. In some embodiments, processing the measurements to track and analyze changes is performed partially or fully by the mobile computing device 120. Additionally or alternatively, in some embodiments, some of or all the processing, tracking, and analysis is performed on the sensor system 110. Additionally or alternatively, in some embodiments, some of or all the processing, tracking, and analysis is performed by a network computing device 130.

Optionally, in some embodiments, the method 200 further includes querying the individual for user inputs, as shown at block 250. Such queries are presented to a monitored individual on the mobile computing device 120. The requested user inputs may vary depending on the intended use of the monitoring system 100. For example, the mobile computing device 120 may prompt a user to enter one or more of: current pain level, emotional state, attitude towards recovery, time with family or friends, daily activities (e.g., chores, television watching, reading, etc.), biographical information; the user's current weight, age, and/or height; medical history; family medical history; current symptoms; risk factor data; a pregnancy status (e.g., a gestation age, conception date, pre-mature birth risk factors, or due date); an exercise performed; a food consumed; a supplement consumed; a medication administered; a duration of sleep attained; a daily wellness rating; and an indication of whether the monitored individual has complied with a prescribed instruction or exercise.

The monitoring system 100 generates an alert output at block 260. The alert output may be a visual, tactile, and/or audio output generated by the mobile computing device 120. The alert output may provide a warning, recommendation, positive feedback, progress alert, or any other useful message. The alert output is based, at least in part, on the analyzed change in position, orientation, and/or circumference. Alternatively, the alert output is based, at least in part, on the analyzed change in one or more measured parameters or a change in range of motion of the body portion. For example, the alert output may be generated by the mobile computing device 120 upon detecting that the change (e.g., circumferential, positional, relational, orientational, smoothness, etc.) exceeded a predefined threshold. In other embodiments, the alert output is generated by the mobile computing device 120 at a regular time interval, and the information conveyed in the alert output varies depending on the body portion's change (e.g., positional, shaking, circumferential, orientational, range of motion, extension, etc.). In some embodiments, the alert output may also be based, in part, on the analysis of other parameters being measured and/or the user inputs. In some embodiments, alert outputs may also be transmitted to one or more supervisor and/or reviewer computing devices to alert a supervisor or reviewer of important changes, progress, or status of the monitored individual.

Figure 10:
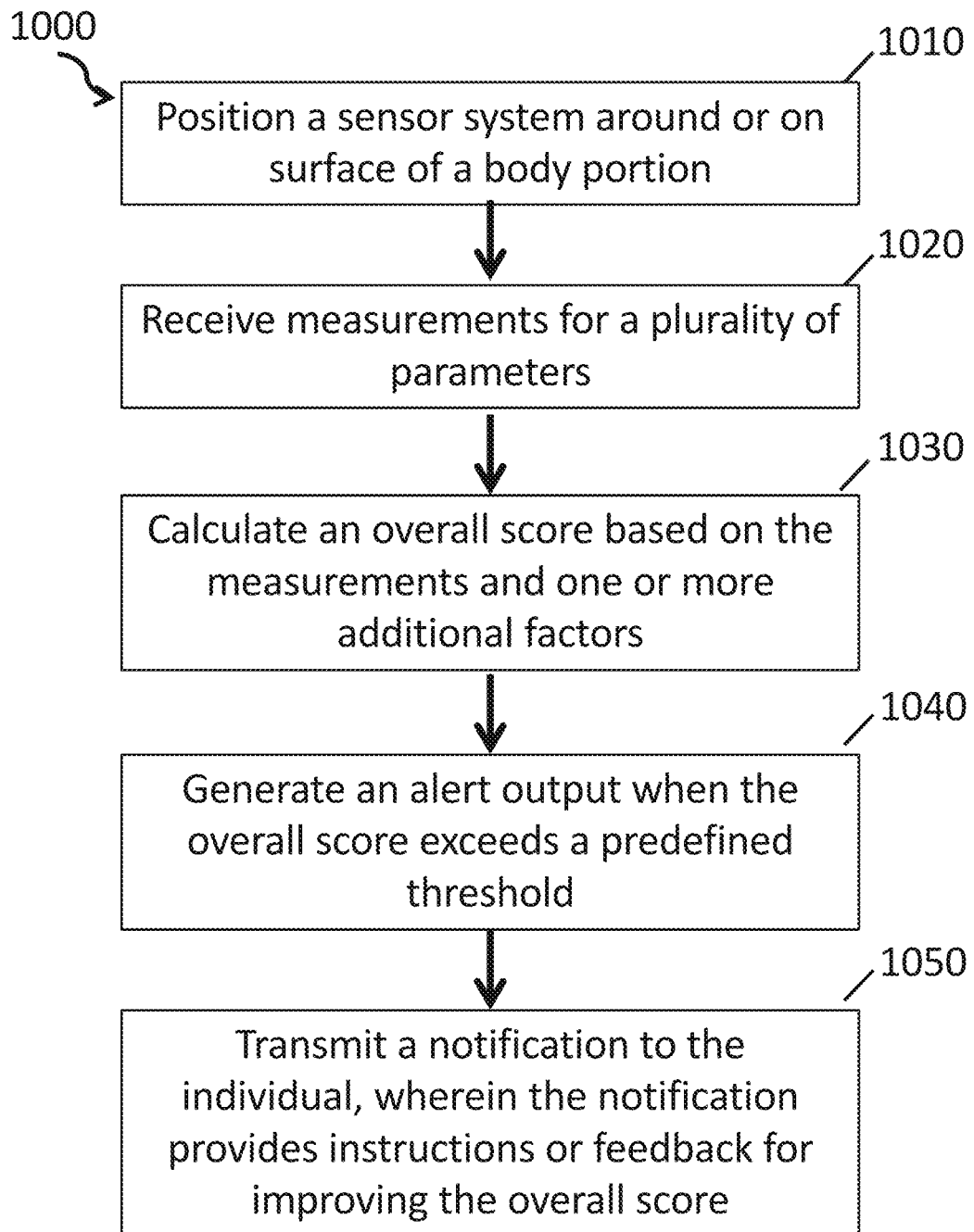
FIG. 10 illustrates a flow chart of one embodiment of a method for providing instructions or feedback for improving an overall score.
Figure 11:
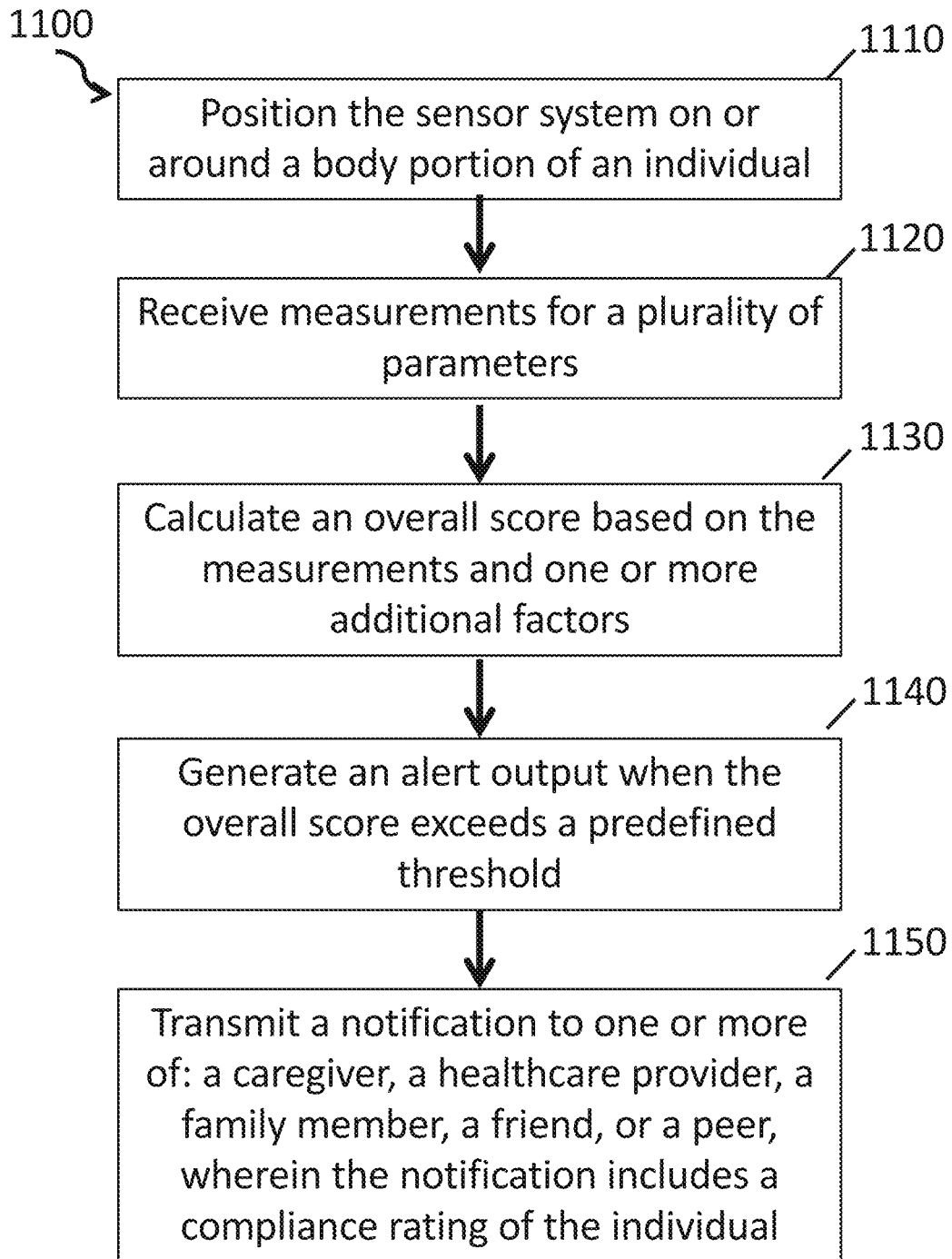
FIG. 11 illustrates a flow chart of one embodiment of a method for transmitting a notification about a compliance rating of an individual.

FIGS. 10 and 11 depict another example of a method 1000 and 1100, respectively, of using the monitoring system 100 described above. As shown at blocks 1010/1110 and 1020/1120, the method includes positioning a sensor system on or around a body portion and receiving measurements for a plurality of parameters, as described elsewhere herein. At blocks 1030/1130, the method includes calculating an overall score based on the measurements and one or more additional factors.

The overall score may be an overall risk score or wellness score. In some embodiments, the overall score corresponds to a likelihood of onset of a disease that causes abnormal swelling of a limb. For example, the overall score may correspond to the likelihood that the monitored individual will recover from an operation or procedure and regain strength, coordination, balance, range of motion, or other metric of improvement. In some instances, the overall score may indicate the successful completion and physical rehabilitation of a patient by a certain date or within a certain time period or range.

As another example, the overall score may correspond to a monitored individual's level of success in improving overall wellness and/or adherence to a prescribed care plan. Such a score may be applicable, for example, when the monitoring system is being used to track gradual changes (e.g., circumferential, positional, orientational, relational, smoothness, etc.) of a body portion, for example those associated with improved musculoskeletal performance, range of motion, weight gain, weight loss, a growing fetus, or an increase in muscle mass. Such a system may be used, for example, by individuals who are overweight, underweight, being treated for cancer, pregnant, or athletes. One, some, or all the measured parameters may contribute to the overall score, including one or more of: the change in circumference of the body portion, a skin temperature at the body portion, a skin color at the body portion, and quality or range of movement of the body portion, pain level, medication and physical therapy adherence.

In some embodiments, the overall score may comprise an overall adherence and recovery score, indicating the likelihood that a patient will successfully recover to an acceptable standard. An acceptable standard may be defined based on range of motion, reduction in pain, improvement in gait, strength/stability improvement, or other factors. An acceptable standard may be based on a prescribed care plan and a baseline performance, for example, prior to a medical procedure. An overall adherence score may be generated based on one or more of the following: the quality of the performance of a prescribed exercise, improvements of range of motion, changes in pain level, adherence to medications, adherence to prescribed exercises, etc. Quality of performance of exercises can comprise one or more of: the flexibility, strength, and/or endurance of an exercise, for example, joint extension measured by the one or more sensors. The one or more sensors may be configured to track the timing, smoothness, shakiness, positional information, relative fatigue levels—for example measurements taken over a set of repetitions, performance across days, and any other measures disclosed herein.

In some embodiments, calculating an overall score includes assigning a value to each measurement of each parameter and summing the values to create an overall score. For example, a bicep with a circumference between 0-5 inches may be assigned a value of 1, between 6-10 inches a value of 2, 11-15 inches a value of 3, and 16-20 inches a value of 4 and a skin temperature between 96-99° F. may be assigned a value of 1 and 100-103° F. may be assigned a value of 2. An individual having an overall score of 2 or 3 may be deemed as "normal" or healthy whereas an individual with a score of 4 or 5 may be deemed as unhealthy or requiring medical attention. In other embodiments, an overall score is calculated by assigning a relative weight to one or more measured parameters of importance. In further embodiments, weights used to calculate an overall score can be adapted over time based on PRO data, reported by the patient when the patient enters a response to a question or survey or log; PGHD data, generated automatically by sensors; data provided by a supervisor or healthcare provider; and/or input received from the patients support network or home care providers. In some embodiments, a processor of the mobile computing device calculates an overall score; in other embodiments, a sensor module, a supervisor computing device, a healthcare provider computing device or system, a reviewer computing device, or a network computing device calculates the overall score.

For example, arithmetic average of a sliding window of movement data streaming from the sensor can be done on the sensor itself. Further, similarly multiplying precomputed weights to streaming data can be done on the sensor, but calculating the weights itself requires more processing power. Algebraic computation, such as Fourier transform, may need at least the mobile computing device. Heavier computations such as using machine learning on the same on data may be performed using the processing power of the server.

At blocks 1040/1140, the method includes generating an alert output when the overall score exceeds a predefined threshold, as described elsewhere herein. In some embodiments, the predefined threshold is a personalized threshold based on historical tracking of the user. For example, the initial measurements of joint extension of an individual may indicate a baseline range of motion of 60% of ideal range of motion with significant shaking. As such, in some embodiments, the system outputs an alert when the overall score indicates that the joint extension has dropped below the baseline (e.g., indicative of regress or degeneration) or surpassed the baseline (e.g., indicative of progress and recovery). In other embodiments, the predefined threshold is based on population metrics or collected population data. Such population metrics may be skewed towards a demographic of the individual or patient. In still other embodiments, the predefined threshold is based on known healthy or unhealthy ranges for each of the parameters, for example based on empirical evidence.

At block 1050, the method includes transmitting a notification to the individual or a caregiver, healthcare provider, family member, friend, and/or peer of the individual. A notification may be transmitted to groups of individuals, for example a care team selected by and curated by the user. The notification provides instructions or feedback for improving the overall score of the individual or achieving a pre-determined or target overall score. In some embodiments, the feedback includes positive or encouraging messages from a caregiver, healthcare provider, family member, friend, and/or peer. Alternatively or additionally, the feedback includes a promised monetary or material award or a simulated award for improving the overall score or achieving a pre-determined or target overall score. For example, a promised monetary award is a gift card, a gift certificate, cash, other award, or points or cash-back for use in a marketplace. The marketplace may be sponsored by a healthcare provider, an insurance provider, a third-party service, or a seller or distributor of the monitoring system. Non-limiting examples of material awards include items selected by the individual from a marketplace, consumer products, music-related products, kitchen-related products, exercise-related products, health-related products, work-related products, leisure-related products, or any other material asset, item, or product. Non-limiting examples of simulated awards include: lives for a cartoon or simulated character; coins, treats, cash, turns, or other incentives for use in a simulated world or game; acceleration or fast-forwarding to a more advanced level of a game; an increased overall ranking in a simulated world or game; or any other virtual or simulated award.

In some embodiments, the feedback includes educational information about one or more long-term effects of the overall score. For example, the system may compile and analyze a series of observations or measurements from the individual and project a percent or other value indicative of range of motion (e.g., passive, active, active-assisted) that the individual can expect to lose or secondary health conditions the individual may acquire if the individual continues down this path. Various parameters that the system analyzes include, but are not limited to: exercise frequency, adherence to a dosing regimen for one or more prescriptions, adherence to prescribed exercises (e.g., quality and quantity), measured parameters from one or more sensors, adherence to a recommended diet, adherence to a visitation schedule with a healthcare provider, and/or any additional parameters.

The instructions may include messages from a caregiver or a healthcare provider about athletic exercises, eating parameters, dieting regimens, sleeping regimens, pharmaceutical prescriptions or dosings, or other wellbeing activities or exercises that the user can do to improve his/her overall score.

In some embodiments, a tone of the notification or feedback is personalized for the individual. For example, personalization of a tone may be based on a demographic, a medical history, an emotional state, a progress, a location, a profile, or an overall score of the individual. For example, a profile of an individual may indicate that he/she responds best to sharp but constructive criticism, so the tone of the feedback or instructions may reflect this individual preference. Further for example, the individual may have a medical history of depression or mood swings, so the tone of the feedback may be exceptionally uplifting and positive to reflect this individual preference. Still further for example, the user may be extremely close to reaching his/her target overall score, so the tone of the feedback may be encouraging and empowering.

In some embodiments, the notification may include an overall score (as described elsewhere herein), a compliance score (as described elsewhere herein), or a compliance rating of the individual relative to one or more peers. The notification may be based on one or more of the plurality of parameters (e.g., exercise compliance, medication compliance, patient report inputs, patient generated health data, etc.), as described elsewhere herein. The notification may be displayed on a display of a mobile computing device of the individual. The compliance rating is based on a comparison of the overall score to an expected overall score for the individual. The expected overall score of some embodiments is based on projections of how the measured parameters of the individual will change over time if he/she executes the prescribed exercises or other instructions. The expected overall score may be updated over time as the sensor system measures the parameters and the system tracks user progress over time. Alternatively, the expected overall score may be based on a goal set by the individual or a healthcare provider of the individual, for example based on a target or goal for the individual. In some instances, the overall score may predict a time range for recovery. In further instances, a time range for recovery may be based on adherence and/or patient reported outcome (PRO) data, and/or patient generated health (PGHD) data.

In some embodiments, instead of or in addition to sending the notification to the individual, the monitoring system transmits a notification to a caregiver, healthcare provider, family member, friend, and/or peer. This notification may also include a compliance rating of the individual, as shown at block 1150 of FIG. 11. The notification prompts one or more of the caregiver, healthcare provider, family member, friend, and peer to contact the individual and/or healthcare provider to encourage the individual to adhere to his/her prescribed care instructions and to provide a notice to one or more of: the caregiver, healthcare provider, family member, friend, and peer.

Sensor System

Figure 3:
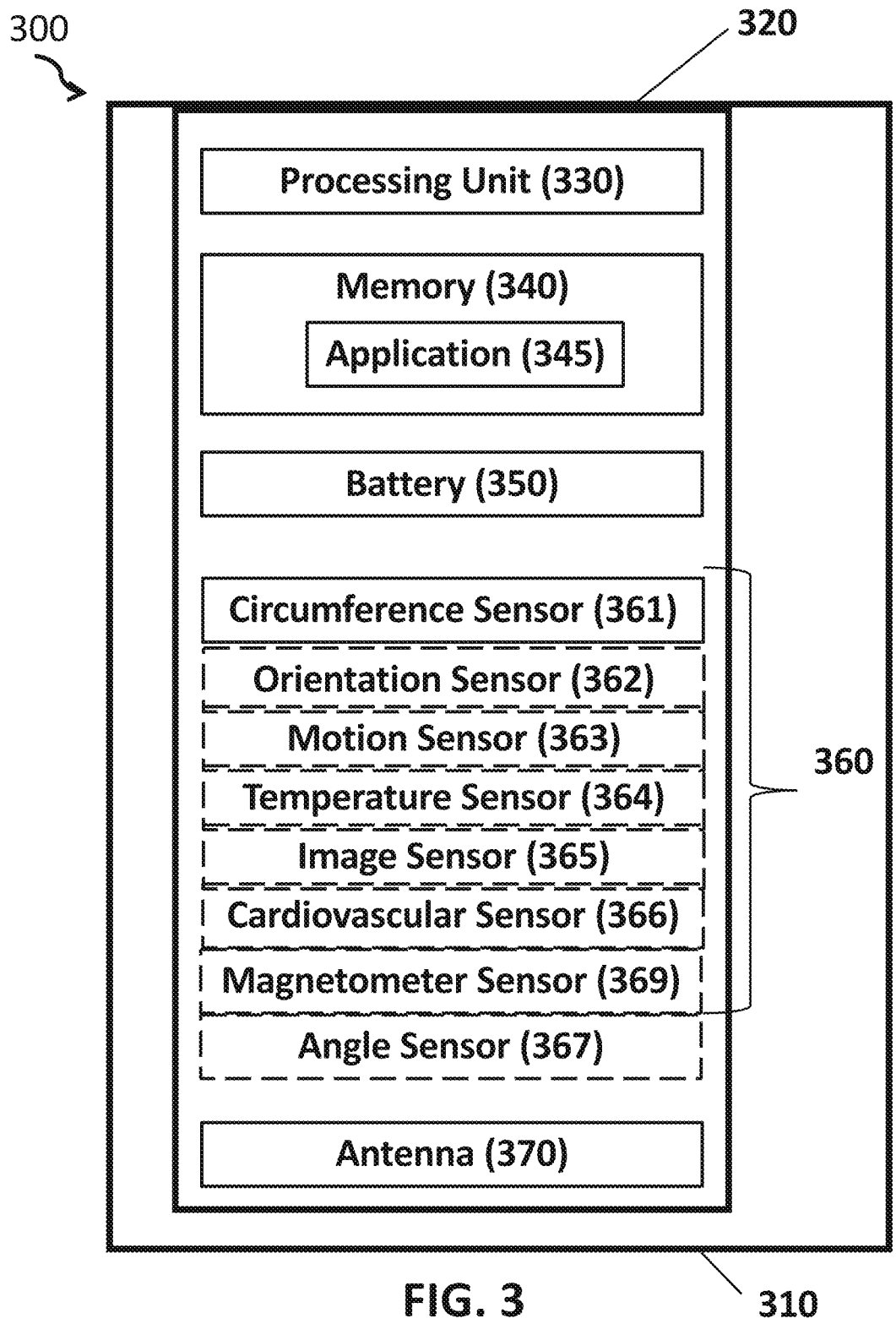
FIG. 3 illustrates a functional block diagram of one embodiment of a sensor system provided within the monitoring system of FIG. 1C.

A functional block diagram of one embodiment of a sensor system is provided in FIG. 3. While numbered uniquely, one skilled in the art will appreciate that the sensor system 110 of FIG. 1C may be formed of any embodiment of a sensor system described herein and may include any of or all the functional components described with respect to the sensor system 300 shown in FIG. 3. Moreover, although illustrated separately, it is to be appreciated that the various functional blocks of the sensor system 300 need not be separate structural elements.

The sensor system 300 of various embodiments includes a stretchable component 310 configured to adhere to or fit securely around the body portion, and a sensor module 320 coupled thereto. In some embodiments, at least a portion of the sensor module 320 is removable from the stretchable or adhesive component 310. For example, the stretchable or adhesive component 310 may be formed of a machine-washable fabric, and at least a portion of the sensor module 320 may be housed within a protective casing that is detachable from the stretchable or adhesive component 310. In some embodiments, a first portion of the sensor module 320 is integrated into the stretchable or adhesive component 310 while a second portion is positioned within the protective casing. For example, a processing unit 330 and a battery 350 may be stored within the protective casing, while a strain gauge, resistor, and/or other sensing components 360 of the sensor module 320 may be weaved into, disposed within, printed on, affixed to, or otherwise integrated into the fabric of the stretchable component 310.

In some instances, sensors are configured to be worn for long durations; in other instances, sensors may be configured to be worn for short periods. Duration of wearing may depend on the time to track specific exercises. Specifically, in some embodiments, sensors may be worn for over 3 months and/or for the entire duration of a clinical episode of care. Sensors may be worn for a fixed duration (e.g., greater than 2 weeks, a month, two months, three months, six months, etc.) without the need for recharging thus allowing for greater usability and safety.

Sensors may be configured to integrate audio or haptic feedback (e.g. vibration) technology to provide patients with feedback as they achieve a pre-configured limit for a range-of-motion, and/or for the performance of on-going assessments.

As shown in FIG. 3, the sensor module 320 includes a processing unit 330, which may be a general-purpose microprocessor, a digital signal processor (DSP), a field programmable gate array (FPGA), an application specific integrated circuit (ASIC), or other programmable logic device, or other discrete computer-executable components designed to perform the algorithms and functions described herein. The processing unit 330 may also be formed of a combination of computing devices, for example, a DSP and a microprocessor, a plurality of microprocessors, one or more microprocessors in conjunction with a DSP core, or any other suitable configuration.

In various embodiments, the processing unit 330 is coupled, via one or more buses, to the memory 340 in order for the processing unit 330 to read information from and write information to the memory 340. The processing unit 330 may additionally or alternatively contain memory 340. The memory 340 can include, for example, processor cache.

The memory 340 may be any suitable computer-readable medium that stores computer-readable instructions for execution by computer-executable components. For example, the computer-readable instructions may be stored on one or a combination of RAM, ROM, flash memory, EEPROM, hard disk drive, solid state drive, or any other suitable device. In various embodiments, the computer-readable instructions include application software 345 stored in a non-transitory format. The software, when executed by the processing unit 330, causes the processing unit 330 to perform one or more operations described elsewhere herein.

In various embodiments, a power supply, such as a battery 350, is electrically coupled to provide power to the processing unit 330 and other electronic components. The battery 350 may be rechargeable or disposable. Additionally, some embodiments of the sensor module 320 may include one or more signal processing components, such as a filter (e.g., low pass, high pass, or band pass filter), an amplifier, and/or an analog-to-digital (AD) converter.

As shown, the sensor module 320 includes one or more sensors 360 configured to detect parameters indicative of the monitored individual's health. For example, the sensor module 320 includes a circumference sensor 361 configured to detect changes in the circumference of the body portion. The circumference sensor 361 may detect a change in circumference indirectly. For example, when the body portion expands in circumference, the stretchable component 310 positioned around the body portion experiences an increase in tensile stress that causes strain (i.e., a physical deformation) in the stretchable component 310. In some embodiments, the circumference sensor 361 includes an electrical component positioned on or embedded within the stretchable component 310. The electrical component may itself experience strain in response to the increased tensile forces in the stretchable component 310. This increased strain in the electrical component changes the electrical conductance, and thus, the inductance, resistance, and/or capacitance of the component in a known, predictable manner. Thus, the strain can be calculated from a detected change in inductance, resistance, and/or capacitance of the electrical component. In turn, the processing unit 330 is configured to calculate a change in circumference from the detected change in inductance, resistance, and/or capacitance and obtain an absolute or relative circumference measurement. The electrical component may be a foil strain gauge, semiconductor strain gauge (e.g., a piezoresistor), a nanoparticle-based strain gauge, a capacitive strain gauge, any other resistor, or any other suitable electrical component that experiences a detectable change in electrical properties in response to strain.

In some embodiments, the sensor module 320 additionally includes one or more of: an orientation sensor 362, a motion sensor 363, a temperature sensor 364, an image sensor 365, an angle sensor 367, one or more cardiovascular sensors 366, and a magnetometer sensor 369. The orientation sensor 362 of some embodiments is a gyroscope configured to detect when the body portion has tilted, been elevated, or otherwise changed position. The motion sensor 363 of some embodiments is an accelerometer configured to detect changes in motion such as repetitive changes in motion indicative of exercise. The temperature sensor 364 of some embodiments is a thermistor, thermometer, or other temperature-responsive sensor configured to detect changes in skin temperature at the body portion. The image sensor 365 of some embodiments is a camera, semiconductor charge-coupled device (CCD), or complementary metaloxide-semiconductor (CMOS) configured to detect changes in the attenuation of light waves indicative of changes in skin color at the body portion. The angle sensor 367 of some embodiments is an inclinometer, clinometer, or goniometer that measures angles of slope (or tilt), elevation, or depression of an object with respect to gravity, for example to measure a range of motion of a body portion. The magnetometer sensor may measure the movement of a body portion relative to the magnetic field of the earth. In some instances, a magnetometer sensor may generate a pattern during use by the patient while performing an exercise on a body portion to which the sensor is attached. The one or more cardiovascular sensors 366 may include, for example, a pulse oximeter, a plethysmograph sensor, a pulse rate monitor, and/or a heart rate monitor. Exercise performed by a user may generate a signal from any of the preceding sensors that may be correlated with an ideal pattern to determine if the exercise was performed properly (e.g., proper form, duration, etc.) and the number of times an exercise was attempted as well as the number of times it was performed properly.

In various embodiments, some of or all the measurements obtained by the sensor system 300 are transmitted wirelessly, for example, via a communication antenna 370, to the mobile computing device 120 for processing, analysis, and storage. The communication antenna 370 may be, for example, a transmitter or a transceiver. The measurements may be automatically pushed to the mobile computing device 120 or retrievable by a request from the mobile computing device 120. In other embodiments, some of or all the measurements are processed, analyzed, and stored on the sensor system 300.

Various, non-limiting embodiments of the sensor system 300 are provided in FIGS. 4A-4K. As shown, each sensor system 300 includes a stretchable or adhesive component 310 and a sensor module 320. While the sensor module 320 may be largely positioned within a protective casing that houses many of the electrical components, at least a portion of the circumference sensor extends outside of the casing and is positioned to experience strain induced by the circumference of the body portion. In some embodiments, such as the embodiments of FIGS. 4A-4B, the sensor system 300 is formed of a strap, band, adhesive strip, or belt. The entirety of the strap, band, adhesive strip, or belt may be deformable and circumferentially stretchable, or only a portion of it may be configured to stretch. The strap, band, adhesive strip, or belt may be sized and configured for placement on an upper torso or chest or lower torso or waist, as in FIG. 4A. Alternatively, it may be sized and configured for placement on a limb, such as an upper arm, lower arm, upper leg, or lower leg, as in FIG. 4B.

In various embodiments, the sensor system 300 is removable and configured for repeated reattachment. In order to achieve consistent, reliable, and accurate results, it is desirable for the various sensors to be located at the same locations with each reattachment. To facilitate proper positioning of the sensors, in some embodiments, the sensor system 300 is integrated into clothing, footwear, a band, or a brace. For example, one or more stretchable components 310 and sensor modules 320 may be integrated into a shirt (FIG. 4C), sports bra, shorts, leggings or pants (FIG. 4D), underwear, compression socks or other socks (FIG. 4E), partial socks or sleeves (FIG. 4F), knee brace (FIG. 4G), ankle brace (FIG. 4H), or any other suitable garment. Placement of the sensors may be configured to precisely track the localized movements, position, and orientation of that body part or joint. In some embodiments sensors must be flexible enough to be worn at any joint in the body to track motion at any of the axes. In further instances, sensors may be configured such that they may be worn on a specific joint or location of the body.

Figure 4A:
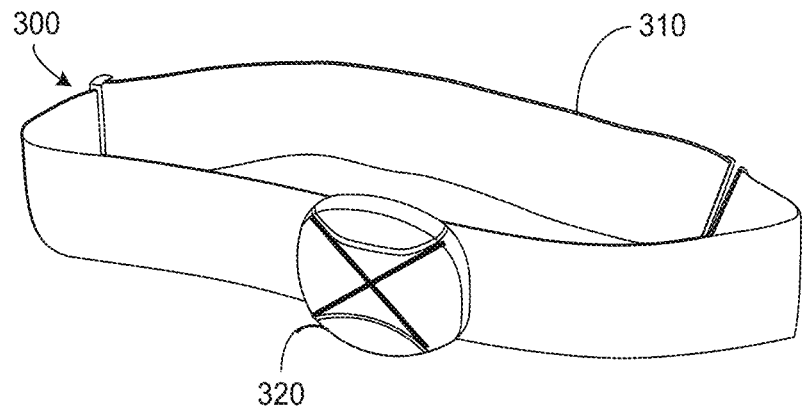
FIGS. 4A-4L schematically illustrate a plurality of examples of the sensor system of FIG. 3.
Figure 4B:
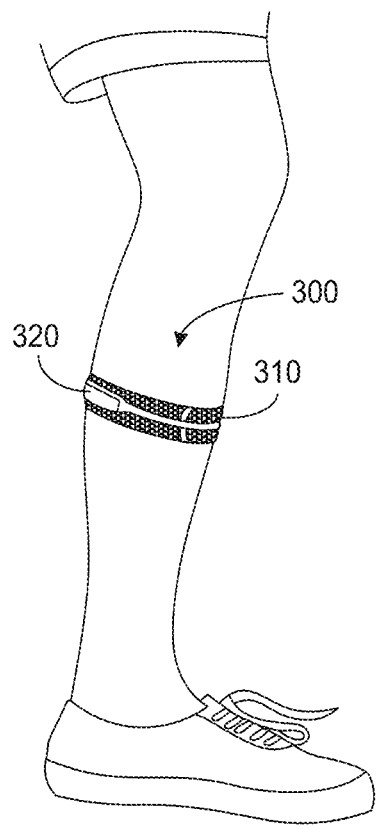
Figure 4C:
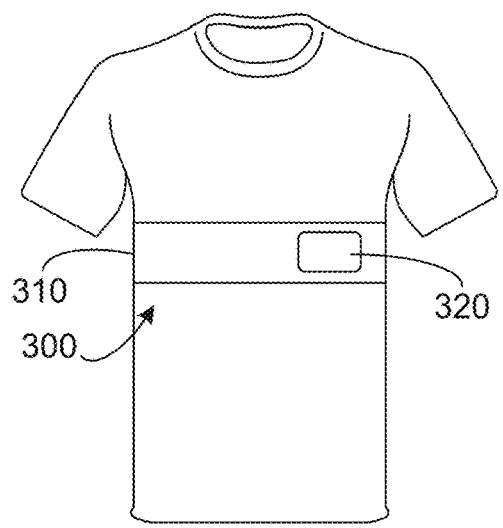
Figure 4D:
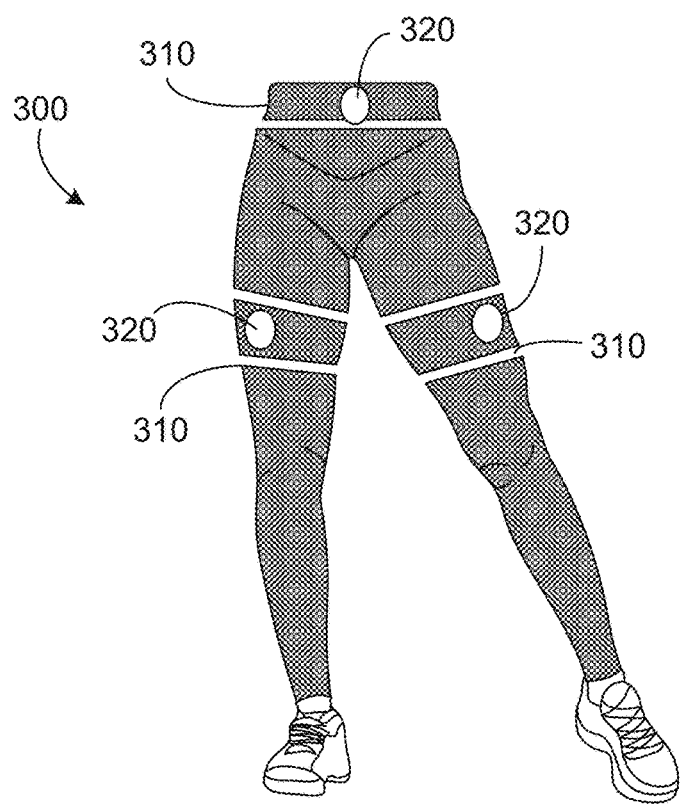
Figure 4E:
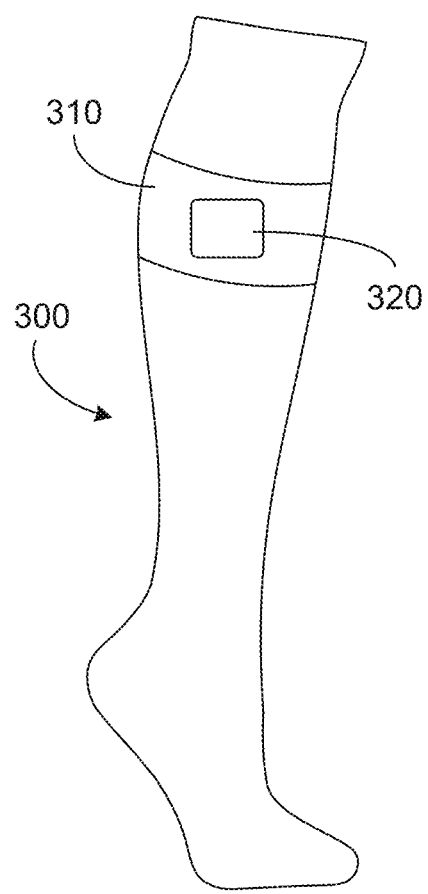
Figure 4F:
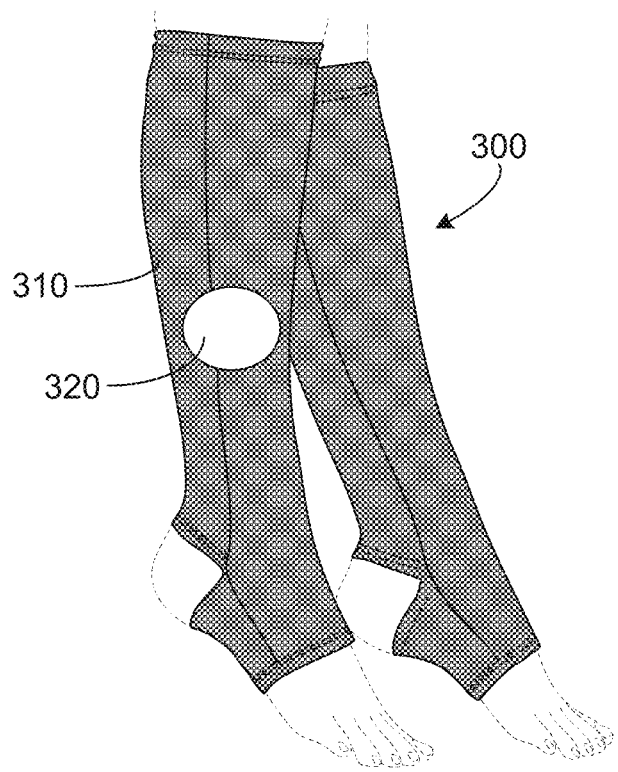
Figure 4G:
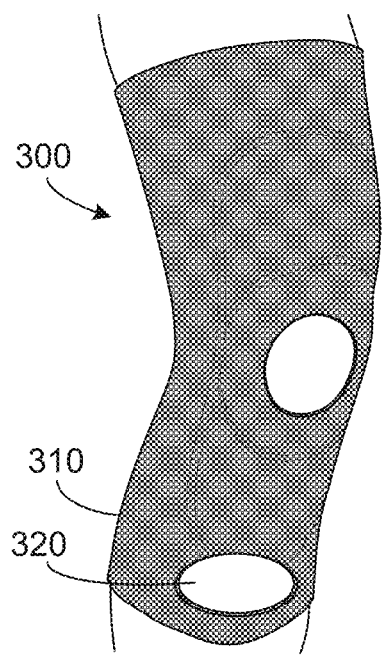
Figure 4H:
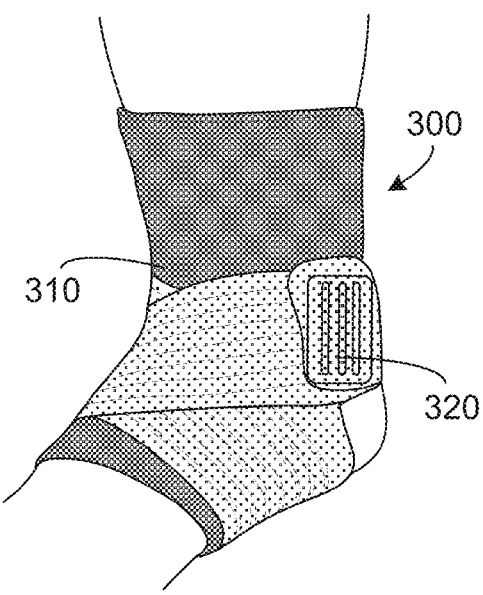
Figure 4I:
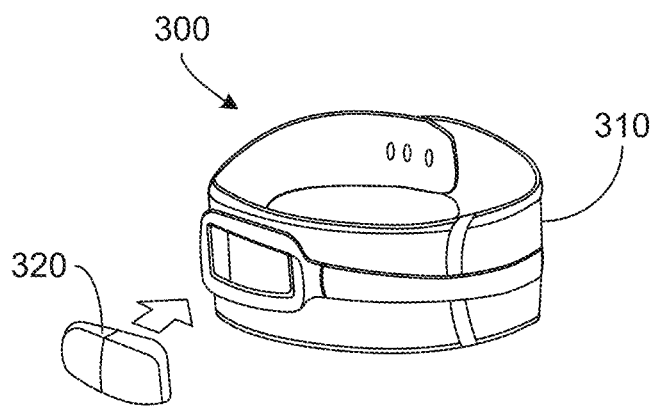
Figure 4J:
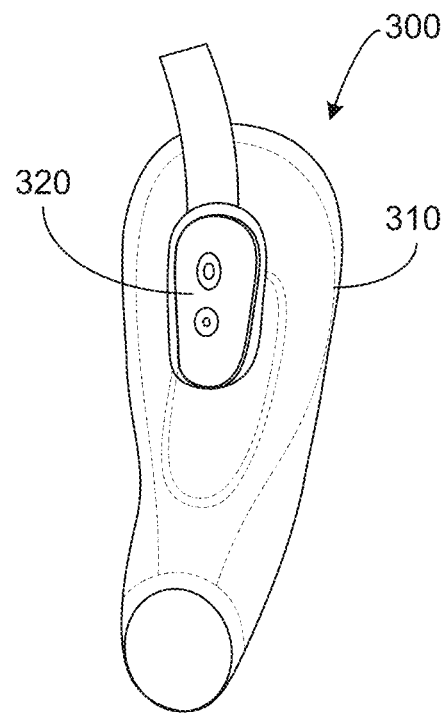

In some embodiments, including any of the embodiments described with respect to FIGS. 4A-4K, at least a portion of the sensor module 320 is removable. This is illustrated, for example, with the band provided in FIG. 4I and the leg sleeve/tube provided in FIG. 4J. The removable portion of the sensor module 320 may be securable to the stretchable component 310 via any suitable attachment mechanism. For example, the stretchable component 310 may include a cradle or holder sized to receive the removable portion of the sensor module 320, and the removable portion of the sensor module 320 may snap or clip into the holder, as shown in FIG. 4I. Alternatively, the removable portion of the sensor module 320 may zip or hook into place, or it may slide between layers or into a pocket of the stretchable component 310, as shown in FIG. 4J. In some such embodiments, the stretchable component 310 is washable. In some embodiments, the removable portion of the sensor module 320 is enclosed in a water-resistant or water-proof protective casing. In some embodiments, the removable portion of the sensor module 320 may house the processing unit 330 and any associated electrical filtering and processing components, the battery 350, an accelerometer, a gyroscope, and/or one or more additional parameter sensors. In some embodiments, the removable portion is interchangeable and configured for attachment to a plurality of garments and devices. In some embodiments, the removable portion is automatically activated upon attachment to a garment or automatically deactivated upon detachment from a garment.

Figure 4K:
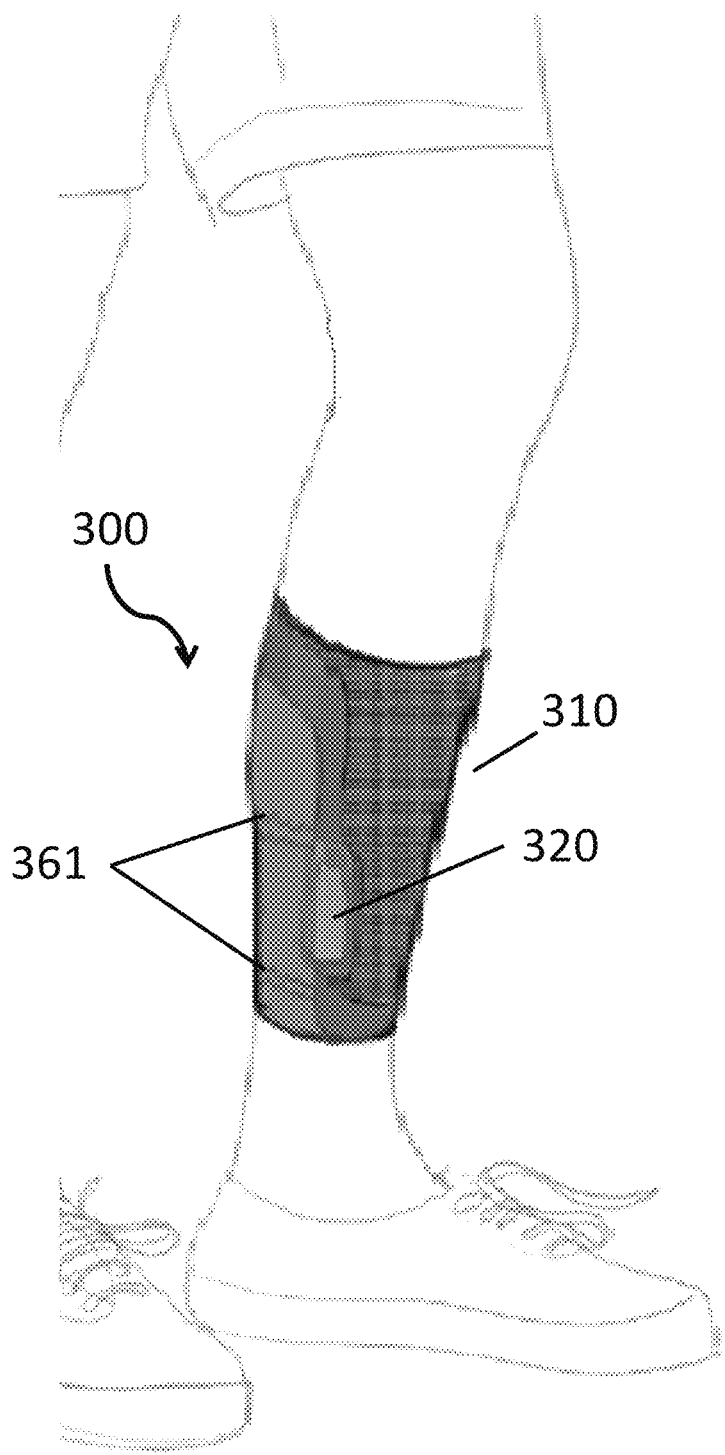

In FIG. 4K, the portion of the sensor 361 that is integrated into the stretchable component 320 is schematically drawn with visible lines to improve understanding. One skilled in the art will appreciate that each of the sensor systems 300 provided herein may have a similar feature, but in FIGS. 4A-4J, such a feature is not visible from the outside of the device. The depicted circumference sensor 361 may be any strain gauge or other suitable device described elsewhere herein. Additionally, as shown in FIG. 4K, any of the sensor systems 300 of FIGS. 4A-4K may include multiple circumference sensors 361 (e.g., two, three, or more sensors) in order to sense a parameter indicative of circumference at a plurality of locations of the body portion.

Figure 4L:
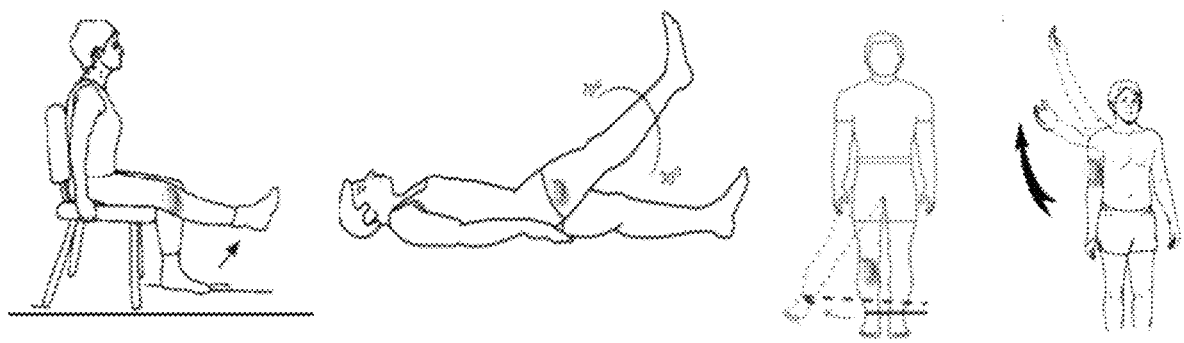

In various embodiments, for example as shown in FIG. 4L, sensors may use a magnetic mounting system so that localized body motion, circumferential width increase, orientation, and/or localized temperature variations may be detected. In some embodiments, the magnet is inside the sensor and attached to a magnetized adhesive strip which may be placed anywhere on the body. In such embodiments, the sensor may be used to precisely track the localized movements of that body part or joint.

In various embodiments, the sensor may be built using flexible electronics to improve the attachment capability and allow more flexible and accurate movement tracking. Alternatively or additionally, a sensor may comprise an adhesive strip and a magnetic material (e.g., not magnets themselves) placed inside or glued to an antibacterial single sided or double-sided adhesive. In further embodiments, the antibacterial single sided or double-sided adhesive may comprise one or more non-stick surfaces, padded regions, or segments of differing degrees of stretch or stiffness. Stretchiness or stiffness may be defined as a parameter of force divided displacement, with ranges of stretchiness, stiffness, or tensile modulus. Exemplary ranges of material properties for adhesive or materials comprising adhesive may include modulus of elasticity in the range of 0.001 to 24 GPa. Magnets inside the sensor and/or the magnetic adhesive strip may provide the needed adhesion to attach the sensor to the body. The adhesive portion of the magnetic adhesive strip may be configured to stay attached to the skin for minutes, hours, days, weeks, months, or years. The adhesive portion of the magnetic adhesive strip and/or the magnetic adhesive strip itself may be configured to withstand exposure to water, wind, abrasion, etc. The tackiness of adhesives used to generate an adhesive strip may comprise a range of between 0.1 to 15N as measured by a tack tester.

In some embodiments, the magnetic adhesive strips may be provided to the user in packs or sets for placement at different locations of the body, and or in packages or sets that facilitate ease of use and adoption by the patients of the system.

In various embodiments, the magnetic adhesive strips may be disposable instead of reusable, and the patient may replace the previous magnetic adhesive strip with a new one after a lifecycle of use of the magnetic adhesive strip is complete. In some embodiments, a lifecycle of use may be on the order of minutes, days, weeks, months, or years. In some methods, for using a magnetic adhesive strip, the user may replace the magnetic adhesive strip at a rate or increment that is predetermined (e.g., every day, every week, every other week, once a month, etc.).

In various embodiments, as shown in FIG. 4L, a patient wearing the sensor may be asked to execute exercises targeted for a specific muscle group and/or joint. Sensors may be configured to track planar movements of the body across sagittal, transverse, and coronal planes. In such embodiments, tracking of all types of movements and measures of flexion (e.g., degrees of flexion) may occur, including for example flexion, extension, abduction, and adduction. In some instances, tracking may be performed for exercises prescribed by a physical therapist, for example, a long arc quad extension done while sitting on a chair (as shown in FIG. 4L) captures knee extension from 90 degree (bent) to 0 degree (straight).

Additionally or alternatively, sensors may be configured to track speed of movement, length or times of the duration over which the user (e.g., patient or athlete) was able to hold a strenuous position (e.g., a stretch, a lift, plank, etc.). Metrics measured from one or more sensors may be used to compute, assess, or measure the user's strength and/or endurance.

In additional or alternative embodiments, sensors may be configured to monitor or assist in the assessment or performance of isometric exercises (e.g., exercises that do not involve movement but do involve exercising the muscles). In such instances, the sensor may be configured to track the duration of a stretch and whether the body part shook as part of executing the stretch. Accurate detection of vibratory movements may be used to calibrate, compute, assess, or measure the strength of the joint and/or muscle group involved in performing the exercise.

Figure 4M:
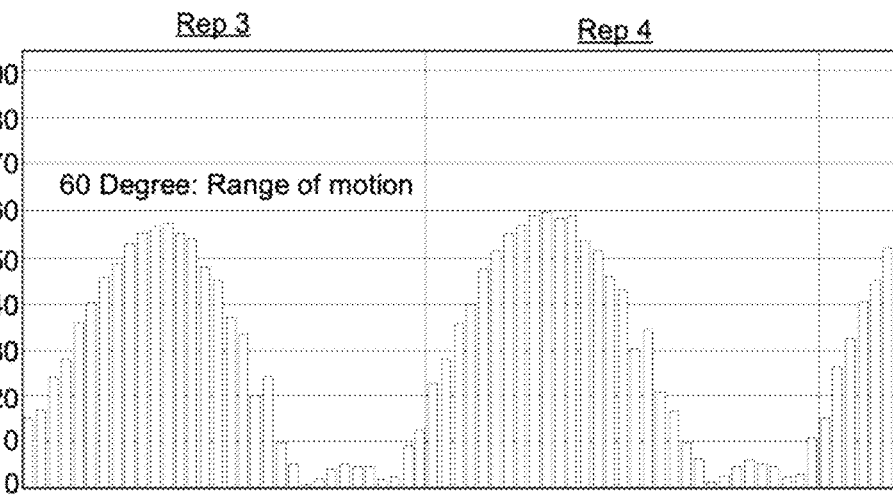
FIGS. 4M-4O illustrate exemplary measurements collected from sensors monitoring joint extension and/or limb movement.
Figure 4N:
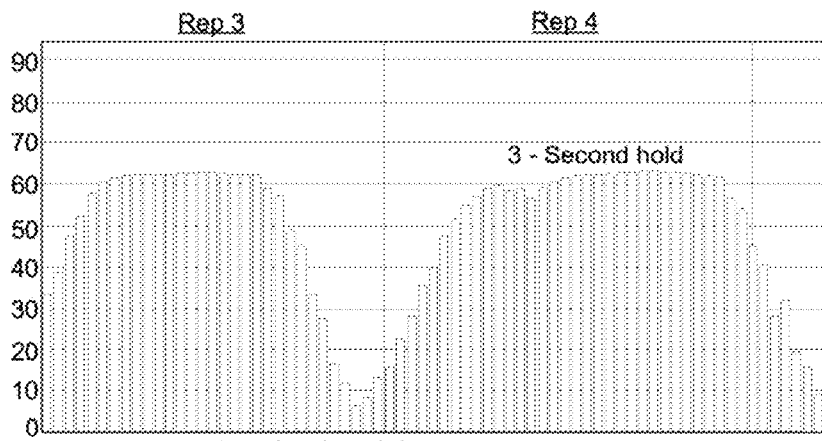
Figure 4N:

Sensors may be dynamically calibrated to measure the smoothness of movement during movement or exercise. In some instances, the sensors may be used to measure a body portion, as shown in FIGS. 4M and 4N. As shown, the sensors are able to detect the performance of a joint extension performed two different ways. In FIG. 4M the patient performs a typical joint extension and in FIG. 4N the patient performs the joint extension with a 3 second hold at 60 degrees ROM, the maximum range of motion for the exercise. The sensors are able to detect and distinguish between the different ways of performing the exercise, illustrated here as the sharp peaks in FIG. 4M indicate that the direction of body portion motion changes shortly after reaching 60 degrees ROM, whereas the data in FIG. 4N shows that peaks flattening out at 60 degrees ROM. Additionally, the sensors in FIG. 4N can detect shaking of the user during the hold period, which can be used to determine the strength of the body portion used in performing the exercise. Data including whether the exercises were performed, how they were performed and features of the performance (e.g., shakiness, speed, smoothness, etc.) may be used by the system to dynamically calibrate the performance of the exercise (e.g., according to flexibility, strength, and endurance) and impact on the prognoses and recovery trajectory. In some instances, the sophistication or degree of difficulty for the exercises in a patient's care plan may be dynamically adjusted based on the performance measured by the sensors. Sensors are equipped to make adjustments and identify flexibility, strength, and endurance of the patient at resolutions far greater than what would be obvious to a trained eye. Sensors may be used to measure both the quality of movement as well as the quantity of movement. Each exercise in a care plan may have a separate tuning, with weaker muscles displaying jerkier motions and difficulty of exercises requested of the patient adjusting according to the actual performance of the patient. The rate of which data is collected and tuned may be dynamically adjusted based on one or more of: the previous performance of the user, the type of exercise being performed, and the battery life of the sensor or other hardware associated with the sensor including the mobile device running the application.

Sensors may detect movement of a body portion in all three planar directions (e.g., X, Y and Z). FIG. 4N illustrates data collected for motion of the leg portion during standing hip abduction (see FIG. 4L second exercise from right). In this exercise, the leg is extended away from the body and FIG. 4N shows sensor data for the leg movement in three planes. During the exercise, the leg was moved in the X direction (second panel from the top), however movement is also detected in the Y (third panel from the top) and Z direction (bottom panel). Sensors may be equipped to detect slight and voluntary as well as involuntary movements in the coronal, sagittal and transverse planes. Detection of slight movement of joints that are supposed to be stationary and are not being used during an exercise are detected by the sensors and recorded and identified by the monitoring system. In some instances, these recordings may be integrated into changes in the care plan, estimates of prognosis/recovery, and/or transmitted to healthcare providers. Some exercises, such as standing hip abduction have a few degrees of movement, making them hard to measure in the presence of other movements (e.g., movement of joints that are supposed to be stationary). The monitoring system comprises an algorithm with inbuilt thresholds that must be met before a repetition is designated as complete. Thresholds may be programmed separately for each exercise and may take into account the likely movement of other joints. The algorithm may also have adaptive goals, wherein the thresholds are relaxed in the first few days after an operation and then slowly advanced. Thresholds may be adjusted according to one or more features including but not limited to: position of patient in recovery process, user profile, care plan, indications of other conditions or compensatory muscle or joint issues, and pain levels.

Figure 5:
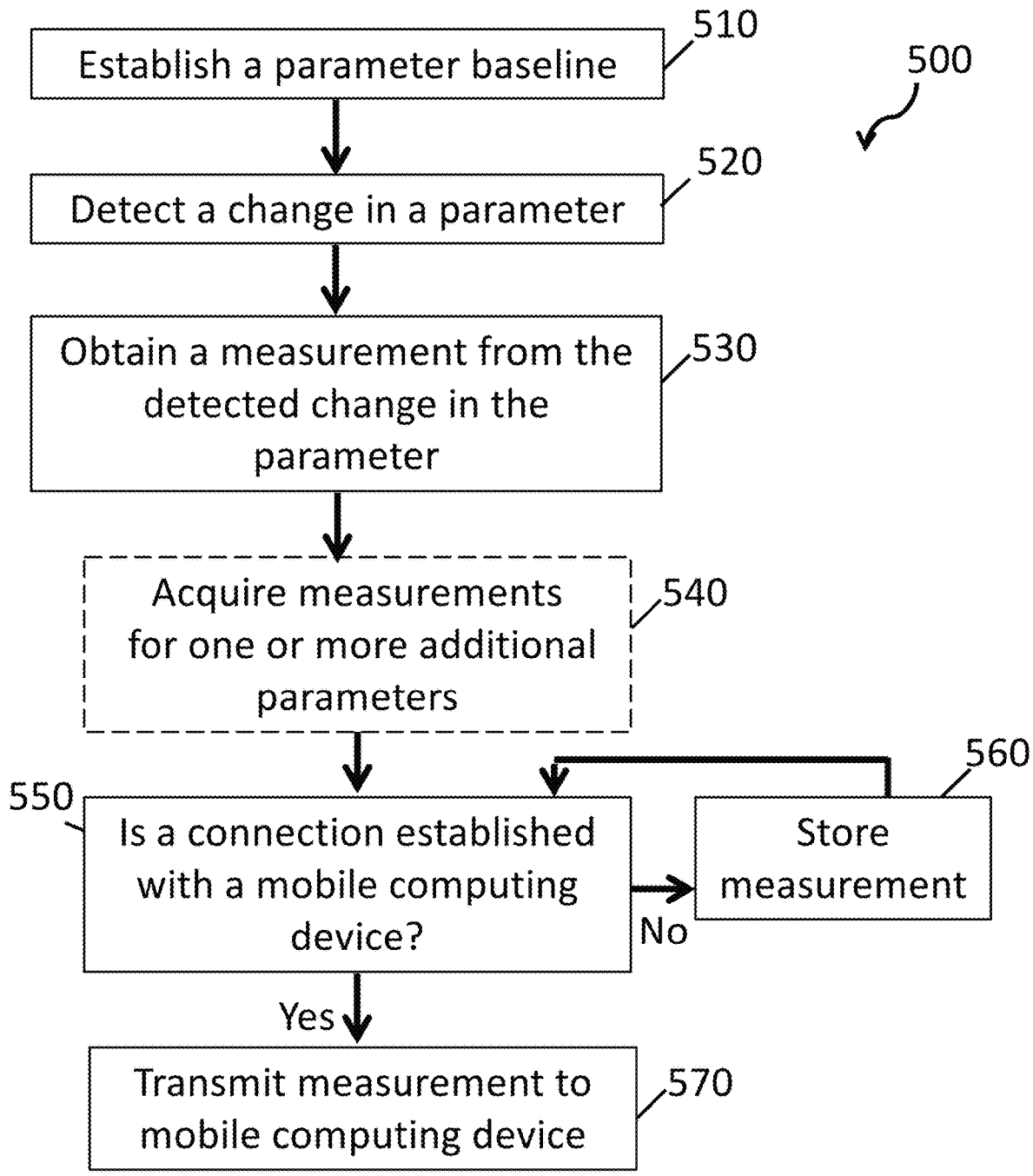
FIG. 5 illustrates a flow chart of one embodiment of a method performed by the sensor system of FIG. 3.

FIG. 5 depicts one example of a method 500 performed by the sensor system 300 described elsewhere herein. As shown at block 510, the method includes calibrating the sensor system 300 to establish a parameter baseline. When the sensor system 300 is first positioned on an individual, the stretchable or adhesive component 310 will experience some degree of strain. As described above, strain, position, or other changes may be detectable by a sensor 361, which is formed of an electrical component positioned on or embedded within the stretchable component 310. The electrical component may itself be deformable in response to tensile stress or movement and may experience a change in electrical properties when deformed or moved, resulting in a change in a parameter such as the inductance, resistance, and/or capacitance of the electrical component. Following positioning of the sensor system 300 on the body portion, the initial parameter reading is set as the baseline. In some embodiments, the processing unit 330 calculates an actual baseline strain, position, and/or circumference measurement, setting the baseline to that value. In some embodiments, the baseline could be individual specific (e.g., my range of motion today vs. yesterday) or at the population level (e.g., the cohort of patients in recovery). In adaptive goaling or other calibrations, the baseline can be adjusted periodically, on-demand or automatically. In other embodiments, measurements are relative, and the initial parameter readings establish the zero value. As part of the calibration process, the sensor system 300 of some embodiments performs a status check. For example, in some embodiments, the processing unit 330 of the sensor module 320 checks to ensure each sensor is operational; in some embodiments, it determines whether the stretchable component 310 is experiencing a level of strain below a safety threshold. In some embodiments, the sensor system 300 or a mobile computing device communicatively coupled thereto is configured to generate an alert if the sensor module 320 detects that the stretchable component 310 is too tight. In some embodiments, the sensor system 300 includes a vibrational element configured to generate haptic alerts.

At block 520, the method 500 includes detecting a change in a parameter that correlates to, and is indicative of, a change in position, orientation, or circumference. The sensor system 300 is configured to be worn by the monitored individual over a period of time, for example, from several hours to several weeks. During that time, the inductance, resistance, capacitance, and/or other parameter of the position or circumference sensor 361 changes as the position or circumference of the body portion changes. These changes in the parameter of the position or circumference sensor 361 may be detected, filtered, and processed by the processing unit 330 continuously or repeatedly, for example, at regular intervals.

At block 530, the sensor system 300 obtains a circumference measurement from the detected change in the parameter. The circumference measurement is calculated by the processing unit 330 using pre-programmed relationships and equations, for example correlating circumference and/or strain to the detected change in a parameter. For example, in some embodiments, strain is calculated using the equation:

$$GF = \frac{\frac{\Delta R}{R}}{\varepsilon},$$

where ε=strain; ΔR=change in resistance; R=initial resistance; and GF=gauge factor, which is a predefined value. Additionally or alternatively, in some embodiments, a cross-sectional area of the body portion may be determined using the equation:

$$R = \rho \frac{L}{A},$$

where R=resistance; ρ=the specific resistivity, a predefined value; L=length of the electrical component (e.g., length of the resistor); and A=the cross-sectional area of the body portion. Circumference can be determined, for example, relying on the above equation and the relationships: Area=$\pi r^2$, and Circumference=$2\pi r$, where r=the radius. From these and/or other pre-programmed equations, a change in circumference can be determined from a change in resistance, inductance, or capacitance. The calculated circumference measurement may be an absolute measurement or a relative measurement providing a change in circumference relative to the baseline or other previous circumference measurement.

The processing unit 330 of various embodiments calculates measurements repeatedly, for example, at regular intervals. In some embodiments, the interval length varies based on the measurements. For example, the processing unit 330 may begin calculating measurements at a first interval (e.g., every hour). When a change in circumference, orientation, or position is detected, the processing unit 330 may transition to calculating circumference, orientation, or position measurements at a second, more frequent interval (e.g., every 15 minutes) to enable closer monitoring of the circumference, orientation, or position. By obtaining circumference, orientation, or position measurements frequently over time, the sensor system 300 is able to identify and exclude anomalous measurements, for example, those caused by movement, muscle flexing, or noise.

As shown at block 540, in some embodiments, the sensor system 300 may optionally acquire measurements from one or more additional parameters. For example, one or more of the orientation sensor 362, motion sensor 363, temperature sensor 364, and image sensor 365 may sense changes in one or more parameters, and the changes may be detected, filtered, and processed by the processing unit 330. For example, one or more additional parameters may be used to calculate a range of motion of a body portion of the user, as described in further detail elsewhere herein.

As shown at block 570, in various embodiments, the antenna 370 of the sensor system 300 transmits the circumference, orientation, or position measurements and any other acquired measurements from the processing unit 330 of the sensor system 300 to a mobile computing device 120. In order to successfully transmit the measurements, in some embodiments, the sensor system 300 first determines whether a communication connection exists between the sensor system 300 and the mobile computing device, as shown at block 550. If the sensor system 300 and mobile computing device are not connected, the sensor system 300 stores the measurements and data in memory 340 in the sensor module 320 until a connection is established, as shown at block 560. When a communication connection does exist, the antenna 370 may transmit the measurements and data upon establishing the connection, upon receiving new measurements, at a programmed interval, or when requested by the mobile computing device 120. In some embodiments, the mobile computing device 120 receives and analyzes the measurements (as described in more detail below), and based on the measurements, the mobile computing device 120 transmits instructions back to the sensor system 300 instructing the sensor system 300 when and/or what measurements should next be queried, processed, or transmitted.

Figure 12:
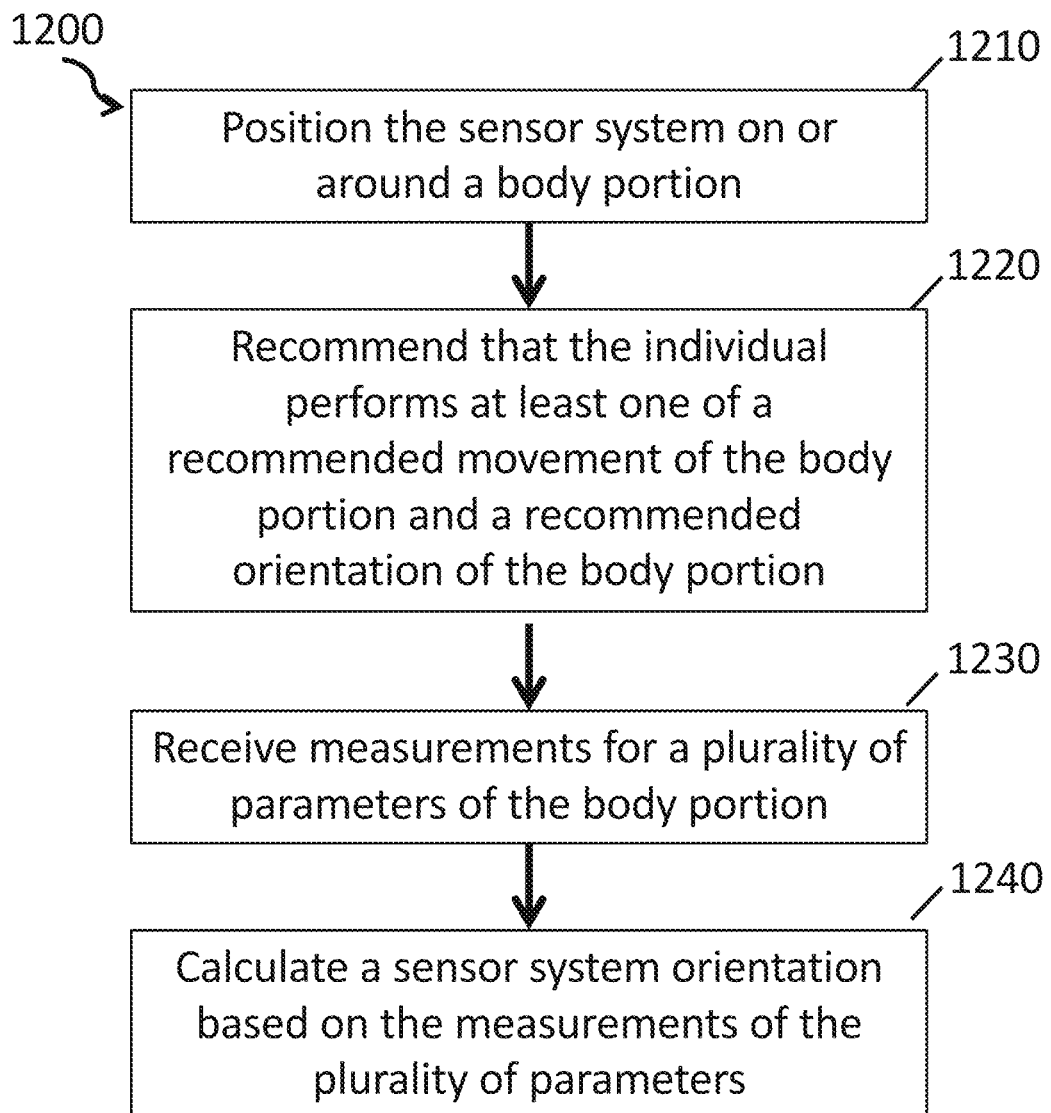
FIG. 12 illustrates a flow chart of one embodiment of a method for calculating a sensor system orientation.

In addition to or alternatively, the monitoring system calibrates the sensor system by determining an orientation of a sensor system, as shown in the method 1200 of FIG. 12. At block 1210, the method 1200 includes positioning the sensor system around or on a body portion, for example a leg (e.g., leg, calf, knee), an arm (e.g., bicep, forearm, elbow), a torso, an ankle, a wrist, or a chest. At block 1220, the monitoring system recommends that the individual performs at least one of a recommended movement of the body portion or a recommended orientation of the body portion.

At block 1230, the method includes receiving measurements for a plurality of parameters of the body portion. Before, during, and/or after the movement or orientation, the gyroscope and/or accelerometer of the sensor system measures one or more of the movement and orientation of the body portion in space to determine whether the sensor system is oriented properly or at least how the sensor system is oriented relative to the body coordinate system of the individual (i.e., registering the sensor system to the body coordinate system). For example, if the system directed the individual to perform a bicep curl, the measurements performed by the sensor system should reflect an anatomically correct and feasible bicep curl (i.e., moving a forearm towards the bicep instead of towards the tricep). In some embodiments, the sensor system further includes an angle sensor, for example an inclinometer, to measure an angle of a joint or a tilt of a body portion to assist in calibrating the sensor system or determining an orientation of the sensor system on the body portion.

At block 1240, the method includes calculating a sensor system orientation based on the measurements of the plurality of parameters. In some embodiments, calculating includes comparing an actual motion or orientation of the body portion to an expected motion or orientation based on the recommended motion or orientation. Further, in such embodiments, the difference between actual and expected is compared to a range of values or a threshold for the recommended motion or orientation. If the difference is outside of the range of values or exceeds or does not reach the pre-determined threshold, the sensor system is determined to be oriented improperly. At such time, the monitoring system may notify (e.g., visually, audibly, haptically) the individual to adjust the placement of the sensor system or the system may register the improper orientation and save it as an updated orientation of the sensor system. The calculations may be performed locally on the sensor system or remotely on a mobile computing device, network computing device, or supervisor computing device.

Muscular skeletal care devices or systems (e.g., monitoring system) comprise an application (e.g., mobile application) that may be utilized to facilitate interaction between the user, optionally a health care provider or administrator, and the sensor. The application may be configured to display a status of a particular exercise regime (e.g., exercises prescribed, exercises completed, when, how well, etc.). In some embodiments, users may interact with the application to execute a given exercise or a selected exercise. Alternatively, patients may tap the sensor to interact with a companion application (e.g. on a mobile device) to indicate completion of an assigned exercise and to move on to another exercise (e.g., assigned to or selected by the user). An application for interacting with the sensor may provide visual and/or auditory feedback to a user on an assigned or selected exercise that was completed by the user or remains to be completed by the user.

Mobile Computing Device

Figure 6:
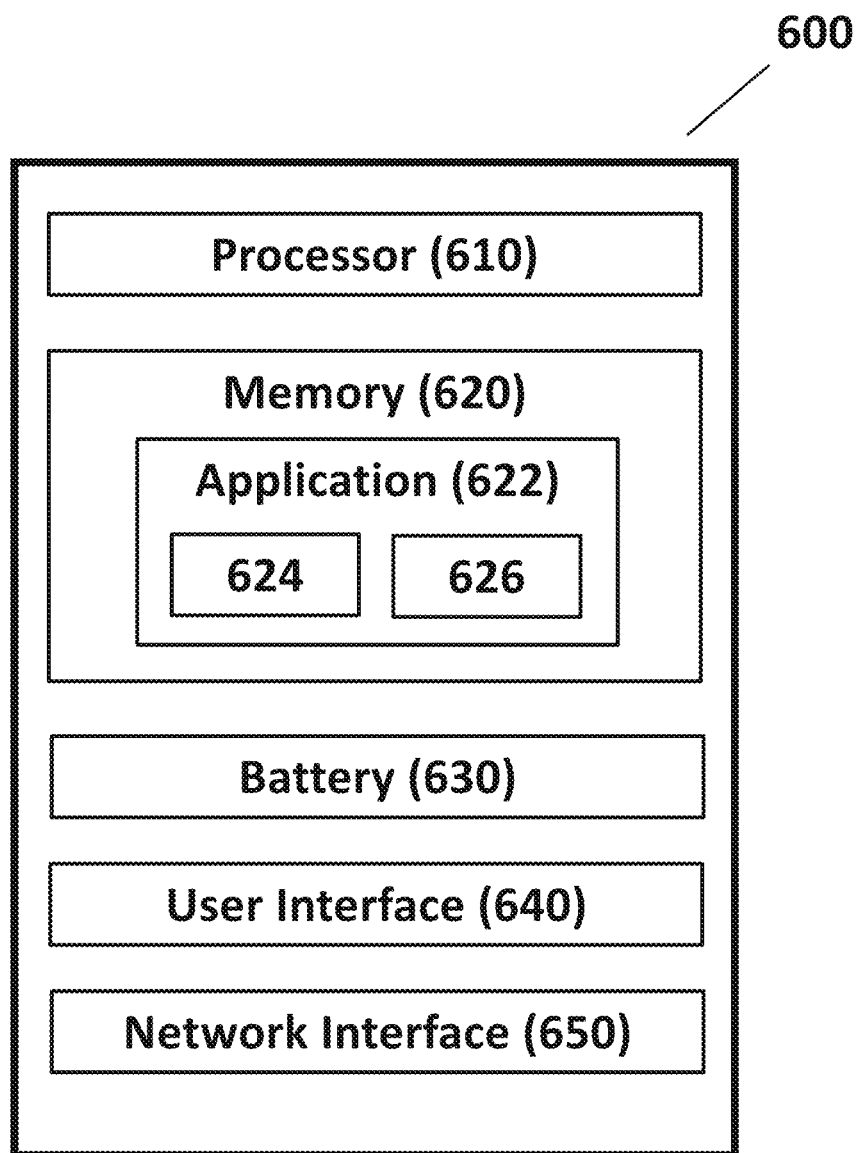
FIG. 6 illustrates a functional block diagram of one embodiment of a mobile computing device provided within the monitoring system of FIG. 1C.

FIG. 6 provides a functional block diagram of one embodiment of the mobile computing device. While numbered uniquely, one skilled in the art will appreciate that the mobile computing device 120 of the system 100 may be formed of any embodiment of a mobile computing device described herein and may include any of or all the functional components described with respect to the mobile computing device 600 of FIG. 6. Moreover, although illustrated separately, it is to be appreciated that the various functional blocks of the mobile computing device 600 need not be separate structural elements.

The mobile computing device 600 of various embodiments includes a processor 610, for example, a general-purpose microprocessor. The processor 610 is coupled, via one or more buses, to the memory 620 in order to read information from and write information to the memory 620. The memory 620 may be any suitable computer-readable medium that stores computer-readable instructions for execution by computer-executable components. In various embodiments, the computer-readable instructions include software stored in a non-transitory format, some such software having been downloaded as an application 622 onto the memory 620. The processor 610, in conjunction with the software stored in the memory 620, executes an operating system and the application 622. Some methods described elsewhere herein may be programmed as software instructions contained within the application 622 stored in the memory 620 and executable by the processor 610.

In various embodiments, a power supply, such as a battery 630 is included within the mobile computing device 600 and is electrically coupled to provide power to the processor 610 and other electronic components. The battery 630 may be rechargeable or disposable.

In various embodiments, power utilization and hence longevity of the sensor may be improved by embedding computational algorithms to adjust or reduce activity of the sensor or other components of the system that are needed to perform the assessment and/or recording or monitoring of activity. Algorithms for conserving power may be embedded in any combination of: the sensor, a smartphone app, and/or in the cloud (e.g., algorithms anywhere, cloud based care cloud). In some embodiments, sensor life may be extended by distributing the algorithms and optimizing pairing between the sensor and phone communication protocols.

In various embodiments, the sensor's processing abilities and power utilization are configured such that the sensor may embed range of motion and exercise repetition detection algorithms that accurately detect angular movements of human joints without needing an app as a companion to the sensor. In such embodiments, data may be directly sent to cloud-based computing infrastructure for analysis (e.g., cloud-based care cloud).

For example, in scenarios such as lying down exercises, the user may not be able to reach the mobile computing device and use the GUI. Algorithms in the sensor can detect a user tapping on it (e.g., to indicate start of next exercise or activity) vs. using movement patterns for an additional feedback.

In various embodiments, the sensor's physical characteristics are further optimized for use by patients in recovery with limited mobility. In such embodiments, the sensor has a body contour-fitting exterior design and body-friendly material (e.g., silicone) for comfort-wear. Designs may incorporate customized shape and asymmetrical weighting of sensor(s) to ensure that sensors do not roll away from users/patients if the user/patient were to experience a fall.

The mobile computing device 600 of various embodiments includes a plurality of interfaces, such as a user interface 640 and a wireless network interface 650. The user interface 640 may include one or more input/output (I/O) devices. In some embodiments, the user input device includes one or more of a button, switch, touchscreen, and keyboard, and the output device includes one or more of a display screen, light display, audio output, and haptic output. The wireless network interface 650 of some embodiments includes a receiver and transmitter for bi-directional communication. The receiver receives and demodulates data received over a communication network. The transmitter prepares data according to one or more network standards and transmits data over a communication network. A communication antenna in the form of a transceiver may act as both a receiver and a transmitter. In some embodiments, the mobile computing device 600 includes a plurality of network interfaces 650, including a first network interface configured for communication with the sensor system 300 and a second network interface configured for communication with a network computing device 130.

In various embodiments, a health monitoring application 622 may comprise an intelligent application on a mobile computing device. The intelligent application may be configured to engage patients in their recovery and help facilitate adherence to a prescribed health care plan using one or more modalities of digital engagement. In some embodiments, the muscular skeletal system may rely on one or more of the following methods to ensure patient engagement and adherence: establish a daily routine, reinforce achievable goals, focus on action instead of history, personalization, and developing a consistent personality profile of the patient. A personality profile for the patient is generated from behavioral factors of the patient, including adherence to pre-operative instructions, the extent to which the patient is engaged with the recovery program via the app, the amount of exercises performed by the patient, etc.

In various embodiments, a health monitoring application 622 is downloaded from a network computing device 130 onto the mobile computing device 600 by the monitored individual. The health monitoring application 622 may include one or more of a user interaction module 624 and a data processing module 626.

The user interaction module 624 of various embodiments instructs the mobile computing device 600 to request information from, and provide information to, the monitored individual. The user interaction module 624 includes a graphical user interface displayable on a screen through which the monitored individual can interact with the monitoring system. The monitored individual may also interact with the user interaction module 624 through audio and/or verbal inputs and outputs. For example, in some embodiments, the user interaction module 624 generates sounds through which the monitoring system can provide instructions and/or information to a monitored individual and query the monitored individual for information. In some embodiments, voice recognition capabilities allow a monitored individual to verbally respond to requests for information.

Figure 7A:
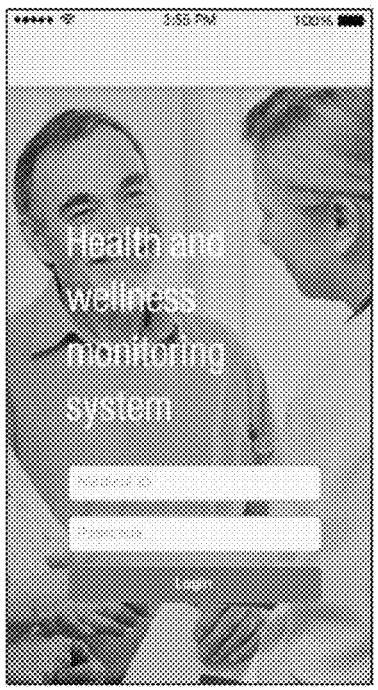
FIGS. 7A-7K schematically illustrate a plurality of examples of graphical user interfaces displayed by the mobile computing device of FIG. 6.

One non-limiting example of a graphical user interface generated by the user interaction module 624 is provided in FIG. 7A. As shown at FIG. 7A, in various embodiments of the monitoring system, upon downloading the health monitoring application 622 onto a mobile computing device 600, a login screen prompts the monitored individual for login credentials, including, for example, a username and password. The monitoring system 100 of various embodiments is configured to be secure, requiring every user of the system (e.g., including monitored individuals, supervisors, reviewers, and system administrators) to enter proper login credentials demonstrating authorization to use the system prior to interacting with the monitoring system. Following the initial download of, and log in to, the health monitoring application 622, the mobile computing device 600 may perform a method to search for, and communicatively pair with, a nearby sensor system 300. In future uses of the system, the mobile computing device 600 may automatically pair with the same sensor system 300 with which it previously communicated and may allow a monitored individual to provide and receive information related to data being acquired from the specific paired sensor system 300.

In some embodiments, upon logging into the health monitoring application 622 for the first time, the monitored individual is prompted to provide biographical information and/or a medical history. For example, the user interaction module 624 may prompt the monitored individual to enter one or more of a: name, identification code, gender, sex, date of birth and/or age, ethnicity, race, height, weight, and medications and/or supplements routinely taken. The information requested by the user interaction module 624 varies depending on the intended use of the monitoring system. For example, in some embodiments, the monitoring system is used for wellness purposes to track changes in circumference of a body portion caused by changes in weight, muscle mass, and/or fetal development. Depending on the intended use, the user interaction module 624 may modify its prompts, for example, in order to request that the monitored individual enter one or more of the following when relevant: desired fitness goals, desired weight loss or weight gain goals, current level of fitness, average amount of exercise performed, gestation age, etc. In other embodiments, the monitoring system is used for healthcare purposes to monitor for changes in circumference of a body portion caused by abnormal swelling. If the monitoring system was prescribed to an individual for use before or following surgery, the user interaction module 624 may request that the monitored individual enter information on the type of surgery and the date of surgery. Additionally or alternatively, in some embodiments, the user interaction module 624 generates prompts requesting that the monitored individual enter in risk factor data relevant to assessing the likelihood that the monitored individual will develop complications, for example swelling of the body portion. In some embodiments, the user interaction module 624 requests that the monitored individual select any clinically-relevant risk factors that apply to the individual. The risk factors may be presented in a list and may include, for example, one or more of: duration of injury, chronic or acute, pre- and post-surgical performance, surgical findings, paralysis, paresis, plaster immobilization of a limb, active cancer and stage of cancer malignancy and treatment, previous history of deep vein thrombosis (DVT) and/or pulmonary embolism (PE), family history of DVT and/or PE, obesity, history of smoking, heart disease, lung disease, inflammatory bowel disease, recent childbirth, pregnancy, blood clotting disorder, advanced age (e.g., over 70 years of age), and/or use of supplemental estrogen or birth control pills.

Additionally or alternatively, in some embodiments of the monitoring system, the user interaction module 624 prompts the monitored individual to enter in information related to a current health or wellness status and/or current or recent habits and activities. For example, the user interaction module 624 may request that the monitored individual enter in information related to one or more of: symptoms, a wellness rating, a pain rating, an exercise performed, a food consumed, a supplement consumed, a medication administered, a duration of sleep attained, and an indication of whether the monitored individual has complied with a prescribed instruction. The user interaction module 624 may prompt the monitored individual for such information on a regular basis (e.g., daily or hourly), upon each opening of the health application 622 on the mobile computing device 600, or upon detection of a change in status (e.g., a change in a circumference measurement reading or a change in acceleration).

Figure 7B:
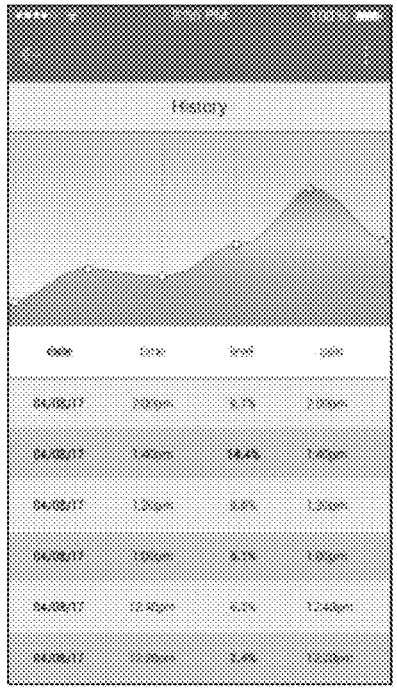
Figure 7C:

As shown in the non-limiting graphical user interfaces provided in FIGS. 7B-7C, the user interaction module 624 is also configured to provide information to a monitored individual. For example, the user interaction module 624 may enable the monitored individual to review his or her previously-entered medical history, current or recent measurements acquired from the sensor system, a history of the tracked measurements acquired from the sensor system (as shown in FIG. 7B), and/or health or wellness information. In some embodiments, the user interaction module 624 provides the monitored individual with access to a library of health and wellness information, for example, to a library of information maintained by a third-party provider, such as WebMD® or the Mayo Clinic® (as shown in FIG. 7C). In some embodiments, the user interaction module 624 provides the monitored individual with access to individual-specific instructions customized by the monitored individual's health or wellness professional (i.e., supervisor). The individual-specific instructions may include pre-operative instructions, post-operative instructions, instructions related to a diet or exercise regimen, or any other instructions the supervisor chooses to share with the monitored individual. The instructions may include, for example, notifications of suggested meals or exercises or reminders to sleep, exercise, elevate the legs, limit exertion, or take medications or supplements. In some embodiments, the user interaction module 624 provides the monitored individual with access to instructional videos, for example, videos demonstrating how to perform recommended or prescribed exercises or how to cook various recommended healthy meals.

Figure 7D:
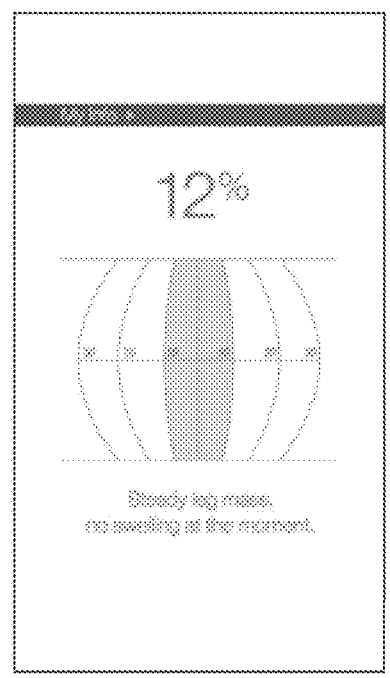
Figure 7E:
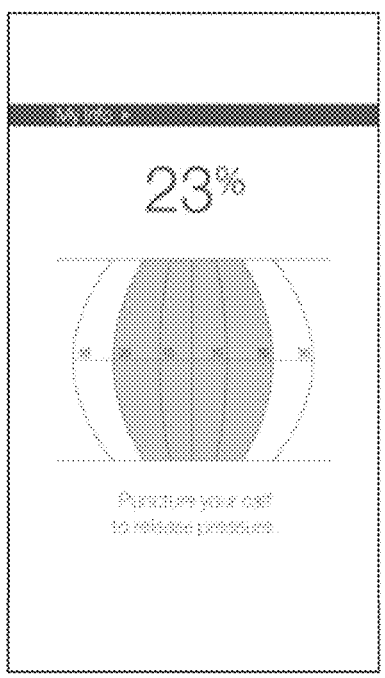
Figure 7F:
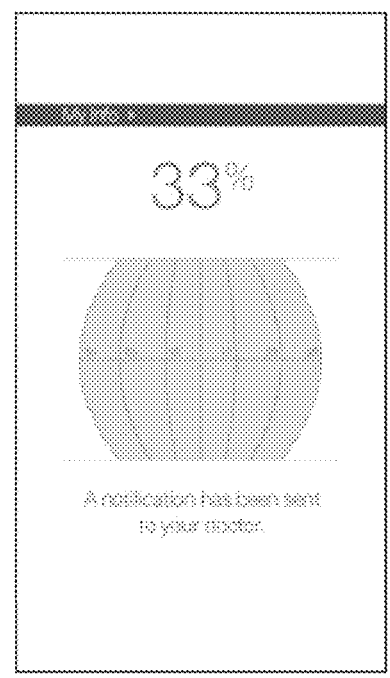

In various embodiments, the user interaction module 624 also provides information to the monitored individual in the form of alert outputs. The alert outputs may be generated at a regular interval or upon detection of a change in circumference or other monitored health parameter. The alert outputs may include notes of encouragement, notifications of progress, reminders of particularly relevant instructions, or an instruction to contact a healthcare provider. Three non-limiting examples of graphical user interfaces displaying alert outputs are provided in FIGS. 7D-7F. In each of FIGS. 7D-7F, the alert output includes a numerical and pictorial indication of progress and a message providing pertinent feedback. Additional users of the monitoring system, for example, supervisors and/or reviewers, may also be able to transmit messages to the monitored individual through the system, which are displayable in the graphical user interface of the user interaction module 624.

Graphical user interfaces (GUIs) may be integrated as part of an application or app configured to adapt to human behavior training and neuroplasticity. Examples of customizable adaptive user interfaces are illustrated in FIG. 7G-7K. GUIs may be configured to adjust patient behavior and assist in compliance with a required care plan. The monitoring system and graphical user interfaces may be constructed to develop a daily routine of self-care in accordance with a healthcare provider's care plan, which triggers action and engagement on behalf of the patient in response to given contexts. Contextual attributes may comprise any combination of: time of day, time in care episode (e.g., before surgery, after surgery, two weeks after surgery, day before surgery, etc.), patient behavioral profiles, and adherence level to a given care plan—for example, the monitoring system application may be configured to reduce a lack of adherence to an exercise protocol in the care plan by sending appropriate triggers to patients to establish or maintain engagement. Triggers provided by the monitoring system will vary based on the user/patient's psychological profile (e.g., motivated, disciplined) and will apply behavioral research paradigms such as the Hawthorne effect, change curve, and/or other behavioral or psychological elements to make patients more accountable to their healthcare prescribed care plan. For example, the app may employ methods of the Hawthorne effect by creating a system that may be monitored by another party more specifically by making patient specific information visible to care providers and caregivers and via generating contextually personalized messages from an ecosystem of caregivers.

In various embodiments the monitoring system may generate a patient profile. A patient profile may be built from sociological factors including the patient's social network. Connecting patients to the network, and integrating their network in a privacy compliant way with a patient's care team (e.g., family, friends, home care providers etc.) during recovery, may improve the one or more parameter of "social adherence" that may be monitored by the system as part of an adherence parameter and optimized for as part of the adaptive care plan. An adaptive care plan comprises any combination of the dynamically adjustable care related instructions provided by or supported by one or more individuals or entities external to the user/patient, including healthcare providers and supporting care providers (e.g., family, friends, home care providers, etc.). Depending on the patient profile, the system may be configured to prompt caregivers from the network to reach out to the patient periodically or when the patient's overall adherence level is low. Caregivers may choose to respond directly to the patient or use automated mechanisms to respond (e.g., via chatbots) if they can't engage in real-time and live.

Figure 7G:
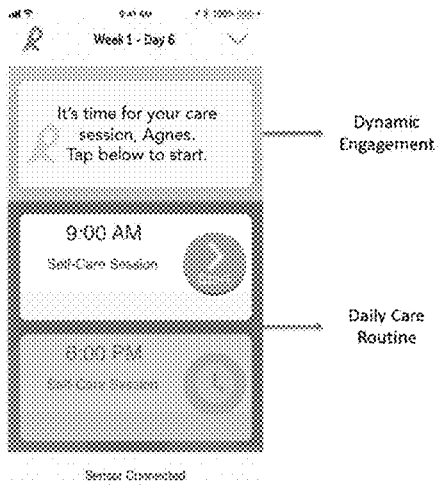

FIG. 7G illustrates how the app may be constructed to develop a daily routine of self-care in accordance with a healthcare provider prescribed care plan. The interface in this example is connected to a care plan comprising a schedule of activities for the user. In this example, the user is on Day 6 of Week 1 of the plan. The interface comprises 3 panels, one for Dynamic Engagement, and two associated with the Daily Care Routine. The user has not yet completed the morning portion of the Self-Care Session, which is scheduled for 9 AM. The Dynamic Engagement panel prompts the user (e.g., the user's name is Agnes) to "tap below to start" the morning session. A yellow circle comprising an arrow and the words "start" are highlighted to show the user where to press. The second panel associated with the Daily Care Routine is greyed out indicating that the user does not have access to this part of the Daily Care Routine, which in this example corresponds to an evening self-care session scheduled for 6:00 pm. At the bottom of the screen is an indicator that provides the user with feedback about the connection of the sensor (e.g., if the sensor is connected or not). In some instances, the connectivity of the sensor may be required and the light may need to be lit up before the user may activate the start sequence of the Self-Care Session. In other instances, activation of the Self-Care Session may walk the user through connecting the sensor if the sensor is not already connected.

In alternative or additional embodiments, the app may ask patients to make an explicit commitment to their care sessions, for example to drive ownership and autonomy. In alternative or additional embodiments, the app may be configured to enable the patient to follow a believe-know-act cycle such that the app helps patients transition through the states in this cycle. To get from "believing" to "knowing," the app delivers a framing for the information and context that resonates and makes intuitive sense. To get from "knowing" to "acting," the app may build in context sensitive, personalized prompting mechanisms. Finally, to get from "acting" back to "believing," the app may reinforce how the user's action make a difference.

In some embodiments, the application may comprise a contextual dynamic workflow with cloud integrated intelligence that may guide the patient or user based on user or patient specific controls (e.g., part of a cloud based care cloud). The application may be customized to the needs and disposition of the user (e.g., patient, athlete, etc.) such that the patient is lead through a self-managed care session that includes, for example, physical therapy, medication management, pain control, and holistic care. The flow of the app utilized by the patient may be adjusted dynamically based on one or more contextual (e.g., time or symptom dependent) parameters including: pre-operative readiness if the patient is in pre-op (e.g., getting ready with activities, exercises, and appointments); periodic symptom checking via the app in defined increments of time (e.g., 2 weeks) so that clinicians may intervene based on symptoms, pain management, and medication adherence in a defined increment of time (e.g., 3 weeks post-surgery), or until pain level is below a threshold and inflammation is in check; performance of prescribed exercise routine only when pain and symptoms are not present or of minimal concern.

Figure 7H:
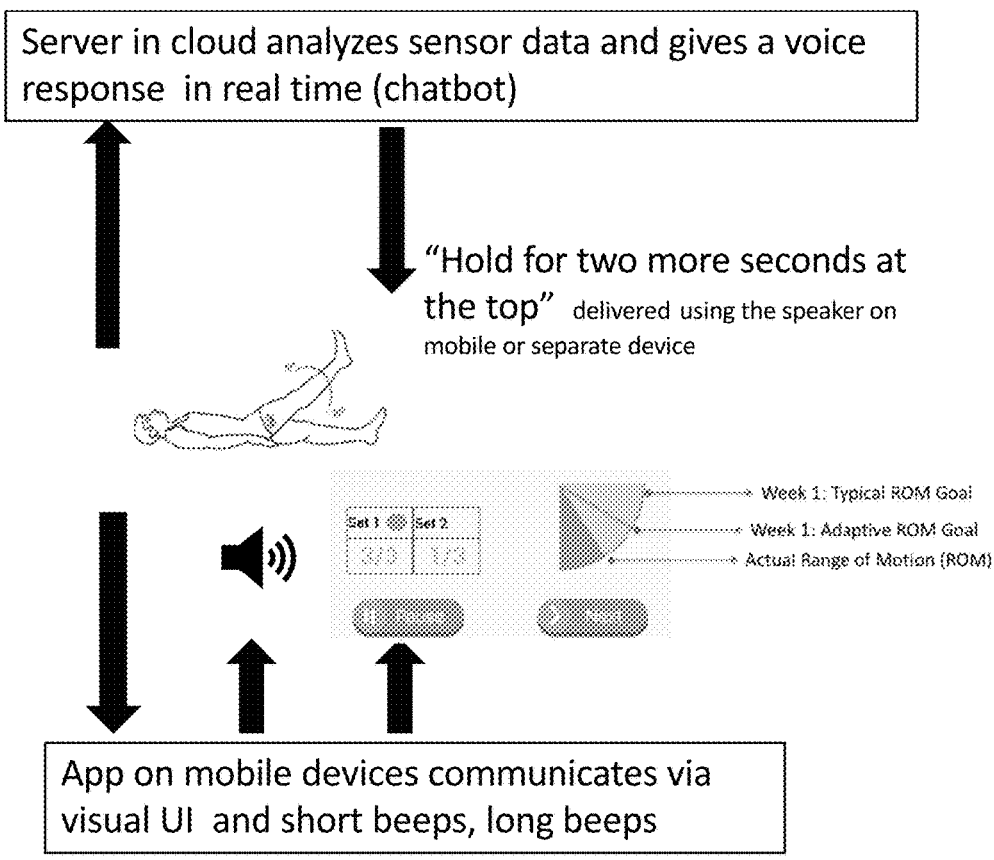

FIG. 7H illustrates an interface and information flow behind the interface, that is used to establish adaptive goaling and keep patients engaged while making progress. The interface is configured to adjust to the needs of the patient while also providing guidance as the patient performs exercises. The display comprises information about the sets being performed and the user's current status in the process. In this instance, a green dot with a checkmark indicates that 3/3 exercises of Set 1 have been successfully completed and the user has completed 1/3 of the exercise in Set 2. The user is currently engaged in the process because the button below the Set table provides the option of pausing the routine. To the right of the pause button is a button that may be used to move on to the next exercise in the routine. On the right-hand portion of the screen is an illustration depicting the range of motion for the particular exercise being performed and the relative performance of the user. In this case, the display shows the Week 1: Typical Range of Motion (ROM) Goal, the Week 1: Adaptive ROM Goal and the Actual ROM for the user. In some embodiments, the performance of the user may be captured and stored as part of the user's data on a cloud storage system (e.g., a care cloud). Captured data may comprise a range of the planar movements of the body when the patient performs habilitation (e.g., rehabilitation, pre-habilitation, etc.) exercises. Pre-habilitation exercises performed before a medical procedure may be detected, captured, monitored, and used to establish a point of reference or baseline for the patient. Rehabilitation exercises performed after a medical procedure may be detected, captured, monitored, and used to determine the current status and prognosis of the patient after the procedure as well as to determine the range of motion of the patient as a means of adaptively generating a care plan with next goals and steps. Adaptive goal setting may enable a patient to pursue achievable range of motion goals as part of their recovery plan. Furthermore, adaptive goal setting may prevent patients from getting dissuaded by standardized goals that may not apply to them. Pursuing goals that are over range or easily attainable by the user, may cause users to drop off from their care plan routine due to what they deem to be unnecessary (e.g., easily achievable) or completely out of reach (e.g., unachievable).

Figure 4O:
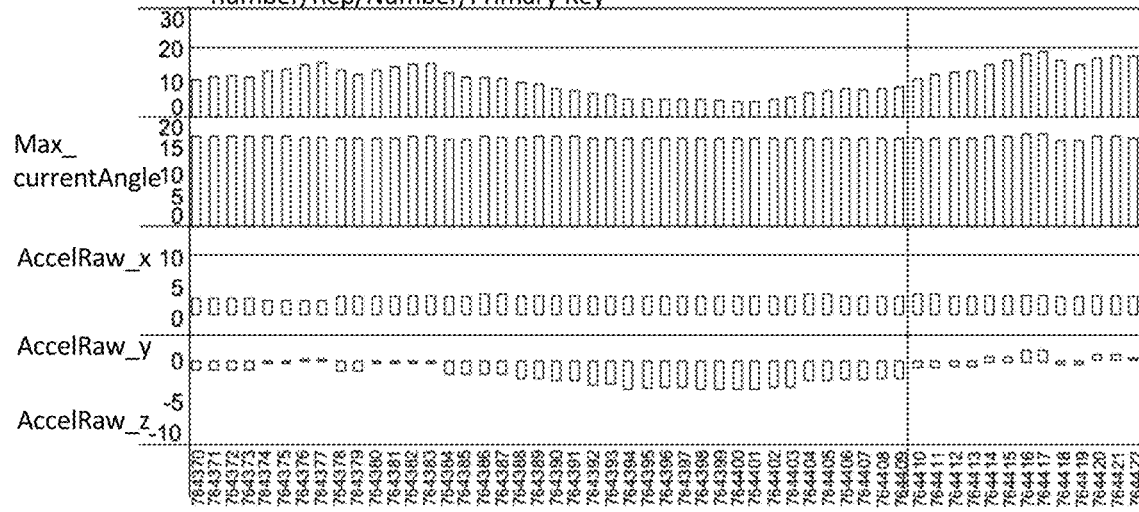

Also shown in FIG. 7H is the information flow for a patient using the mobile monitoring application and sensor containing device to perform and receive adaptive guidance on their exercises. In this embodiment, the application is interacting with audio cues from the patient and providing audio cues to the patient to facilitate effective performance of the exercises. The application on the mobile device communicates via the visual user interface and produces sounds of varying tone or duration based on the accuracy of the exercises being performed by the user. As the user performs the exercises, the server in the care cloud analyzes sensor data and provides vocal cues based on the user's immediate performance, for example if the patient was performing the joint extension exercises with the data shown in FIG. 4M-4O, then the care cloud could dynamically assess changes in strength, flexibility, range of motion, etc. and provide instructions to the patient according to their immediate performance; for example, if the patient approaches 60 degrees (see FIG. 4M/4N) appearing strong (e.g., has little movement in unintended planes (FIG. 4O), showing minimal shaking, etc.) then the application may provide instruction to the patient to hold the leg position at 60 degrees for 3 seconds; however, if the patient approaches 60 degrees appearing weak then the application may provide some other instruction for example it may reduce the number of reps or change the exercise in another way. A chatbot may be used to provide the instructions according to the patient actions as calculated by the sensor. A chatbot may also be used to respond to patients verbal questions or commands, including for example verbal commands to start or stop the exercises, and questions about performance relative to previous days, etc. Chatbots may comprise part of the monitoring application running on the mobile device, or external systems configured for interacting with the mobile device or monitoring system. Chatbots can comprise voice assistants including Amazon Alexa, Siri, Cortana, Google voice activated devices, etc.

Figure 7I:
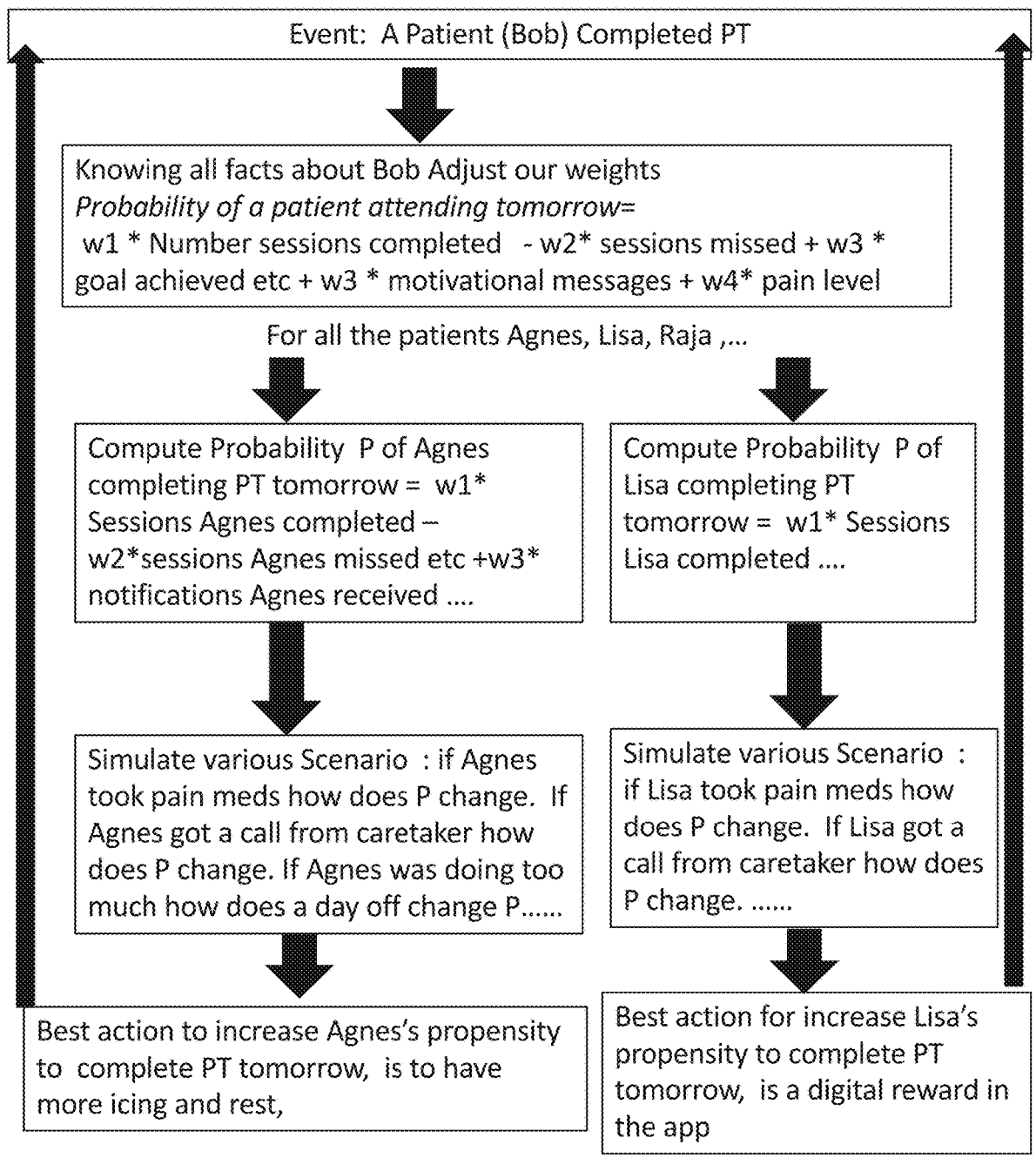

As previously mentioned, the user interface may comprise adaptive alert outputs. In some embodiments, alert outputs may be configured in response to a patient profile or one or more other features as shown in FIG. 7I. Adaptive alert outputs can comprise AI based game mechanics, or next-best-decision based methods for encouraging user's or patients to adhere to their care regimen. In some instances, AI based game mechanics may offer a user or patient specific rewards for continuing to use the system. User or patient specific rewards may be based on a user profile or user model generated to identify and weight one or more factors that influence the user's behavior and optimize for the desired user behavior (e.g., adherence and recovery). FIG. 7I illustrates a next-best-decision flow for a series of patients based on information obtained from a patient named Bob who successfully complete his physical therapy. Knowing all facts about Bob, the model adjusts weights to calculate a probability of a patient (e.g., Bob) attending physical therapy the next day. That value is calculated as the weighted sum of one or more factors. The one or more factors may include but are not limited to: number of exercise sessions or PT sessions attended, the progress in physical therapy based for example on the number of exercises completed, the number of exercises completed with the target ROM, response to motivational message, pain level, timeliness and regularity at specific times of the day, medication taken, medications taken and reported, medications not taken, physical condition, completion of checklists toward maintenance of a safe environment including preparing the exercise environment by securing carpet etc., and communications with caregiver and care team. Based on these factors and the corresponding weights known for Bob, probability of other patients (e.g., Agnes and Lisa) is determined from a weighted sum computed based on their respective performance. Various scenarios are computed for each patient (e.g., Agnes and Lisa) and a best action is determined that will increase the likelihood that Agnes and Lisa will complete their physical therapy that next day. The monitoring system then provides Agnes and Lisa each with their customized reward or suggestion. In FIG. 7I, for example, the system has computed that the best action for Agnes is to have more icing and rest, and the best action for Lisa is a digital reward in the app. The system adapts to each user specific trajectory and user profile to provide a reward or recommendation that will best support their successful movement through the care plan and towards recovery. Rewards or recommendations may comprise or rely on mechanisms disclosed in FIG. 1A-FIG. 1B as well as additional rewards or recommendations. Examples of rewards may include but is not limited to: posting the user at a position on a leader board; using digital goods such as a Hawaii theme, stars, balloons, etc. on the application; informational messages reminding the user of the importance of medication or physical therapy; notifications to do an activity based on a time limited period; and communications from caregivers or care team, such as a chat message or a call.

Figure 7J:
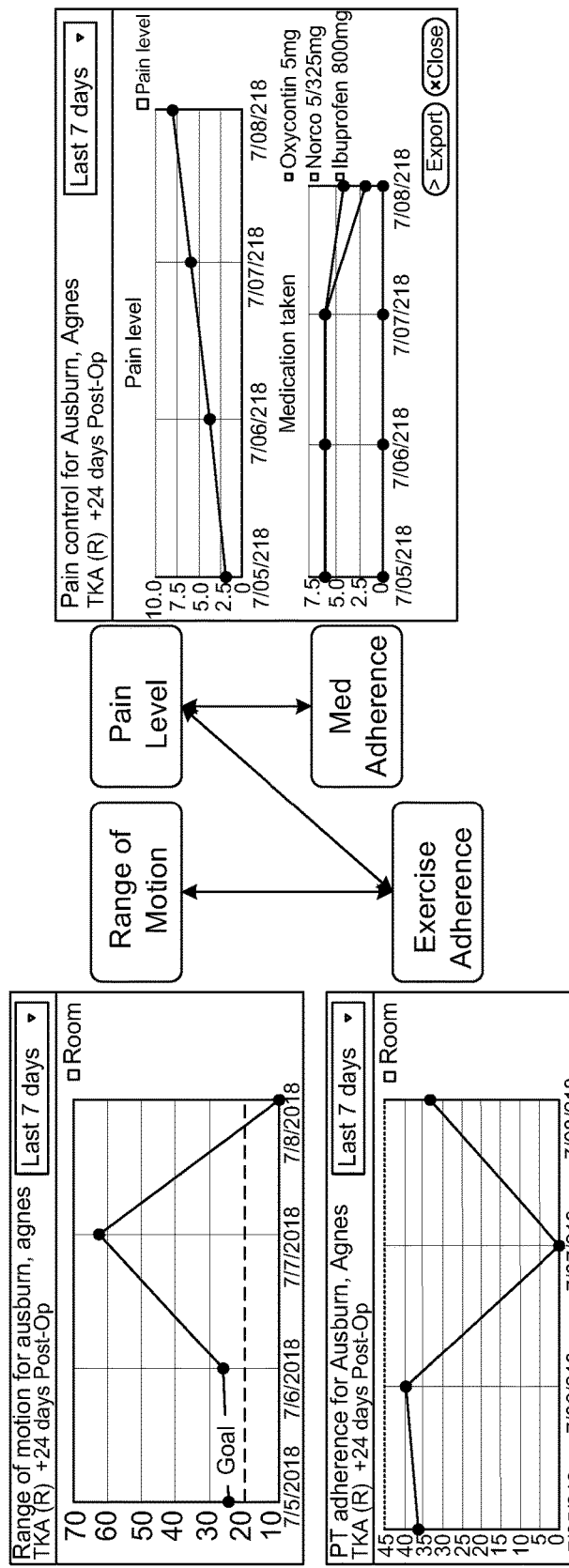
Figure 7K:
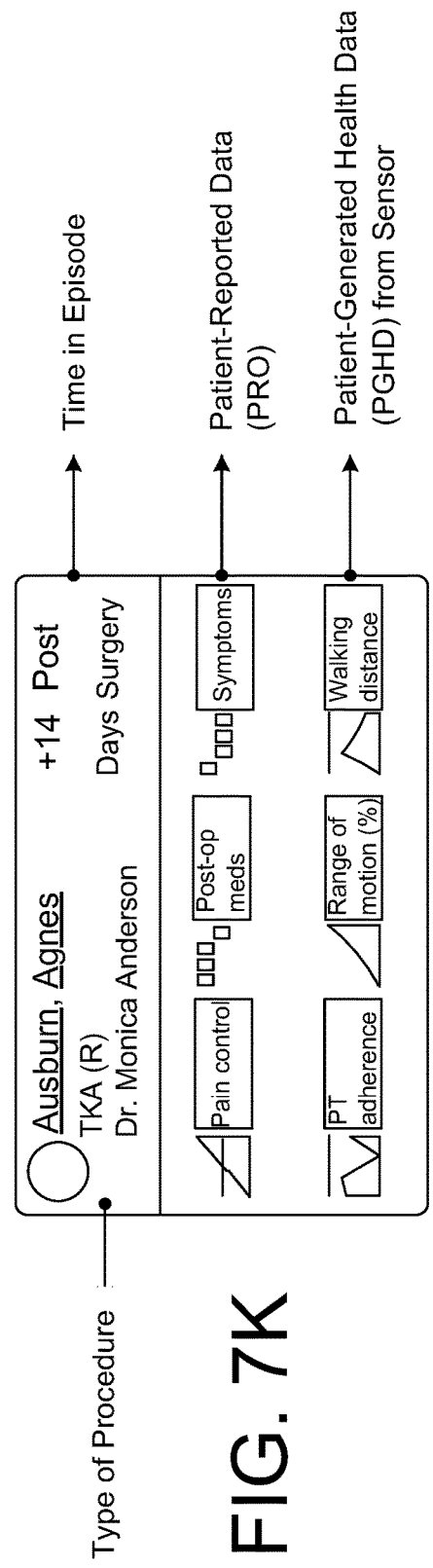

In various embodiments, a monitoring system may comprise a healthcare provider interface. FIG. 7J and FIG. 7K illustrate exemplary user interfaces and data flows for a physician or healthcare application. A healthcare provider interface may enable healthcare providers to set the user (e.g., patient) up in the monitoring system with a care plan, for example, an MSK care plan tailored to the needs and preferences of the user (e.g., the patient, athlete, etc.). A healthcare provider interface may provide healthcare providers with the ability to customize the user's care plans. In some embodiments, a healthcare provider interface may comprise easy to view patient-reported and patient generated data. Patient generated data may comprise data collected from one or more sensors and/or sensor containing devices utilized by the user. A healthcare provider interface provides healthcare providers with a status of a user's progression along the provided care plan (e.g., a medically approved health care plan). Healthcare provider interfaces may provide healthcare providers with alerts if the patient crosses one or more thresholds that have been set up by a healthcare provider for patient-reported and patient generated data.

FIG. 7J illustrates components of a healthcare provider dashboard. The dashboard is configured to support comparisons between the two or more components of a PRO or PGHD data. In this example, the dashboard comprises plots of the patient's medical adherence, pain level, exercise adherence and range of motion. Each plot displays data generated from multiple days. The dashboard is configured such that the relevant patient information can be displayed as separate graphs, as combinations of content on the same graph, and/or with scores or analyzed content distilled into metrics according to time (e.g., over a period of time or range).

FIG. 7K illustrates an "at-a-glance" patient card with patient-reported and patient-generated data from the sensor. In this embodiment, the patient's name is displayed with the type of procedure and the name of the doctor (e.g., Dr. Monica Anderson) displayed in the upper left corner of the card. In the right corner, the card displays the "Time in Episode," in this case the user is in the window of greater than 14 days post-surgery. The middle section of the card displays the patient reported data (PRO) with the indicated graphical display of pain control, as well as post-op Meds, and Symptoms reported by the user. In the bottom section of the card, patient generated health data (PGHD) from the sensor is reported in a graphical form as physical therapy (PT) adherence, range of motion (ROM, %) and walking distance. These cards may be configured for use by the user (e.g., patient, athlete, etc.) or by a physician or healthcare provider, for example as part of a healthcare provider interface or portal. In some instances, the physician or healthcare provider may sort, process, filter, or display the cards in a way that is useful to the routine or healthcare provider protocol procedures, to facilitate timely providing of care.

In various embodiments, an application may comprise one or more interfaces or graphical displays configured to encourage and/or sustain user (e.g., patient, athlete, etc.) engagement using gamification. The interface may be configured such that the display of content is customized according to the psychological profile of the user. Examples of customizable features of the display include but are not limited to the following: marquee icon change color to indicate engagement, adherence, and progress; app's marquee icon animates itself to engage patient and provoke action; rewards for patients may be provided for accomplishments such as repetitions completed or number of times sessions were done in a week; leaderboard to motivate users through competition and comparison with others; etc. Techniques may be used and customized according to a behavioral profile compiled for the user that may facilitate engagement of the user through display of the user interface such that the user is motivated to stay on the recovery journey.

In various embodiments, the application (e.g., monitoring system) may be configured to engage, activate, or trigger the participation of providers aside from the user (e.g., patient, athlete, etc.) to support and encourage the patient at critical junctures in the user's care or training plan. The engagement or activation of providers outside the user may be triggered by the Monitoring system in accordance with the user/patient's psychological profile (e.g., motivated, disciplined, etc.). The application may be configured such that a suggestion or suggestions may be provided to a caregiver or outside provider at user specific critical junctions in the care process, with suggestions to the caregiver or outside provider that are custom tailored to assist the patient in a way that supports the user's accountability for their care. In further instances, the application may comprise a bot or trainable automated response system that may engage with the user according to the user's psychological profile. In further embodiments, bots may be employed in response to input from a designated caregiver or outside provider—for example if the caregiver or provider is unable to attend to the user's needs in a way (e.g., within a time frame) that is necessary for the user (e.g., according to the user's specific needs or profile). In some embodiments, the application may comprise a mechanism for facilitating communication between the user and an outside provider or caregiver (e.g., messaging system integrated with functionality of the application—including for example various means of communication including audio, picture, video, etc.).

The information requested from, and provided to, the monitored individual is customizable based on the intended use of the monitoring system. In some embodiments, it is customizable by a system administrator. Additionally or alternatively, in some embodiments, it is customizable by a healthcare provider, athletic coach, personal trainer, or other health or wellness supervisor.

Figure 8:
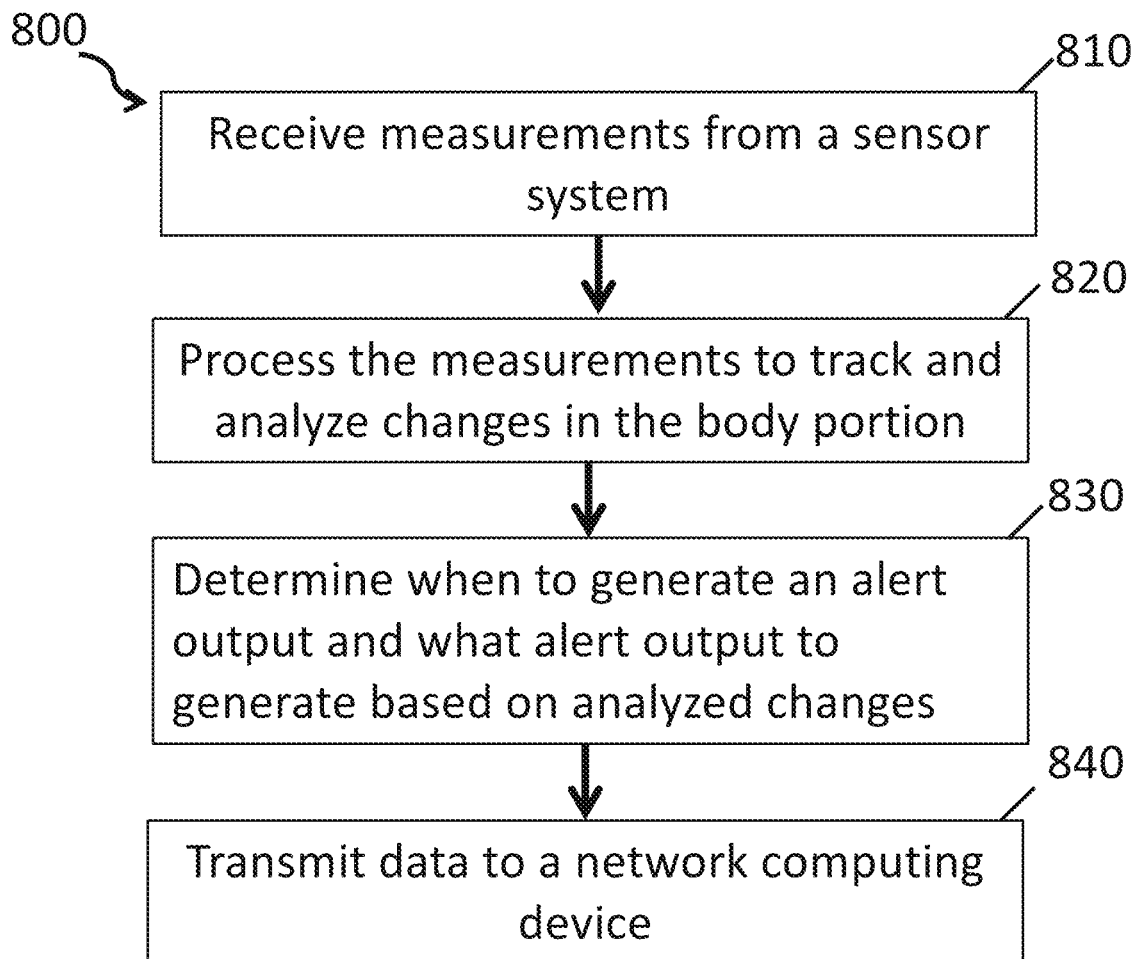
FIG. 8 illustrates a flow chart of one embodiment of a method performed by the mobile computing device of FIG. 6.

The health application 622 of various embodiments also includes a data processing module 626. The data processing module 626 includes the software that instructs the mobile computing device 600 to perform various data processing methods. One method directed by the software of the data processing module 626 is depicted in FIG. 8. As shown at block 810 of the depicted method, the mobile computing device 600 receives measurements from the sensor system 300. As described above, these measurements may be relative or absolute measurements. The measurements include circumference measurements of the body portion, positional measurements, orientation measurements, or measurements indicative of circumference. In some embodiments, the raw measurements (such as measurements of changes in resistance, capacitance, or inductance) are received by the mobile computing device 600 from the sensor system 300 and processed by the mobile computing device 600 to determine circumference, position, and/or orientation. Additionally, the measurements may optionally include one or more additional measurements of health parameters such as orientation, acceleration, range of motion, skin temperature, skin color, and/or cardiovascular performance (e.g., blood oxygenation, blood volume, pulse rate, or heart rate). At block 820, with the aid of the data processing module 626, the mobile computing device 600 processes the received measurements to track and analyze changes in the body portion. Additionally, the mobile computing device 600 determines when to generate an alert output and what alert output to generate based on any analyzed changes to the body portion, as shown at block 830. The mobile computing device also transmits data, including the received measurements, the analysis of measurements, and data received via user inputs, to a network computing device, as shown at block 840.

In some embodiments, processing the received measurements to track and analyze changes in the body portion involves assigning a relative weight to one or more measured parameters of importance and calculating an overall score from the weighted measurements, as described elsewhere herein. Additionally, one or more user inputs and/or a compliance score may contribute to the overall score.

In some embodiments, the compliance score is also calculated by the mobile computing device 600 using the software of the data processing module 626. The compliance score is an indication of the degree to which the monitored individual complied with prescribed instructions. The compliance score may be calculated based on one or more of: the change in circumference of the body portion, the user inputs, detected motion of the body portion indicative of an exercise, a detected orientation of the body portion, a range of motion of a body portion, a quantity of prescribed exercise performed, and a quality of prescribed exercise performed. For example, if the prescribed instructions include an instruction to upwardly tilt or elevate the legs, the compliance score may be determined, at least in part, by monitoring leg orientation. If the prescribed instructions include an instruction to perform leg exercises, the compliance score may be determined, at least in part, by monitoring leg movement, and optionally calculating a number and quality of leg exercises performed. If the prescribed instructions include an instruction to administer a medication, the compliance score may be determined, at least in part, from a user-entered input indicating medication administration.

In some embodiments, the mobile computing device 600 using the software of the data processing module 626 may apply one or more algorithms for patient engagement, adherence, and progress tracking. In some embodiments, algorithms for patient engagement may be run on a cloud (e.g., care cloud) or a server that is not located on the device using data collected from devices or systems disclosed herein. Patient engagement algorithms may be generated using unsupervised, supervised, or semi-supervised methods. In some instances, patient engagement algorithms may be generated using neural networks. Patient engagement algorithms may be generated based on positive performance outcomes, for example based on parameters that produced positive outcomes from previous patients or based on deductions or analysis conducted by medical professionals.

Figure 13C:
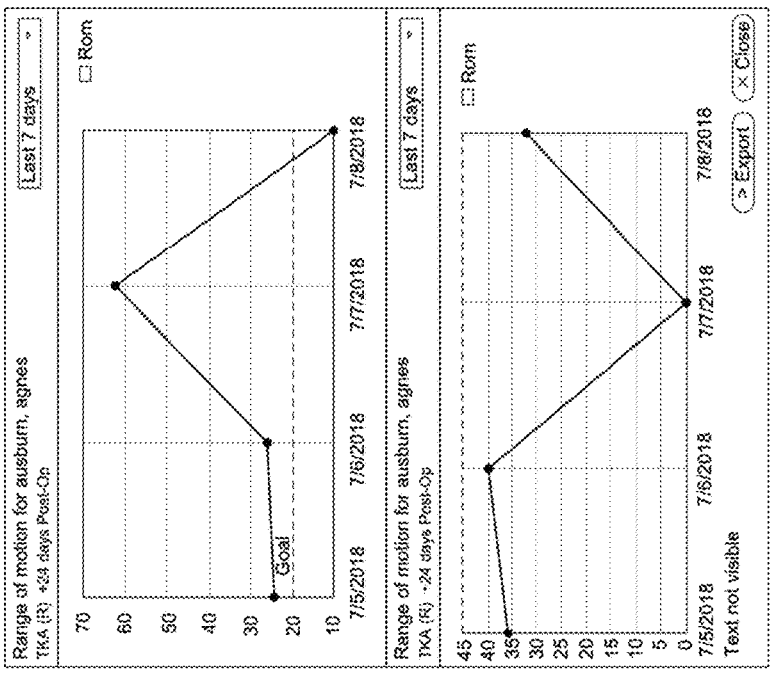
FIG. 13A-13C illustrates inputs to the system and dynamic adjustment and readjustment of predicted progress based on the inputs.
Figure 13A:
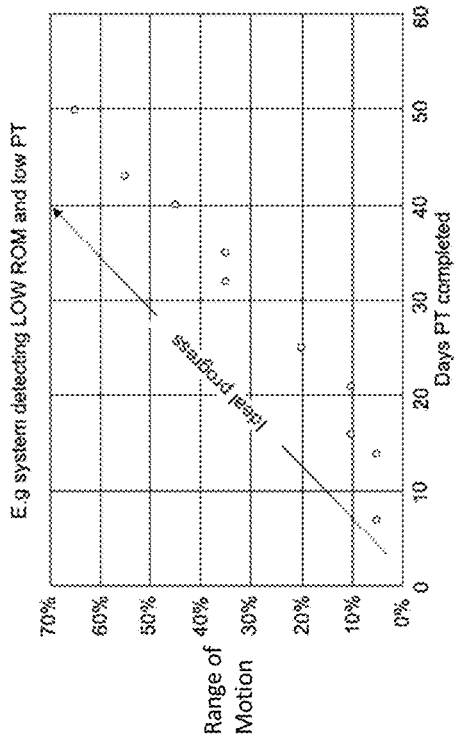
Figure 13B:
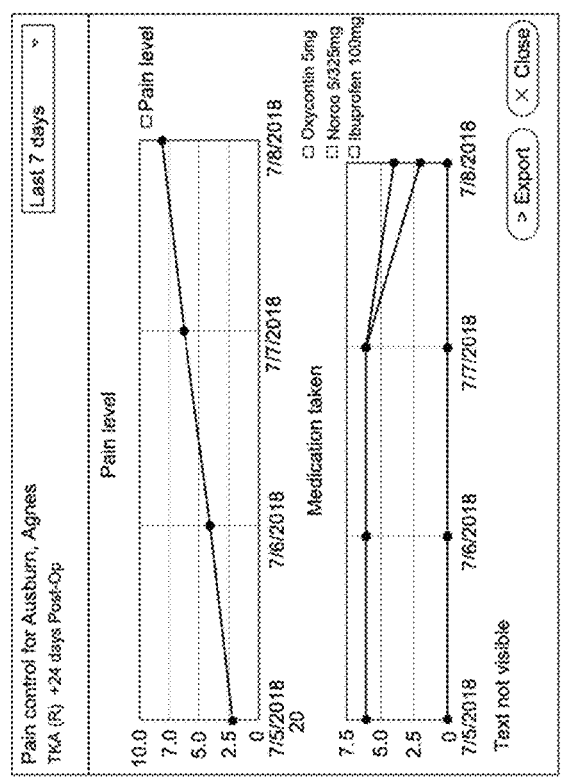

Monitoring systems as disclosed herein may comprise dynamic progress charting, such that the progress in a care plan, including towards care goals (e.g., ROM, pain reduction, etc.), can be measured and adjusted based on incoming data. The monitoring system may collect hundreds of features and inputs that update performance dynamically. In FIG. 13A, an example of ROM is shown deviating below normal in relation to physical therapy (PT), however hundreds of features could be used in addition to the two illustrated in this example. The monitoring system learns ideal progress from a patient at defined time increments (e.g., every 6 hrs, 12 hrs, 24 hrs, 36 hrs, 48 hrs, etc.) from all patients. The monitoring system is dynamically adjusted, as shown by the dots of the plot in FIG. 13A. The dynamic adjustment performed by the monitoring system exceeds performance of current medical methods, which apply a fixed/static trajectory and path of ideal progress to all patients regardless of their unique dispositions or conditions, thereby providing a less accurate prediction with little if any means for guiding or optimizing care to the particular patient or user. FIG. 13B and FIG. 13C show exemplary information that may be factored into the prediction shown in FIG. 13A to enrich and better predict and inform the next-best-decision approach to generate an adaptive care plan.

In some instances, algorithms may be run as part of the care cloud such that the care cloud may perform statistical analysis and generate predictions for a single user or groups of users based on correlations between the data provided by a given patient/user and the body of data and models that have been previously generated and have known outcomes. Examples of correlations that may be made as part of the care-cloud analysis comprise correlations between range of motion and exercise are shown in FIG. 14A.

As shown in FIG. 14A, the application may recognize patterns in the tracking data obtained from the sensor as the sensor monitors the planar movements of the body across sagittal, transverse, and coronal planes. The sensor tracks all types of movements and measures the degrees of flexion, extension, abduction, and adduction for any exercise prescribed by a healthcare provider (e.g., physical therapist, etc.) and records repetitions of completed exercises against the prescribed total. The care cloud captures the repetitions and range of the planar movements of the body when the patient does pre-habilitation exercises and creates a point of reference or baseline for the patient. The sensors detect and record the ranges of planar motions of the user/patient post-MSK procedure and the recordings are transferred to the care cloud where the care cloud may correlate the repetitions done over a period of time to the range of motion (ROM) improvements as well as monitor other aspects of the user's performance including strength and endurance. By comparing pre-habilitation benchmark data with post-operative exercise data, the patient's recovery against a pre-operative baseline and improvement beyond a pre-operative baseline or pre-injury baseline may be established quantitatively. The care cloud may generate alerts if there are deviations to the thresholds (e.g., deviations from thresholds determined and set up by a healthcare provider) for the patient-reported feedback and patient-generated sensor data. Based on one or more of: the care plan, the performance of the user, and the thresholds set by the healthcare provide, the care cloud may trigger the patient through personalized messages to act based on adhering to an exercise protocol in the care plan. The care cloud may also trigger caregivers and supporting friends or family to provide empathetic support (e.g., Empathetic Guidance) for the patient in his/her adherence to an exercise protocol in the care plan.

The monitoring system, using the care cloud and/or care related algorithms, may identify correlations between pain medication and pain levels for a given user, as illustrated in the example of FIG. 14B. In this example, the care cloud generates alerts if the patient-reported data on medication adherence and/or pain level exceeds or does not reach a given threshold set up by a health care provider. In further embodiments, these alerts may be displayed on a healthcare provider interface. The monitoring system may, using inputs regarding pain medication and pain level, also alert clinicians if a patient is not taking mandatory medications such as blood thinners or not taking medications needed to counter symptoms such as constipation when those symptoms are reported by the user/patient. The care cloud may engage with the patient through personalized messages to act based on the predication prescribed by the healthcare provider as part of the user/patient's care plan. The care cloud may also trigger the caregivers or supportive friend/family to get them engaged in supporting the patient and their adherence to pain management in the care plan.

The monitoring system, using the care cloud and/or care related algorithms, may identify and correlate pain and medication with range of motion (ROM) detected by one or more sensors. As shown in FIG. 14C, the care cloud may correlate the medication adherence to the pain level as well as exercise adherence and ROM improvements. Absent contraindicated symptoms, patients that manage pain well may be exercising as prescribed to achieve clinical outcomes. In some embodiments, deviations from the predicted progression for a given patient as illustrated in FIG. 14C may cause concern and activate a message to the user/patient's care team and/or healthcare provider.

The monitoring system, using the care cloud and/or care related algorithms, may perform patient segmentation and comparison to assess and categorize the user/patient, and accordingly generate useful reminders or psychological support that may facilitate a user/patient's recovery. As shown in FIG. 14B, the patient may be assessed according to the likelihood of one or more of a set of risks including, but not limited to, fall risk, adherence risk, and readmission risk. These risks may be dynamically assessed according to feedback provided by the sensors as well as input provided directly by the user/patient. Risk stratification may also be performed by the care cloud, for example the care cloud may process the user/patient's response to a digitized list of questions that enables the healthcare team to determine the patient's potential risk after a procedure. The care cloud may compute the risk propensity of the patient and deliver the information to the healthcare team based on well-known clinical research (e.g., DVT risk, readmission risk, etc.) using characteristics of the patient or the patient's history. The care cloud delivers the outcomes of the risk stratification for the user/patient to the healthcare provider through the healthcare provider interface.

In various embodiments, patient engagement algorithms may use patient progress and episode timeline to reinforce adherent behavior for patient and provide actionable insights for healthcare providers. Patient engagement algorithms may result in contextual and personalized messages to patients that assist in helping them engage with, adhere to, and progress physically through a care plan.

In various embodiments, an engagement algorithm may be part of an AI (artificial intelligence) engine. As shown in FIG. 14C, the AI engine may comprise three levels or tuples for providing a context for a particular user (e.g., patient context), and assessing a corresponding care regime for said user. A patient context may comprise three elements or tuples (3-tuple system): time, adherence, and user/patient personality type; these three elements may be used to generate a customized and adaptable care plan for a user. The element of time may comprise a time in a particular episode or in a given day. The element of adherence may comprise one of three characteristics: engaged, adhering, and progressing. The exemplary progression of a user's adherence is shown in FIG. 14D, which illustrates the state for a patient at any time. As illustrated in FIG. 14F, four stages of a user are as follows: a user is connected when the user uses their phone to login to an app, the user is "engaging" when the user uses the app a certain number of times a week, the user is "adhering" when the user uses the app to report symptoms, pain level, medication taken, exercises, etc. and finally the user is "progressing" when the user shows the improvement in pain level and/or range of motion (ROM). The third element or tuple relates to the user/patient personality type, a user may fall in one of three categories: motivated, amenable, and not motivated.

The tuple at any instance has attributes that allow mapping the patient into a recovery curve as shown in FIG. 14E. An AI (artificially intelligent) model may comprise steps for computing and assessing patient performance, status, compliance, adherence, engagement, progress, etc. using a recovery curve. In some instances, a recovery curve may comprise a sigmoidal shape as shown in FIG. 14E, with variations in pain level and ROM (range of motion) as outputs based on inputs to the 3-tuple system. Each tuple of the 3-tuple system may represent a given feature of the model being generated and the curve (e.g., sigmoidal curve) may represent performance of a particular user such that the user may be assessed according to a model represented by the sigmoidal curve, with thresholds and benchmarks established based on outcomes or feedback provided by the previous users of similar characteristic. In some instances, a clinical outcome of a successful recovery may comprise positive (e.g., increasing) measure of range of motion and negative (e.g., decreasing levels of pain). For example, a positive outcome may include no pain when knee is flexed from 0 to 135 degrees; and no pain when knee is extended from 90 to 0 degrees. The model may be constantly refined using additional patient data as more patient data is accumulated and analyzed. Once a benchmark model is in place, machine learning classification methods may be used to determine performance of any given user going through the recovery cycle. Customizations associated with a given user's path through the system may be delivered in accordance with the user's performance according to the model and the 3-tuple system. The user's performance may be constantly updated and dynamically assessed to adjust and adapt to the current state of the user at any given time. The AI model and classification based on the AI model may be used in conjunction, or run on and/or with data obtained from the care cloud such that context-based "next-best-action" decisions (e.g., next-best-action decision tree) may be made at any instant in a particular recovery period.

The monitoring system may use one of the following machine learning models: Gradient Boosted decision tree, logistic regression, and support vector machines. The monitoring system, including components of the care cloud, may comprise one or more algorithms. In some instances, one or more of the models is initialized with known risk factors such as age, weight, gait, etc. for the patient. In a tree based model, the weights on each branch are initialized such that the tree outputs a probability of meeting the next day goal in recovery. The monitoring system may incorporate a recovery or recuperation model. As the patient goes through recovery, each piece of data is fed into the model and the model learns. The data could be physiological measurements, the adherence to the exercise protocols, the medical history, social activity of the patient, as well as answers to questions about feeling or well-being. In a tree based model, the weights of the tree are constantly adjusted at frequency intervals. Frequency intervals may comprise durations of less than or equal to 24 hours, 16 hours, 8 hours, 4 hours, 2 hours, 1 hour, 30 minutes, 15 minutes, 10 minutes, 5 minutes, 1 minute, 30 second, or 1 second.

The monitoring system may comprise a method of determining the outcome of a patient for the entire recovery trajectory of the patient, generating a recovery trajectory that could not otherwise be generated from the simple inputs of initial factors on the day of and the day after an operation—as is currently the case in current medical literature. The models used in the monitoring system are configured to collect both PRO and PGHD at intervals and over time periods, and extract information about the progress of the patient, such that the system may predict and provide an appropriate path to recovery. For example, a patient may begin using the application before a surgical procedure. Relevant information may be extracted from the sensors data (PGHD) and the patient provided responses (PRO) enabling the system to generate a baseline. Notifications may be provided to the user to assist in the preparation for the procedure. After the procedure, the PGHD and PRO data will be collected and compared to the baseline information collection from the patient prior to the procedure. Initially, the system makes an assessment based on information received by the patient, and over time the initial weights of the system are adapted to the behavioral data provided by the patient (e.g., the PGHD and PRO) such that the initially provided information (e.g., age of the patient, etc.) would be less represented by the weights of the system than the performance of the patient on the physical therapy exercises and the relative range of motion demonstrated by the patient. Furthermore, the model may be configured to assess a probability of completing physical therapy on or by a particular day, given the trajectory of performance of the patient and the PGHD and PRO data. The application may perform various simulations based on adjusting (e.g., increasing/decreasing) one or more factors (e.g., adherence, performance, compliance, etc.) to determine the best action for the system that will bring the probability of completing physical therapy on or by a particular day closer to 100%. The next best action may differ between patients, and the Monitoring system collects data and inputs and customizes the response according the patient and the PGHD and PRO data collected about the patient such that the next best action for one patient could be to taper down physical therapy exercises and, for another patient, the system under similar initial conditions (e.g., demographic factors and similar initial pre-operation and immediately post-operation factors) may recommend that the patient performs additional physical therapy exercises. For another patient with similar initial conditions, the monitoring system may suggest that the patient spend more time with their family and engage in activities that support and/or encourage them. The monitoring system is configured such that it may collect and assess physical, behavior, and psychological factors and integrate these factors into a patient profile and an ongoing care plan that establishes them on a customized and adaptable trajectory for progress and recovery.

A next-best-action feature of the monitoring system (e.g., decision model, next-best decision tree, or other machine learning based algorithm) moves the patient through a recovery curve by ensuring that the user (e.g., patient, athlete, etc.) is in one of a set of states and/or sub-states at any given time. States that may be included in a "next-best-action" decision tree may comprise: risk stratification, medication adherence, pain management, checklist for preparation for surgery, customization of checklist to personalized care plan based on patient profile, education/quick reference library, daily tidbits for patients, combination of voice-based and touch/vision-based capture of patient-reported data, and adaptive goaling to keep patients engaged while making progress.

Risk stratification may comprise the delivery of a digitized list of questions to the patient, which enable the healthcare team to determine the patient's potential post-procedure risk. In some instances, the care cloud may collect and store the data, and perform an assessment to compute the risk propensity of the patient, while also delivering the information to the healthcare team. The outcomes of the risk stratification may be used by the healthcare team to create a customized care plan for the patient after the procedure.

Medication adherence may comprise one or more features of the application, which involve reminding patients to take their medication. The care cloud may collect and store data about the medication adherence of a particular user, and may enable the healthcare provider to customize the medication for each patient. The app may enable the user (e.g., patient) to log the amounts of medication that the user took, and in some embodiments, may enable the user to also record symptoms experienced that may or may not be related to the medication taken by the user.

Pain management may comprise one or more features of the application, wherein the application is designed to deliver a holistic pain management module that coaches users through simple techniques to manage their pain. The app may periodically query the users on their level of pain. Examples of pain management modules that may be activated by a user or healthcare provider may include routines of pain medication, icing of a body portion, elevation of a body portion, and alternative pain management techniques.

Checklists for preparation for surgery may be included in the application and provided based on the next-best-action decision tree or care protocol. The application delivers a personalized checklist to the patient to enable them to prepare for surgery. A personalized surgery preparation checklist may comprise medical instructions prescribed by the healthcare professionals and instructions to prepare their home, pack for the hospital and transportation after the surgical procedure. The checklists may be time based, and provided in multiple steps leading up to the day of surgery. A user (e.g., patient) may be reminded to complete the tasks using reminders provided in the application and asked to check off completed items.

The application may be configured to provide customization of a checklist to personalize a care plan based on a user's (e.g., patient's) profile. Customization may comprise delivering a customized checklist for symptoms after a procedure. Customization may be performed by one or more healthcare providers. In some instances, a checklist may be driven by risk stratification of patients prior to the procedure/treatment. A checklist may be presented to the patient as part of a curated care session. In some instances, elements of the checklist are presented to the patient on a periodic or ongoing basis.

Educational and quick reference materials may be provided to a user through the monitoring application. In some instances, the application may maintain a set of content for the patients that are available for the patient to look up. Content may comprise: "how to" guides to prepare before surgery, a set of "how to" instructions post-surgery, and a detailed care plan so that users/patients know what to expect.

Relevant and personalized daily tidbits may be delivered via the application to keep the user experience fresh and informative. Tidbits may comprise education content including: content tailored by what a patient needs to do a better job with, module overviews to set user expectations, prompts for one-time tasks (e.g., pre-habilitation preparation, exit survey, etc.), motivational stories (e.g., successful patient case studies) with customization that ensure the user is similar to the provided case study, light hearted images/ messages when cheer is need (e.g., customized to when the user may be frustrated by progress or experiencing pain, etc.), tidbits created by the user's support team (e.g., friend and family members, etc.) including, for example, pictures of the user's grandchildren with motivational messages, trend analysis to deepen self-reflection (e.g., customization may comprise identifying positive/negative trends and provide corresponding feedback for self-reflection), and milestone based celebrations (e.g., customization may include feedback on positive milestones including driving, using cane, etc.).

Customization of voice-based and touch/vision-based capture of patient-reported data may be used to facilitate interaction between the application and the user and healthcare providers. In some instances, the application may be configured to support patients sending pictures of a surgery site to a healthcare provider. In some embodiments, the patient may send a picture of an exercise being performed to a healthcare provider and the patient may virtually consult with the healthcare provider to get feedback. Patients may communicate over audio and/or video with healthcare providers, as well as with their support team including family and friend caregivers. In some embodiments, the patient may respond by tapping on the phone or the sensor and that is captured as part of the patient input. A patient may speak to a voice-based system (e.g., amazon Alexa, or Siri, Cortana, etc.) and enable the system to capture input from the user.

Adaptive goals (i.e., adaptive goaling) may be included as part of the application to keep users engaged while making progress. In some embodiments, the care cloud may capture the range of the planar movements of the body when the patient does rehabilitation exercises and may, from the captured data, create a point of reference or baseline for the patient. In some instances, the care cloud captures the range of the planar movements of the body post-MSK procedure. The care cloud may determine the range of motion of the patient and adaptively create the next goals for the user to reach. Adaptive goals enable customized assessment of the user's performance such that the user/patient is provided with a care plan comprising achievable goals (e.g., range of motion goals) as part of their recovery plan. Adaptive goals prevent patients from getting dissuaded by standardized goals, and therefore dropping off from their care plan routine due to goals they deem to be unachievable—adaptive goals also allow healthcare providers to continuously monitor and assess the performance of a user relative to predicted expectations, as a way of determining the overall progression of the user in their recovery and relative to other similar users that have been through and/or are going through similar recovery.

Various data-based feedback loops may be involved in gathering data from the patient. In some embodiments, the monitoring system may capture patient data and allow information to be selectively shared by the patient with an ecosystem of providers using a distributed ledger system or blockchain. The distributed leger system may provide encrypted protection on networks such that data is preserved and protected. Providers that may be part of the blockchain include care providers (e.g., hospitals, physicians etc.), insurance providers, software-based service providers (e.g., wellness analytics providers, nutritionists, etc.), and dentists (e.g., for prophylactic antibiotic prescriptions during dental procedures). A blockchain based system may comprise the following: non-repudiable health records with multiple validated copies, electronically "notarized" records that are authenticated by initiating service providers, de-identification of data exposed to ecosystem of providers, time access to data with expiry of access (e.g., 30-day access, or 2-week access), always enabling control at the individual on when to share what data and with whom, and revoke access at any time to data (e.g., "patient's right to be forgotten"). A data store may be kept in blockchain with delineation between personally identifiable data elements and not personally identifiable elements.

Figure 15:
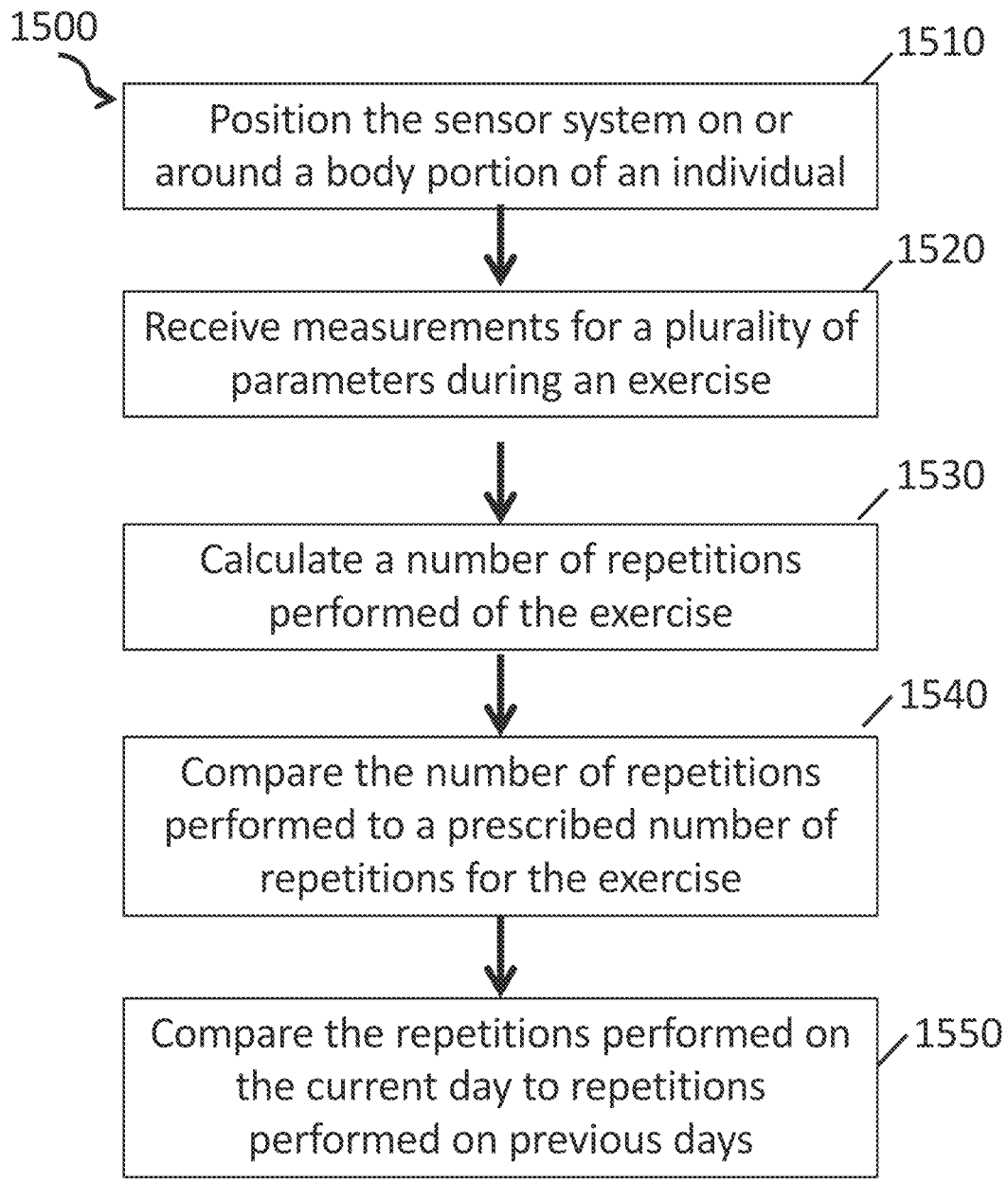
FIG. 15 illustrates a flow chart of one embodiment of a method for measuring a number of repetitions performed of an exercise.
Figure 16:
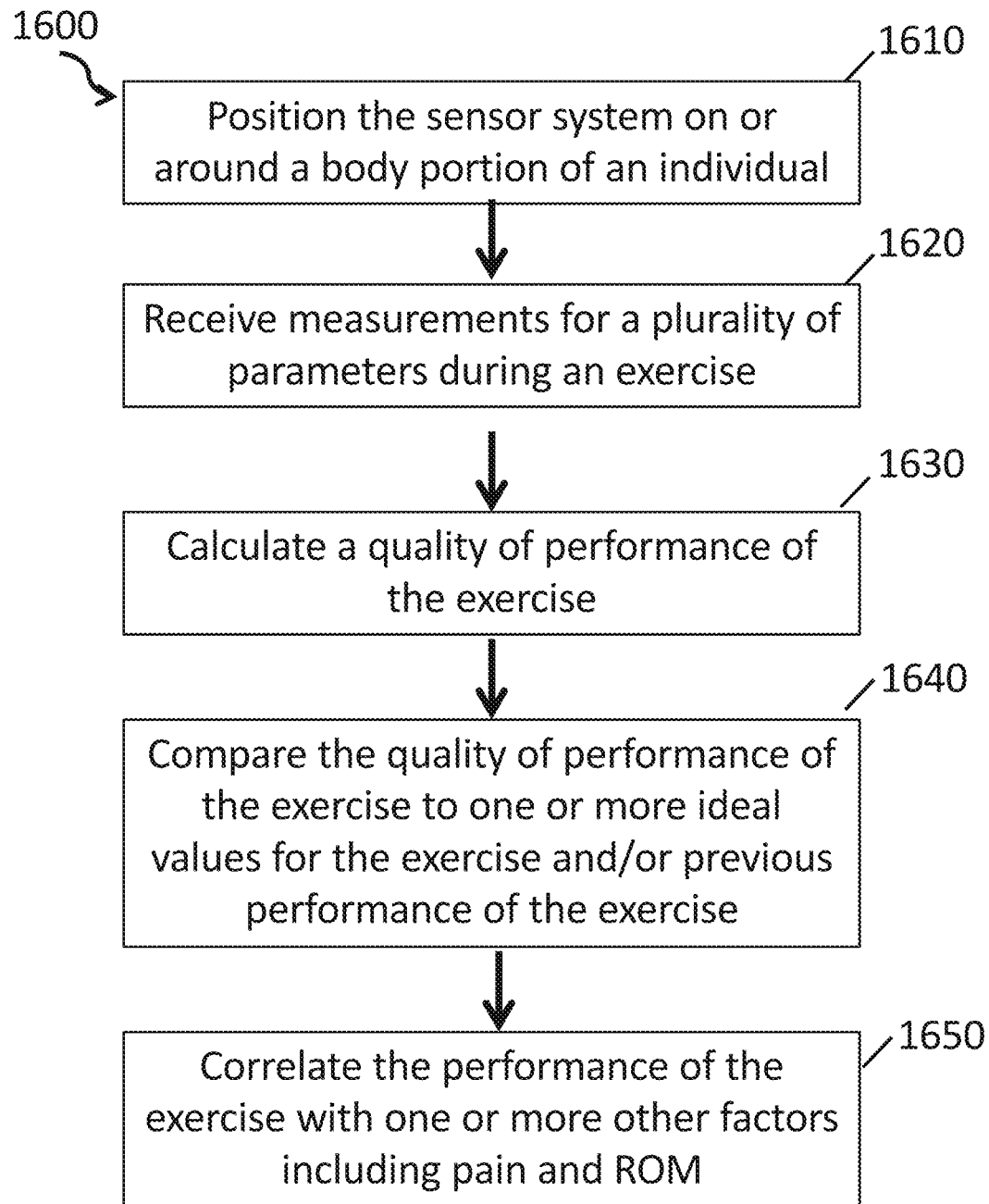
FIG. 16 illustrates a flow chart of another embodiment of a method for measuring a quality of performance of an exercise.

In some embodiments, as shown in FIGS. 15 and 16, a quantity or quality, respectively, of the exercise performed may be included in the adherence score or calculated as a separate indication of overall exercise performance. A method 1500/1600 for calculating a quantity or quality of an exercise or a prescribed exercise includes blocks 1510/1610, which recite positioning the sensor system on or around a body portion of an individual. At blocks 1520/1620, the method includes receiving measurements for a plurality of parameters during an exercise or a prescribed exercise. As described in FIGS. 15 and 16, the sensor system is positioned on or around an arm, leg, torso, ankle, wrist, chest, or any other body portion and a plurality of parameters are measured, including, but not limited to, a circumference of the body portion, an orientation of the body portion, a movement of the body portion, an acceleration of the body portion, or a change in any one or more of the plurality of parameters. For example, an increase in circumference may indicate flexion and a decrease in circumference may indicate extension. The methods diverge at blocks 1530 and 1630.

At block 1530 of FIG. 15, the method 1500 includes calculating a number of repetitions performed of the exercise. In some embodiments, calculating includes measuring an orientation or movement of the body portion over time, during the exercise, and extracting a pattern indicative of a repetitious movement. Such a pattern may be further processed to extract a repeating unit of the pattern indicative of one repetition. The number of repeating units are summed to determine a total number of repetitions performed.

At block 1540 of FIG. 15, the method 1500 includes comparing the number of repetitions or total number of repetitions performed to a prescribed or target number of repetitions for the exercise. In some embodiments, an individual is notified (e.g., visually, audibly, haptically) when the number of repetitions falls below a prescribed number of repetitions; in such embodiments, a caregiver, friend, family member, peer, and/or healthcare provider may also be notified. Alternatively or additionally, the user is notified when the number of repetitions exceeds or meets a prescribed number of repetitions. In the case of exceeding the prescribed number, the system may warn the user to not exacerbate existing injuries or incur new injuries by exceeding the prescribed number or the system may congratulate the user or provide positive feedback to the user when the user is trying to increase muscle tone or strength. The calculations and comparisons may be performed locally in the sensor system or remotely on a mobile computing device, network computing device, or supervisor computing device.

At block 1550 of FIG. 15, the method 1500 includes comparing the performance of one or more repetitions performed on the current day to repetitions performed on previous days. In some embodiments, the comparison of current performance with previous performance may be used to compute one or more of the scores (e.g., adherence score, performance score, overall score, etc.). In additional or alternative embodiments, the performance of the repetitions may be combined with one or more aspects of user/patients performance or state, including for example adherence to medicines, pain level, exercise adherence, and/or range of motion.

At block 1630 of FIG. 16, the method includes calculating a quality of performance of an exercise. In some embodiments, calculating includes detecting one or more of: a body portion orientation, movement, circumferential change, and one or more parameters derived from one or more of: the detected body portion orientation, movement, and circumferential change. Calculating may additionally or alternatively include extracting a pattern of movements, positions, orientations, circumferential changes, and additional parameters. For example, if the exercise is a bicep curl, the extracted pattern may include a series of five movements, orientations, and circumferential changes equaling one repetition repeated over time: (1) full extension of the arm combined with a first circumference reading, (2) partial (e.g., 90 degree) flexion combined with a second circumference reading, (3) full flexion combined with a third circumference reading, (4) partial (e.g., 90 degree) flexion combined with a fourth circumference reading, and (5) full extension combined with a fifth circumference reading. In some embodiments, a measure of quality of an exercise is averaged over a series or set of movements or repetitions, for example, if the user had high quality at the beginning of the exercise set but waning quality at the end of the exercise set.

In some embodiments, the one or more derived parameters include an undesirable body portion orientation, a circumferential change in a specific muscle or muscle group, a body portion angle, a speed of the exercise, or a timing of the exercise.

In some embodiments, the one or more derived parameters include an undesirable limb or body portion orientation during the exercise. For example, in some exercises, there is a tendency to move the limb or body portion in a way that reduces the efficacy of the exercise. A measurement of this movement may be used to calculate a quality of performance of an exercise. In some embodiments, a limb orientation or body portion orientation is calculated or presented to the user as a percentage of a maximum value, the maximum value being a preferred value of the exercise. For example, the lower the measured value of the undesirable body portion orientation, the lower the quality score or quality indicator for performance of the exercise.

In some embodiments, the one or more derived parameters include detecting flexion or lack of flexion of a limb or body portion. For example, as a limb is flexed, a circumference of a limb increases to reflect the flexing of muscles. If the correct muscle or muscle group is being flexed during the exercise, a detected change in circumference for the correct muscle or muscle group of the limb or body portion would increase resulting in an increased quality score or quality indicator. If an incorrect muscle group is being flexed during the exercise, a detected change in the circumference for the correct muscle or muscle group would be minimal or there would be no detected change in circumference indicating that the exercise is not being done correctly resulting in a decrease in the quality score or quality indicator.

In some embodiments, the one or more derived parameters include a limb angle achieved as compared to target limb angle for the exercise. In some such embodiments, the limb angle may be computed or displayed as a percent of a maximum value or as a percentage or value relative to a threshold value. For example, for weight lifting exercises, stretching exercises, or core exercises, a threshold value may be a time-based goal for the individual or a target goal for the individual. In such embodiments, if the individual surpasses the time-based goal or target, the individual has achieved greater strength, flexibility, or range of motion thus increasing a quality indicator or score; if the individual fails to reach the threshold, the individual has not met his/her strength, flexibility, or range of motion goals set by a healthcare provider or himself/herself thus reducing a quality indicator or score. For exercises in which hyper-flexion or hyper-extension is undesirable or detrimental, surpassing a time-based goal or a target would result in a reduced quality factor or indicator.

In some embodiments, the one or more derived parameters include a speed and/or timing of an exercise. For example, some exercises are not as effective if they are rushed or some exercises include moving a limb to a specified orientation and maintaining the specified orientation for a prescribed length of time before returning to the original or baseline orientation. In such embodiments, a derived parameter includes an actual holding time versus a desired holding time or an actual repetition time versus a desired repetition time.

At block 1640 of FIG. 16, the method includes comparing the quality of performance of the exercise to one or more ideal values for the one or more of: the detected body portion orientation, the detected body portion movement, the detected body portion circumferential change, and the one or more parameters or a template pattern for the exercise. Block 1640 functions to determine whether the individual completes a repetition as defined by the system or is only performing a fraction of the exercise or is performing the exercise in a sloppy or imprecise manner. The system may generate a quality score or quality indicator based on a difference between the one or more ideal values and the actual detected values or between the template pattern and the actual pattern. In some embodiments, the orientation, movement, circumferential change, and one or more parameters are measured over time during the exercise to further determine whether the individual is rushing through the exercises or whether the individual is performing the exercise slowly or intently.

In some embodiments, methods 1500/1600 further include receiving a notification regarding a recommended or prescribed exercise from a healthcare provider. Alternatively or additionally, methods 1500/1600 include receiving a user input indicative of an exercise.

In some embodiments, one or more methods described elsewhere herein include comparing the measurements for the plurality of parameters to a set of previous measurements for the plurality of parameters. Such comparison allows historical tracking of measurements over time. Further, in some embodiments, the method includes determining a range of motion of the body portion or an improvement in the range of motion of the body portion over time. In some such embodiments, the method includes calculating the range of motion of the body portion by comparing a first orientation of the body portion to a second orientation of the body portion. For example, a user may start at a range of motion of 20° (i.e., 0° to 20° in movement) as measured by the sensor system and incrementally increase to 40° (i.e., 0° to 40° in movement). The method of some embodiments further includes differentiating fluid range of motion (i.e., the user reaches 40° from 0°) versus stuttering range of motion (i.e., the user starts from 0° and reaches 20° then comes back to 15° and then reaches 40°). The system may differentiate between fluid and stuttering range of motion using movement measurements, as described elsewhere herein. Fluid range of motion is weighted more heavily than stuttering range of motion for purposes of overall score calculations. Alternatively or additionally, the method includes calculating the range of motion of the body portion by comparing a first orientation of the body portion to a second orientation of a second body portion. A non-limiting example of such embodiments includes an individual lying on his/her back on a table and bending his/her knee as far as he/she can while maintaining the foot planted on the table. The angle between the body portion and the second body portion is measured to determine a range of motion of the body portion.

In some embodiments, the various methods described herein include determining a progress of the individual towards a time-based or a future goal for a range of motion of the body portion. For example, for a time-based goal, if the user adheres to prescribed exercises, prescriptions, and other instructions from the healthcare provider, the user should reach a pre-determined range of motion in a pre-determined period of time. Such time-based goals may be updated periodically by the system as the user reaches or fails to reach various milestones, completes or fails to complete various exercises, or complies with or fails to comply with various instructions given by the healthcare provider. Further for example, for a future goal, the user should reach full recovery (e.g., full range of motion or at least recover to his/her range of motion prior to injury or surgery) in a pre-determined period of time and/or after completing or adhering to various instructions (e.g., prescribed exercises, prescriptions, etc.) from a healthcare provider. In some embodiments, determining includes benchmarking the range of motion of the body portion to a previous range of motion reading or to a future range of motion goal or a future time-based goal. The future range of motion goal is based on one or more of: a prescribed exercise, one or more user-initiated range of motion measurements, and time. In some embodiments, the method includes generating a progress indication for the range of motion of the body portion relative to the time-based goal, the future range of motion goal, or one or more previous range of motion readings. In some embodiments, the methods described in FIGS. 15-16 are performed locally by the sensor system; in other embodiments, the methods are performed by the mobile computing device, network computing device, and/or supervisor computing device.

In some embodiments, an alert output is generated when the overall score exceeds a predefined threshold. In some embodiments, an alert output is generated when a compliance score falls below a predefined threshold. In some embodiments, an alert output reporting progress is generated following every receipt of a parameter measurement. In some embodiments, a supervisor can configure when an alert output is generated. In some embodiments, the alert output is a visual or audible alert presented by the mobile computing device 600. Additionally or alternatively, the alert output may be a message that is transmitted to another communicatively connected device, such as a supervisor computing device or a reviewer computing device.

Figure 9:
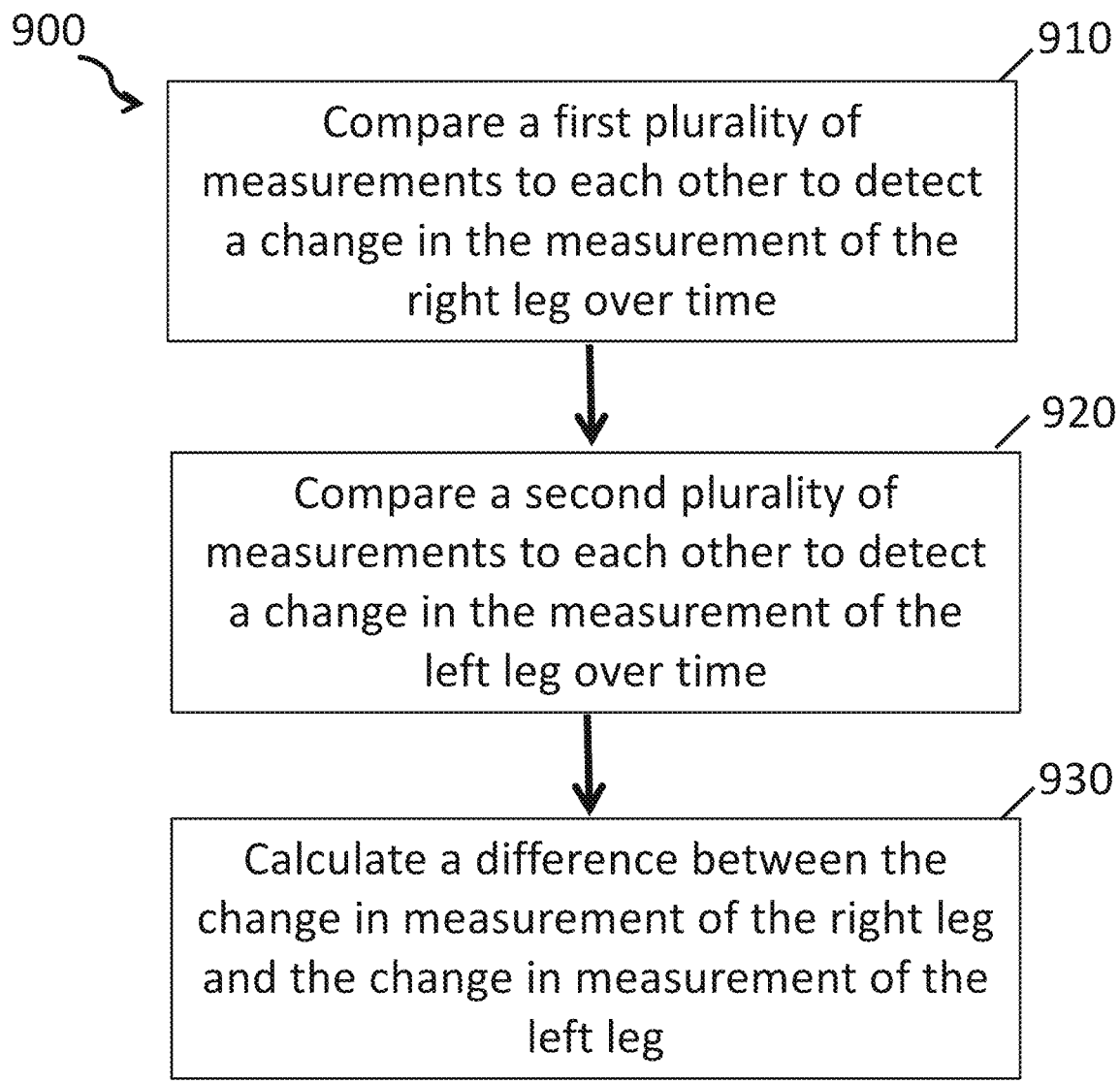
FIG. 9 illustrates a flow chart of another embodiment of a method performed by the mobile computing device of FIG. 6.

In some embodiments, the specific data analysis functions performed by the mobile computing device 600 are customized based on the intended use/purpose of the monitoring system. One example of a specialized method of data analysis performed by the mobile computing device 600 is provided in FIG. 9. In the illustrated example, the mobile computing device 600 is communicatively coupled to a sensor system 300 formed of at least two stretchable components and two sensor modules. A first stretchable component with a first sensor module is positioned on the right leg of the monitored individual and configured to obtain a first set of parameter measurements, including a first set of circumference measurements. A second stretchable component with a second sensor module is positioned on the left leg of the monitored individual and configured to obtain a second set of parameter measurements, including a second set of circumference measurements. In the illustrated embodiment, processing the parameter measurements to track and analyze changes includes: comparing the first plurality of circumference measurements to each other to detect a change in the circumference of the right leg over time, as shown at block 910; comparing the second plurality of circumference measurements to each other to detect a change in the circumference of the left leg over time, as shown at block 920; and calculating a difference between the change in circumference of the right leg and the change in circumference of the left leg, as shown at block 930. The difference between the change in circumference of the right leg and the change in circumference of the left leg may contribute to a determination of the appropriate timing or content of the alert output. For example, in some embodiments, an alert output may be generated when the difference between the change in circumference of the right leg and the change in circumference of the left leg exceeds a threshold value.

Additionally, in some embodiments, the specific data analysis functions performed by the mobile computing device 600 may be further customizable for each monitored individual. In some embodiments, the analysis functions stored in software of the data processing module 626 are modifiable by system administrators and/or health and wellness professionals via interaction with an analytics system stored on a network computing device.

Analytics System

Figure 17:
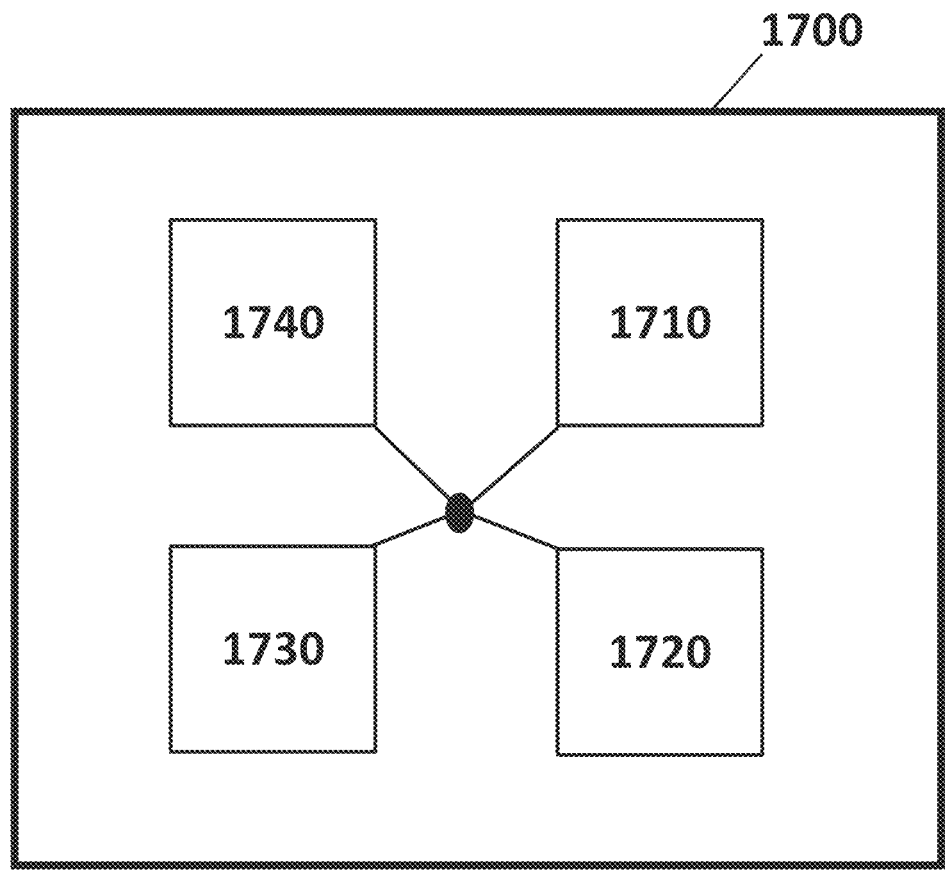
FIG. 17 illustrates a schematic block diagram of one embodiment of a network computing device provided within the monitoring system of FIG. 1C.

A schematic block diagram of the analytics system is illustrated in FIG. 17. The analytics system 1700 is stored on the network computing device 130 introduced in FIG. 1C. The analytics system refers to the backend system of the overall monitoring system. The analytics system 1700 includes a monitored-individual module 1710, a supervisor module 1720, a reviewer module 1730, and an administrator module 1740 through which each user of the monitoring system can interact with the network computing device 130.

The monitored-individual module 1710 stores all user data related to the monitored individual, including login credentials, medical history, a record of symptoms, and/or other user-entered information, and a log of parameter measurements and related analyses. It also stores all instructions that are transmitted to and downloadable by the mobile computing device 600. These include application instructions (i.e., software) and prescribed health-related instructions intended for the monitored individual. The monitored-individual module 1710 of some embodiments is also configured to perform additional analytics of the monitored individual's data and/or population-wide data. It will also be appreciated by those of skill in the art that, in some embodiments, some of or all the data analysis functions that were described above as being performed by the mobile computing device 600 may additionally or alternatively be performed by the analytics system 1700 of the network computing device.

The supervisor module 1720 hosts or stores the software for an application-based or web-based supervisor portal, which a supervisor can access using a supervisor computing device. Through the portal, a health or wellness professional can log into the monitoring system and review parameter measurements, data analyses, and alerts pertaining to one monitored individual and/or an entire population of monitored individuals. In some embodiments, the portal enables a health or wellness professional to view trends, averages, charts, and other displays of population-wide data pertaining to a plurality of their patients, clients, or athletes. The supervisor module 1720 may also enable the supervisor to configure and modify alert algorithms, which the monitoring system uses to determine when to generate alerts for the monitored individual and what alerts to generate. For example, a supervisor may be able to select which parameters to include in an overall score calculation and/or what weighting to assign each parameter. Through the supervisor portal, a health or wellness professional can also create, customize, and/or modify prescribed instructions for the monitored individual, and select specific parameters for the sensor system to monitor. The supervisor may also be able to select or compose messages for transmission to the mobile computing device of the monitored individual.

The reviewer module 1730 hosts or stores the software for an application-based or web-based reviewer portal, which a reviewer can access using a reviewer computing device. Through the portal, a reviewer can log into the monitoring system and review parameter measurements, data analyses, and alerts pertaining to a monitored individual. In some embodiments, the monitored individual may be able to control which information is shared with and viewable by a reviewer. In some embodiments, the reviewer module enables the reviewer to select or compose messages for transmission to the mobile computing device 120 of the monitored individual and/or the supervisor computing device 140.

The administrator module 1740 includes the software that enables user authentication of a system administrator. Upon logging into the system, the system administrator may be able to access, and optionally, modify, some of or all the software that forms the analytics system.

The analytics system 1700 connects all the users of the system together, enabling the transmission of information between one or more mobile computing devices, one or more supervisor computing devices, one or more reviewer computing devices, and/or one or more administrator computing devices.

In various embodiments, the network computing device, the supervisor computing devices, the reviewer computing devices, and the administrator computing devices each includes some of or all the functional components described above in relation to the mobile computing device 200 of FIG. 2, but with different software loaded thereon. For example, each device includes a processor and memory having instructions stored thereon, wherein execution of the instructions by the processor, cause the processor to perform various methods. Moreover, each of the computing devices includes a network interface for receiving and transmitting data, and each computing device may include or be coupled to an input device for receiving user inputs and an output device for conveying information.

The examples and illustrations included herein show, by way of illustration and not of limitation, specific embodiments in which the subject matter may be practiced. Other embodiments may be utilized and derived therefrom, such that modifications may be made without departing from the scope of this disclosure. This disclosure is intended to cover any and all adaptations or variations of various embodiments, and it will be readily apparent to those of ordinary skill in the art, in light of the teachings of these embodiments, that numerous changes and modifications may be made without departing from the spirit or scope of the appended claims.

What is claimed is:

1. A monitoring system for detecting an improvement in strength and a range of motion of a body portion of a user, the monitoring system comprising:
   at least one sensor configured to be worn on or around the body portion,
   the at least one sensor positioned within a stretchable component via a holder of the stretchable component,
   the holder being configured to maintain a fixed location of the at least one sensor upon the body portion,
   and wherein the at least one sensor is configured to obtain a plurality of measurements that include positional and orientational assessments of the body portion taken over a period of time and measured from the fixed location of the at least one sensor on the body portion during performance of one or more exercises provided as part of an adaptive care plan;
   a processor communicatively coupled to the at least one sensor, the processor comprising instructions stored thereon, wherein the instructions, when executed by the processor, cause the processor to:
   receive the plurality of measurements,
   extract a pattern from the plurality of measurements, wherein the pattern comprises the range of motion of the body portion and a quality of performance of the one or more exercises,
   compare the pattern to at least one baseline pattern, determine a change in the range of motion or a change in the quality of performance of the body portion based on the comparison of the pattern with the at least one baseline pattern, calculate, for the user, a recovery score based on the change in the range of motion or the change in the quality of performance, and further based on the plurality of positional and orientational measurements, wherein the recovery score includes a probability that the user, adhering to the adaptive care plan, will reach a predefined recovery state within a predefined time period;

wherein the processor is further configured to simulate multiple different recovery scores and then generate, based on the calculated recovery score and the simulation, a visual user interface dashboard including personalized messages to the user that facilitate adherence to the one or more exercises in the adaptive care plan.

2. The monitoring system of claim 1, wherein the predefined recovery state comprises a predefined measure of improvement, occurring over the predefined time period, in at least one metric associated with the user, the at least one metric being defined by a baseline performance of the user and the adaptive care plan.

3. The monitoring system of claim 2, wherein the at least one metric comprises one or more of a fatigue level, an adherence score, a pain level, the range of motion, a strength level, and a coordination or balance metric.

4. The monitoring system of claim 1, wherein the instructions, when executed by the processor, further cause the processor to:

receive a user input indicating a level of pain being experienced by the user;

and adjust the recovery score and the predefined time period based on the received user input.

5. The monitoring system of claim 1, wherein the recovery score further includes a probability that the user, after a surgical procedure, will regain, within the predefined time period, one or more of a strength level of the body portion, a coordination level associated with the body portion, and the range of motion associated with the body portion.

6. The monitoring system of claim 1, wherein the user interface dashboard further includes one or more of:

instructions for the one or more exercises, measurements obtained from the sensors, the recovery score, and a compliance score indicating a level of compliance by the user to the adaptive care plan.

7. The monitoring system of claim 1, further comprising: generating, based on the measurements, a risk score for the user, the risk score including a probability generated by weighting the changes, over the period of time, in each of the plurality of measurements, wherein the risk score is a risk for user readmission to a medical facility, a risk of the user falling, or a risk associated with adherence to the adaptive care plan.

8. The monitoring system of claim 1, wherein the recovery score further includes a probability that the user will regain, within the predefined time period, one or more of a strength level of the body portion, a coordination level associated with the body portion, and the range of motion associated with the body portion.

9. The monitoring system of claim 1, wherein the quality of the performance of the one or more exercises comprises one or more of:

a measure of flexibility, a measure of strength, a measure of endurance, a measure of timing, a measure of smoothness of movement, a measure of shakiness of movement, positional information, relative fatigue levels, a measure of speed of movement, and a combination thereof.

10. A monitoring system for detecting an improvement in strength and a range of motion of a body portion of a user, the monitoring system comprising:

at least one sensor configured to be worn on or around the body portion, the at least one sensor positioned within a stretchable component via a holder of the stretchable component, the holder being configured to maintain a fixed location of the at least one sensor upon the body portion, and wherein the at least one sensor is configured to obtain a plurality of measurements of the body portion taken over a period of time and from the fixed location of the at least one sensor during performance of one or more exercises provided as part of an adaptive care plan;

a processor communicatively coupled to the at least one sensor, the processor comprising instructions stored thereon, wherein the instructions, when executed by the processor, cause the processor to:

receive the plurality of measurements, extract a pattern from the measurements, wherein the pattern comprises the range of motion of the body portion, compare the pattern to a baseline pattern, determine a change in the range of motion of the body portion based on the comparison of the pattern with the baseline pattern, calculate, for the user, a time-based prediction for recovery associated with the body portion based at least in part on the change in the range of motion, the plurality of measurements, and adherence to performance of exercises associated with the adaptive care plan, wherein the processor is further configured to simulate multiple different time-based predictions for recovery and then generate, based on the calculated prediction and the simulation, a visual user interface dashboard including personalized messages to the user that facilitate adherence to the one or more exercises provided as part of the adaptive care plan.

11. The monitoring system of claim 10, wherein the time-based prediction for recovery is further based on patient reported outcome data and patient generated health data.

12. The monitoring system of claim 10, wherein a quality of the performance of the one or more exercises comprises one or more of:

a measure of flexibility, a measure of strength, a measure of endurance, a measure of timing, a measure of smoothness of movement, a measure of shakiness of movement, positional information, relative fatigue levels, a measure of speed of movement, and a combination thereof.

13. The monitoring system of claim 10, wherein the fixed location of the body portion comprises a right limb or a left limb of the user, and wherein the processor is further configured to compare the plurality of measurements to determine a probability of complete recovery of the body portion by a particular time.

14. The monitoring system of claim 10, wherein the time-based prediction for recovery further includes a probability that the user will regain, within a predefined time period, one or more of a strength level of the body portion, a coordination level associated with the body portion, and the range of motion associated with the body portion.

\* \* \* \* \*